(12) United States Patent
Pate et al.

(10) Patent No.: US 11,826,093 B2
(45) Date of Patent: *Nov. 28, 2023

(54) DEVICES AND METHODS FOR FORMING A FISTULA

(71) Applicant: TVA Medical, Inc., Franklin Lakes, NJ (US)

(72) Inventors: Thomas D. Pate, Austin, TX (US); Dana R. Mester, Austin, TX (US); William E. Cohn, Ballaire, TX (US); Philip M. Tetzlaff, Austin, TX (US)

(73) Assignee: TVA MEDICAL, INC., Franklin Lakes, NJ (US)

( * ) Notice: Subject to any disclaimer, the term of this patent is extended or adjusted under 35 U.S.C. 154(b) by 414 days.

This patent is subject to a terminal disclaimer.

(21) Appl. No.: 17/307,708

(22) Filed: May 4, 2021

(65) Prior Publication Data

US 2021/0267675 A1 Sep. 2, 2021
US 2023/0165631 A9 Jun. 1, 2023

Related U.S. Application Data

(63) Continuation of application No. 15/406,755, filed on Jan. 15, 2017, now Pat. No. 11,026,743.
(Continued)

(51) Int. Cl.
*A61B 18/12* (2006.01)
*A61B 18/14* (2006.01)
(Continued)

(52) U.S. Cl.
CPC ............ *A61B 18/1492* (2013.01); *A61B 6/12* (2013.01); *A61B 6/485* (2013.01); *A61B 6/487* (2013.01); *A61B 6/504* (2013.01); *A61B 18/042* (2013.01); *A61M 25/0108* (2013.01); *A61M 25/0127* (2013.01); *A61M 25/0662* (2013.01);
(Continued)

(58) Field of Classification Search
CPC .............. A61B 18/042; A61B 18/1492; A61B 2018/00577; A61B 2018/00642; A61B 2018/00875; A61B 2018/144
See application file for complete search history.

(56) References Cited

U.S. PATENT DOCUMENTS 879,034 A 2/1908 Coit
895,125 A 8/1908 Theobald
(Continued)

FOREIGN PATENT DOCUMENTS

CA 2883209 A1 4/2014
CN 1730123 A 2/2006
(Continued)

OTHER PUBLICATIONS

Chinese Office Action, Chinese Application No. 2017800170451, dated Feb. 16, 2022.
(Continued)

*Primary Examiner* — Daniel W Fowler
(74) *Attorney, Agent, or Firm* — Dickinson Wright PLLC; Andrew D. Dorisio

(57) ABSTRACT

Described here are devices, systems, and methods for forming a fistula between two blood vessels. The systems may comprise a first catheter including a housing and an electrode having a proximal end and a distal end. The proximal end is fixed relative to the housing and the distal end is longitudinally slidable within the housing.

27 Claims, 36 Drawing Sheets

Related U.S. Application Data

(60) Provisional application No. 62/399,471, filed on Sep. 25, 2016, provisional application No. 62/279,603, filed on Jan. 15, 2016.

(51) Int. Cl.
  *A61B 6/00* (2006.01)
  *A61B 6/12* (2006.01)
  *A61B 18/04* (2006.01)
  *A61M 25/01* (2006.01)
  *A61M 25/06* (2006.01)
  *A61M 39/06* (2006.01)
  *A61B 18/00* (2006.01)
  *A61B 90/00* (2016.01)
  *A61B 17/00* (2006.01)
  *A61N 1/05* (2006.01)

(52) U.S. Cl.
  CPC ... *A61M 39/06* (2013.01); *A61B 2017/00876* (2013.01); *A61B 2018/00101* (2013.01); *A61B 2018/00214* (2013.01); *A61B 2018/00345* (2013.01); *A61B 2018/00404* (2013.01); *A61B 2018/00577* (2013.01); *A61B 2018/00642* (2013.01); *A61B 2018/00875* (2013.01); *A61B 2018/144* (2013.01); *A61B 2090/3966* (2016.02); *A61N 1/05* (2013.01)

(56) References Cited

U.S. PATENT DOCUMENTS

| | | |
|---|---|---|
| 3,649,850 A | 3/1972 | Davis |
| 3,827,436 A | 8/1974 | Stumpf et al. |
| 4,416,664 A | 11/1983 | Womack |
| 4,802,475 A | 2/1989 | Weshahy |
| 5,313,943 A | 5/1994 | Houser et al. |
| 5,383,460 A | 1/1995 | Jang et al. |
| 5,697,909 A | 12/1997 | Eggers et al. |
| 5,782,239 A | 7/1998 | Webster, Jr. |
| 5,800,487 A | 9/1998 | Mikus et al. |
| 5,830,222 A | 11/1998 | Makower |
| 5,830,224 A | 11/1998 | Cohn et al. |
| 5,836,947 A | 11/1998 | Fleischman et al. |
| 5,895,404 A | 4/1999 | Ruiz |
| 5,971,979 A | 10/1999 | Joye et al. |
| 6,004,330 A | 12/1999 | Middleman et al. |
| 6,032,677 A | 3/2000 | Blechman et al. |
| 6,039,730 A | 3/2000 | Rabin et al. |
| 6,068,638 A | 5/2000 | Makower |
| 6,071,274 A | 6/2000 | Thompson et al. |
| 6,099,542 A | 8/2000 | Cohn et al. |
| 6,159,225 A | 12/2000 | Makower |
| 6,190,353 B1 | 2/2001 | Makower et al. |
| 6,197,025 B1 | 3/2001 | Grossi et al. |
| 6,217,575 B1 | 4/2001 | Devore et al. |
| 6,231,587 B1 | 5/2001 | Makower |
| 6,256,525 B1 | 7/2001 | Yang et al. |
| 6,283,988 B1 | 9/2001 | Laufer et al. |
| 6,287,306 B1 | 9/2001 | Kroll et al. |
| 6,302,875 B1 | 10/2001 | Makower et al. |
| 6,327,505 B1 | 12/2001 | Medhkour et al. |
| 6,347,247 B1 | 2/2002 | Dev et al. |
| 6,355,029 B1 | 3/2002 | Joye et al. |
| 6,357,447 B1 | 3/2002 | Swanson et al. |
| 6,379,353 B1 | 4/2002 | Nichols |
| 6,383,180 B1 | 5/2002 | Alonde et al. |
| 6,394,956 B1 | 5/2002 | Chandrasekaran et al. |
| 6,400,976 B1 | 6/2002 | Champeau |
| 6,428,534 B1 | 8/2002 | Joye et al. |
| 6,461,356 B1 | 10/2002 | Patterson |
| 6,464,665 B1 | 10/2002 | Heuser |
| 6,464,723 B1 | 10/2002 | Callol |
| 6,468,268 B1 | 10/2002 | Abboud et al. |
| 6,475,214 B1 | 11/2002 | Moaddeb |
| 6,475,226 B1 | 11/2002 | Belef et al. |
| 6,527,724 B1 | 3/2003 | Fenici |
| 6,527,769 B2 | 3/2003 | Angberg et al. |
| 6,542,766 B2 | 4/2003 | Hall et al. |
| 6,544,230 B1 | 4/2003 | Flaherty et al. |
| 6,569,158 B1 | 5/2003 | Abboud et al. |
| 6,569,162 B2 | 5/2003 | He |
| 6,579,311 B1 | 6/2003 | Makower |
| 6,585,650 B1 | 7/2003 | Solem |
| 6,592,577 B2 | 7/2003 | Abboud et al. |
| 6,629,987 B1 | 10/2003 | Gambale et al. |
| 6,635,053 B1 | 10/2003 | Lalonde et al. |
| 6,655,386 B1 | 12/2003 | Makower et al. |
| 6,656,173 B1 | 12/2003 | Palermo |
| 6,663,625 B1 | 12/2003 | Ormsby et al. |
| 6,669,709 B1 | 12/2003 | Cohn et al. |
| 6,673,085 B1 | 1/2004 | Berg |
| 6,676,657 B2 | 1/2004 | Wood |
| 6,682,525 B2 | 1/2004 | Lalonde et al. |
| 6,695,878 B2 | 2/2004 | Mcguckin et al. |
| 6,709,444 B1 | 3/2004 | Makower |
| 6,719,756 B1 | 4/2004 | Muntermann |
| 6,726,697 B2 | 4/2004 | Nicholas et al. |
| 6,733,494 B2 | 5/2004 | Abboud et al. |
| 6,736,808 B1 | 5/2004 | Motamedi et al. |
| 6,761,708 B1 | 7/2004 | Chiu et al. |
| 6,761,714 B2 | 7/2004 | Abboud et al. |
| 6,780,181 B2 | 8/2004 | Kroll et al. |
| 6,849,073 B2 | 2/2005 | Hoey et al. |
| 6,855,143 B2 | 2/2005 | Davison et al. |
| 6,887,234 B2 | 5/2005 | Abboud et al. |
| 6,911,026 B1 | 6/2005 | Hall et al. |
| 6,932,814 B2 | 8/2005 | Wood |
| 6,936,024 B1 | 8/2005 | Houser |
| 6,960,209 B2 | 11/2005 | Clague et al. |
| 6,971,983 B1 | 12/2005 | Cancio |
| 6,981,972 B1 | 1/2006 | Arley et al. |
| 7,059,330 B1 | 6/2006 | Makower et al. |
| 7,060,063 B2 | 6/2006 | Marion et al. |
| 7,094,235 B2 | 8/2006 | Francischelli |
| 7,155,293 B2 | 12/2006 | Westlund et al. |
| 7,179,270 B2 | 2/2007 | Makower |
| 7,189,231 B2 | 3/2007 | Clague et al. |
| 7,214,234 B2 | 5/2007 | Rapacki et al. |
| 7,231,260 B2 | 6/2007 | Wallace et al. |
| 7,250,051 B2 | 7/2007 | Francischelli |
| 7,288,075 B2 | 10/2007 | Parihar et al. |
| 7,303,554 B2 | 12/2007 | Lalonde et al. |
| 7,306,598 B2 | 12/2007 | Truckai et al. |
| 7,335,198 B2 | 2/2008 | Eggers et al. |
| 7,341,063 B2 | 3/2008 | Garbibaldi et al. |
| 7,367,341 B2 | 5/2008 | Anderson et al. |
| 7,374,567 B2 | 5/2008 | Heuser |
| 7,387,636 B2 | 6/2008 | Cohn et al. |
| 7,407,506 B2 | 8/2008 | Makower |
| 7,522,950 B2 | 4/2009 | Fuimaono et al. |
| 7,628,768 B2 | 12/2009 | Faul et al. |
| 7,702,387 B2 | 4/2010 | Stevenson et al. |
| 7,727,268 B2 | 6/2010 | Cunniffe et al. |
| 7,744,596 B2 | 6/2010 | Young et al. |
| 7,811,281 B1 | 10/2010 | Rentrop |
| 7,828,814 B2 | 11/2010 | Brenneman et al. |
| 7,846,172 B2 | 12/2010 | Makower |
| 7,849,860 B2 | 12/2010 | Makower et al. |
| 7,857,809 B2 | 12/2010 | Drysen |
| 7,881,797 B2 | 2/2011 | Griffin et al. |
| 7,955,326 B2 | 6/2011 | Paul et al. |
| 7,967,769 B2 | 6/2011 | Faul et al. |
| 7,967,770 B2 | 6/2011 | Li et al. |
| 8,010,208 B2 | 8/2011 | Nimer et al. |
| 8,048,016 B2 | 11/2011 | Faul et al. |
| 8,052,680 B2 | 11/2011 | Tassett et al. |
| 8,062,321 B2 | 11/2011 | Heuser et al. |
| RE43,007 E | 12/2011 | Elonde et al. |
| 8,075,555 B2 | 12/2011 | Truckai et al. |
| 8,088,171 B2 | 1/2012 | Brenneman |
| 8,100,899 B2 | 1/2012 | Doty et al. |
| 8,118,809 B2 | 2/2012 | Paul et al. |
| 8,135,467 B2 | 3/2012 | Markowitz et al. |

(56) References Cited

U.S. PATENT DOCUMENTS

| | | |
|---|---|---|
| 8,142,454 B2 | 3/2012 | Harrison et al. |
| 8,192,425 B2 | 6/2012 | Mirza et al. |
| 8,200,466 B2 | 6/2012 | Spilker et al. |
| 8,226,592 B2 | 7/2012 | Brenneman et al. |
| 8,231,618 B2 | 7/2012 | Viswanathan et al. |
| 8,236,014 B2 | 8/2012 | Brenneman et al. |
| 8,262,649 B2 | 9/2012 | Francischelli |
| 8,273,095 B2 | 9/2012 | Brenneman et al. |
| 8,328,797 B2 | 12/2012 | Wilson et al. |
| 8,333,758 B2 | 12/2012 | Joye et al. |
| 8,361,061 B2 | 1/2013 | Esch et al. |
| 8,366,707 B2 | 2/2013 | Kassab et al. |
| 8,382,697 B2 | 2/2013 | Brenneman et al. |
| 8,409,196 B2 | 4/2013 | Durgin et al. |
| 8,413,664 B2 | 4/2013 | Appling |
| 8,414,572 B2 | 4/2013 | Davison et al. |
| 8,419,681 B2 | 4/2013 | Sell |
| 8,439,909 B2 | 5/2013 | Wang et al. |
| 8,454,587 B2 | 6/2013 | Lalonde et al. |
| 8,475,441 B2 | 7/2013 | Babkin et al. |
| 8,486,062 B2 | 7/2013 | Belhe et al. |
| 8,486,064 B2 | 7/2013 | Van Wyk et al. |
| 8,551,032 B2 | 10/2013 | Faul et al. |
| 8,574,185 B2 | 11/2013 | Faul et al. |
| 8,585,700 B2 | 11/2013 | Katou |
| 8,608,754 B2 | 12/2013 | Wensel et al. |
| 8,641,724 B2 | 2/2014 | Brenneman et al. |
| 8,649,879 B2 | 2/2014 | Digiore et al. |
| 8,676,309 B2 | 3/2014 | Deem et al. |
| 8,685,014 B2 | 4/2014 | Babkin et al. |
| 8,700,179 B2 | 4/2014 | Pianca et al. |
| 8,715,281 B2 | 5/2014 | Barlow et al. |
| 8,758,334 B2 | 6/2014 | Coe et al. |
| 8,771,267 B2 | 7/2014 | Kunis et al. |
| 8,784,409 B2 | 7/2014 | Robilotto et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2 | 5/2015 | Miller et al. |
| 9,072,880 B2 | 7/2015 | Phillips et al. |
| 9,089,316 B2 | 7/2015 | Baust et al. |
| 9,108,018 B2 | 8/2015 | Dickinson et al. |
| 9,155,827 B2 | 10/2015 | Franano |
| 9,204,916 B2 | 12/2015 | Lalonde |
| 9,259,340 B2 | 2/2016 | Heuser et al. |
| 9,283,034 B2 | 3/2016 | Katoh et al. |
| 9,307,992 B2 | 4/2016 | Wilson et al. |
| 9,314,329 B2 | 4/2016 | Dickinson et al. |
| 9,326,792 B2 | 5/2016 | Dickinson et al. |
| 9,364,280 B2 | 6/2016 | Zarins et al. |
| 9,402,560 B2 | 8/2016 | Organ et al. |
| 9,408,661 B2 | 8/2016 | Haverkost |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2 | 11/2016 | Rios et al. |
| 9,510,901 B2 | 12/2016 | Steinke et al. |
| 9,623,217 B2 | 4/2017 | Pillai |
| 9,706,998 B2 | 7/2017 | Dickinson et al. |
| 9,782,201 B2 | 10/2017 | Dickinson et al. |
| 9,782,533 B2 | 10/2017 | Brenneman et al. |
| 10,045,817 B2 | 8/2018 | Miller et al. |
| 10,265,206 B2 | 4/2019 | Heuser et al. |
| 10,517,637 B2 | 12/2019 | Dickinson et al. |
| 10,543,308 B2 | 1/2020 | Lenihan et al. |
| 10,575,974 B2 | 3/2020 | De Pablo Pea et al. |
| 10,596,356 B2 | 3/2020 | Lenihan et al. |
| 2001/0012949 A1 | 8/2001 | Forber |
| 2001/0029384 A1 | 10/2001 | Nicholas et al. |
| 2002/0072739 A1 | 6/2002 | Lee et al. |
| 2002/0113678 A1 | 8/2002 | Creighton |
| 2002/0120266 A1 | 8/2002 | Truckai et al. |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0167506 A1 | 8/2004 | Chen |
| 2004/0176762 A1 | 9/2004 | Awes et al. |
| 2004/0215220 A1 | 10/2004 | Dolan et al. |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1 | 11/2005 | Anderson et al. |
| 2006/0079897 A1 | 4/2006 | Harrison et al. |
| 2006/0111704 A1 | 5/2006 | Brenneman et al. |
| 2006/0189896 A1 | 8/2006 | Davis et al. |
| 2007/0173878 A1 | 7/2007 | Heuser |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2007/0293856 A1 | 12/2007 | Paul et al. |
| 2008/0021532 A1 | 1/2008 | Kveen et al. |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1 | 5/2008 | Brenneman et al. |
| 2008/0140061 A1 | 6/2008 | Toubia et al. |
| 2008/0161901 A1 | 7/2008 | Heuser et al. |
| 2008/0171944 A1 | 7/2008 | Brenneman et al. |
| 2008/0183164 A1 | 7/2008 | Elkins et al. |
| 2008/0188848 A1 | 8/2008 | Deutmeyer et al. |
| 2008/0221519 A1 | 9/2008 | Schwach et al. |
| 2008/0275442 A1 | 11/2008 | Paul et al. |
| 2008/0312577 A1 | 12/2008 | Drasler et al. |
| 2009/0036872 A1 | 2/2009 | Fitzgerald et al. |
| 2009/0076324 A1 | 3/2009 | Takayama et al. |
| 2009/0093791 A1 | 4/2009 | Heuser |
| 2009/0112119 A1 | 4/2009 | Kim |
| 2009/0118722 A1 | 5/2009 | Ebbers et al. |
| 2009/0124847 A1 | 5/2009 | Doty et al. |
| 2009/0187098 A1 | 7/2009 | Makower et al. |
| 2009/0198232 A1 | 8/2009 | Young et al. |
| 2009/0248148 A1 | 10/2009 | Shaolian et al. |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 | 4/2010 | Kassab |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Dietz et al. |
| 2010/0280514 A1 | 11/2010 | Zerfas et al. |
| 2010/0286705 A1 | 11/2010 | Vassiliades, Jr. |
| 2010/0292685 A1 | 11/2010 | Katoh et al. |
| 2010/0298645 A1 | 11/2010 | Deutch |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1 | 9/2011 | Kraemer et al. |
| 2011/0270149 A1 | 11/2011 | Faul et al. |
| 2011/0288392 A1 | 11/2011 | De La Rama et al. |
| 2011/0288544 A1 | 11/2011 | Verin et al. |
| 2011/0306959 A1 | 12/2011 | Kellerman et al. |
| 2011/0306993 A1 | 12/2011 | Hull et al. |
| 2011/0319976 A1 | 12/2011 | Iyer et al. |
| 2012/0010556 A1 | 1/2012 | Faul et al. |
| 2012/0022518 A1 | 1/2012 | Levinson |
| 2012/0035539 A1 | 2/2012 | Tegg |
| 2012/0046678 A1 | 2/2012 | Lemaitre et al. |
| 2012/0059398 A1 | 3/2012 | Pate et al. |
| 2012/0065652 A1 | 3/2012 | Cully et al. |

(56) References Cited

U.S. PATENT DOCUMENTS

| | | |
|---|---|---|
| 2012/0078342 A1 | 3/2012 | Vollkron et al. |
| 2012/0089123 A1 | 4/2012 | Organ et al. |
| 2012/0101423 A1 | 4/2012 | Brenneman |
| 2012/0116354 A1 | 5/2012 | Heuser |
| 2012/0157992 A1 | 6/2012 | Smith et al. |
| 2012/0209377 A1 | 8/2012 | Machold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |
| 2012/0302935 A1 | 11/2012 | Miller et al. |
| 2013/0041306 A1 | 2/2013 | Faul et al. |
| 2013/0056876 A1 | 3/2013 | Harvey et al. |
| 2013/0110105 A1 | 5/2013 | Vankov |
| 2013/0172881 A1 | 7/2013 | Hill et al. |
| 2013/0190744 A1 | 7/2013 | Avram et al. |
| 2013/0190754 A1 | 7/2013 | Paul et al. |
| 2013/0216351 A1 | 8/2013 | Griffin |
| 2013/0226170 A1 | 8/2013 | Seddon et al. |
| 2013/0261368 A1 | 10/2013 | Schwartz |
| 2013/0282000 A1 | 10/2013 | Parsonage |
| 2013/0296704 A1 | 11/2013 | Magnin et al. |
| 2014/0012251 A1 | 1/2014 | Himmelstein et al. |
| 2014/0031674 A1 | 1/2014 | Newman et al. |
| 2014/0094791 A1 | 4/2014 | Hull et al. |
| 2014/0100557 A1 | 4/2014 | Bohner et al. |
| 2014/0100562 A1 | 4/2014 | Sutermeister et al. |
| 2014/0107642 A1 | 4/2014 | Rios et al. |
| 2014/0166098 A1 | 6/2014 | Kian et al. |
| 2014/0188028 A1 | 7/2014 | Brenneman et al. |
| 2014/0276335 A1 | 9/2014 | Pate |
| 2015/0005759 A1 | 1/2015 | Welches et al. |
| 2015/0011909 A1 | 1/2015 | Holmin et al. |
| 2015/0018810 A1 | 1/2015 | Baust et al. |
| 2015/0057654 A1 | 2/2015 | Leung et al. |
| 2015/0057687 A1 | 2/2015 | Gittard et al. |
| 2015/0080886 A1 | 3/2015 | Miller et al. |
| 2015/0094645 A1 | 4/2015 | Omar-Pasha |
| 2015/0112195 A1 | 4/2015 | Berger et al. |
| 2015/0134055 A1 | 5/2015 | Spence et al. |
| 2015/0141836 A1 | 5/2015 | Naumann et al. |
| 2015/0164573 A1 | 6/2015 | Delaney |
| 2015/0196309 A1 | 7/2015 | Matsubara et al. |
| 2015/0196356 A1 | 7/2015 | Kauphusman et al. |
| 2015/0196360 A1 | 7/2015 | Grantham et al. |
| 2015/0201962 A1 | 7/2015 | Kellerman et al. |
| 2015/0258308 A1 | 9/2015 | Pate |
| 2015/0297259 A1 | 10/2015 | Matsubara et al. |
| 2015/0313668 A1 | 11/2015 | Miller et al. |
| 2015/0320472 A1 | 11/2015 | Ghaffari et al. |
| 2016/0022345 A1 | 1/2016 | Baust et al. |
| 2016/0051323 A1 | 2/2016 | Stigall et al. |
| 2016/0058452 A1 | 3/2016 | Brenneman et al. |
| 2016/0058956 A1 | 3/2016 | Cohn et al. |
| 2016/0067449 A1 | 3/2016 | Misener et al. |
| 2016/0082234 A1 | 3/2016 | Schwartz et al. |
| 2016/0100840 A1 | 4/2016 | Brenneman et al. |
| 2016/0128855 A1 | 5/2016 | Heuser et al. |
| 2016/0135881 A1 | 5/2016 | Katoh et al. |
| 2016/0184011 A1 | 6/2016 | Krishnan |
| 2016/0206317 A1 | 7/2016 | Dickinson et al. |
| 2017/0071627 A1 | 3/2017 | Kellerman et al. |
| 2017/0119464 A1 | 5/2017 | Rios et al. |
| 2017/0172679 A1 | 6/2017 | Doty et al. |
| 2017/0202603 A1 | 7/2017 | Cohn et al. |
| 2017/0202616 A1 | 7/2017 | Pate et al. |
| 2017/0232272 A1 | 8/2017 | Perkins et al. |
| 2017/0252006 A1 | 9/2017 | Tsuruno |
| 2018/0000512 A1 | 1/2018 | Dickinson et al. |
| 2018/0083228 A1 | 3/2018 | Yang et al. |
| 2018/0116522 A1 | 5/2018 | Brenneman et al. |
| 2018/0206845 A1 | 7/2018 | Brenneman et al. |
| 2018/0344396 A1 | 12/2018 | Miller et al. |
| 2020/0038103 A1 | 2/2020 | Pappone et al. |
| 2020/0061338 A1 | 2/2020 | Pate |
| 2020/0178970 A1 | 6/2020 | Berman et al. |

FOREIGN PATENT DOCUMENTS

| | | |
|---|---|---|
| CN | 101730557 A | 6/2010 |
| CN | 103118619 A | 5/2013 |
| CN | 101730557 B | 9/2013 |
| CN | 103442652 A | 12/2013 |
| EP | 889705 A1 | 1/1999 |
| EP | 923912 A2 | 6/1999 |
| EP | 923912 A3 | 3/2000 |
| EP | 923912 B1 | 2/2004 |
| EP | 889705 A4 | 12/2007 |
| EP | 1983907 A2 | 10/2008 |
| EP | 889705 B1 | 10/2009 |
| EP | 1983907 A4 | 6/2011 |
| EP | 1983907 B1 | 5/2015 |
| JP | 11313830 A | 11/1999 |
| JP | 11512640 A | 11/1999 |
| JP | 2000508957 A | 7/2000 |
| JP | 2000511787 A | 9/2000 |
| JP | 2002537889 A | 11/2002 |
| JP | 2004501720 A | 1/2004 |
| JP | 3493464 B2 | 2/2004 |
| JP | 2004514467 A | 5/2004 |
| JP | 2006181370 A | 7/2006 |
| JP | 2010518987 A | 6/2010 |
| JP | 2014500072 A | 9/2014 |
| JP | 20215083139 A | 4/2015 |
| JP | 2015163205 A | 9/2015 |
| RU | 2168951 C1 | 6/2001 |
| WO | 9713463 A1 | 4/1997 |
| WO | 9729682 A1 | 8/1997 |
| WO | 9732532 A1 | 9/1997 |
| WO | 9733522 A1 | 9/1997 |
| WO | 98035721 A2 | 8/1998 |
| WO | 9956640 A1 | 11/1999 |
| WO | 0051510 A1 | 9/2000 |
| WO | 0202163 A2 | 1/2002 |
| WO | 0203893 A2 | 1/2002 |
| WO | 0202163 A3 | 6/2002 |
| WO | 0203893 A3 | 6/2002 |
| WO | 2007047851 A2 | 4/2007 |
| WO | 2008010039 A2 | 1/2008 |
| WO | 2008010039 A3 | 4/2008 |
| WO | 2008103832 A2 | 8/2008 |
| WO | 2009005644 A2 | 1/2009 |
| WO | 201129063 A2 | 3/2011 |
| WO | 2011100625 A2 | 8/2011 |
| WO | 2011100625 A3 | 12/2011 |
| WO | 2012015722 A1 | 2/2012 |
| WO | 2012068273 A1 | 5/2012 |
| WO | 2013112584 A1 | 8/2013 |
| WO | 2014028306 A1 | 2/2014 |
| WO | 2014052919 A1 | 4/2014 |
| WO | 2014059351 A1 | 4/2014 |
| WO | 2014137830 A1 | 9/2014 |
| WO | 2014153229 A1 | 9/2014 |
| WO | 2015040557 A1 | 3/2015 |
| WO | 2015061614 A1 | 4/2015 |
| WO | 2015085119 A1 | 6/2015 |
| WO | 2015108984 A1 | 7/2015 |
| WO | 2015138998 A1 | 9/2015 |
| WO | 2016033374 A1 | 3/2016 |
| WO | 2016033380 A1 | 3/2016 |
| WO | 2016081321 A2 | 5/2016 |
| WO | 2016081321 A3 | 8/2016 |
| WO | 2017124059 A1 | 7/2017 |
| WO | 2017124060 A1 | 7/2017 |
| WO | 2017124062 A1 | 7/2017 |
| WO | 2018057095 A1 | 3/2018 |

OTHER PUBLICATIONS

Brazilian Office Action, Brazil Application No. BR112018014112-7, dated Feb. 21, 2023.

(56) References Cited

OTHER PUBLICATIONS

International Search Report and Written Opinion dated Feb. 23, 2012, for PCT Patent Application No. PCT/ JS2011/061026, filed on Nov. 16, 2011, 8 pages.
Notice of Allowance dated Dec. 31, 2014, for U.S. Appl. No. 13/298,169, filed Nov. 16, 2011, 10 pages.
Notice of Allowance dated Mar. 11, 2015, for U.S. Appl. No. 13/298,169, filed Nov. 16, 2011, 4 pages.
Notice of Allowance dated Jan. 23, 2015, for U.S. Appl. No. 14/550,747, filed Nov. 21, 2014, 10 pages.
Notice of Allowance dated Jul. 12, 2016, for U.S. Appl. No. 14/052,477, filed Oct. 11, 2013, 7 pages.
International Search Report and Written Opinion dated Jan. 6, 2016, from the International Searching Authority for Application No. PCTUS2015047274, filed Aug. 27, 2015, 12 pages.
Invitation to Pay Additional Fees and, where Applicable, Protest Fee issued by the International Searching Authority for Application No. PCTUS2015047274, filed Aug. 27, 2015, dated Oct. 22, 2015, 2 pages.
Non-Final Office Action issued by The United States Patent and Trademark Office for U.S. Appl. No. 15/019,962, dated Apr. 3, 2018, 19 pages.
Non-Final Office Action issued by The United States Patent and Trademark Office for U.S. Appl. No. 14/838,225, dated Apr. 23, 2018, 11 pages.
Notice of Allowance issued by The United States Patent and Trademark Office for U.S. Appl. No. 14/697,451, dated Apr. 13, 2018, 13 pages.
Penultimate Office Action Issued by Japanese Patent Office for Japanese Patent Application No. 2019-235955 dated Jul. 14, 2021.
Kinnaert, et al. (1971). "Ulnar Arteriovenous Fistula for Maintenance Haemodialysis," British J. Surgery 58(9):641-643.
Gracz, et al. (1977). "Proximal forearm fistula for maintenance hemodialysis," Kidney International 11:71-75.
Choi, et al., Design of a Halbach Magnet Array Based on Optimization Techniques; IEEE Transactions on Magnetics, vol. 44, No. 10, Oct. 2008, pp. 2361-2366. (Year: 2008).
Davidson, I. et al. (2008). "Duplex Ultrasound Evaluation for Dialysis Access Selection and Maintenance: A Practical Guide," The Journal of Vascular Access 9(1): 1-9.
Maybury et al., "The Effect of Roll Angle on the Performance of Halbach Arrays," University of California-San Diego, Center for Magnetic Recording Research (2008), 19 pages.
Maybury et al., "The Effect of Roll Angle on the Performance of Halbach Arrays," University of California—San Diego, Center for Magnetic Recording Research (2008), 19 pgs.
Shenoy, S. (2009). "Surgical anatomy of upper arm: what is needed for A VF planning," The Journal of Vascular Access 10:223-232.
Vachharajani, T. (2010). "Atlas of Dialysis Vascular Access," Wake Forest University School of Medicine, 77 total pages.
Banasik et al. (2011). "A rare variant route of the ulnar artery does not contraindicate the creation of a fistula in the wrist of a diabetic patient with end-stage renal disease," Postepy Hig Med Dosw. 65:654-657.
Bode et al. (2011). "Clinical study protocol for the arch project Computational modeling for improvement of outcome after vascular access creation," J. Vase. Access 12(4):369-376.
Jennings, W. C. et al. (2011). "Primary arteriovenous fistula inflow proximalization for patients at high risk for dialysis access-associated ischemic steal syndrome," J. Vase. Surgery 54(2):554-558.
Morale et al. (2011). "Venae comitantes as a potential vascular resource to create native arteriovenous fistulae," J. Vase. Access 12(3):211-214.

Whittaker et al. (2011). "Prevention better than cure. Avoiding steal syndrome with proximal radial or ulnar arteriovenous fistulae," J. Vase. Access 12( 4):318-320.
Bharat et al. (2012). "A novel technique of vascular anastomosis to preventjuxta-anastomotic stenosis following arteriovenous fistula creation," J. Vascular Surgery 55(1):274-280.
Hakim et al., "Ulnar artery-based free forearm flap: Review of Specific anatomic features in 322 cases and related iterature," Head & Neck, Dec. 2013 (published online: 2014), Wiley Online Library.
International Search Report and Written Opinion dated Aug. 22, 2014, for PCT Patent Application No. PCT/US2014/02973 I, filed on Mar. 14, 2014, 11 pages.
International Search Report and Written Opinion dated Jan. 10, 2014, for PCT Patent Application No. PCT/US2013/064657, filed on Oct. 11, 2013, 8 pages.
Non-Final Office Action dated Aug. 8, 2014, for U.S. Appl. No. 13/298,169, filed Nov. 16, 2011, 15 pages.
International Search Report and Written Opinion dated Jun. 17, 2015, for PCT Patent Application No. PCT/US2015/020604, filed on Mar. 13, 2015, 8 pages.
Non-Final Office Action dated Jul. 29, 2015, for U.S. Appl. No. 14/052,477, filed Oct. 11, 2013, 15 pages.
Oct. 22, 2015, 2 pages.
Extended European Search Report dated Oct. 19, 2016, for EP Application No. 14 770 396.1, filed on Mar. 14, 2014, 7 pages.
Final Office Action dated Mar. 10, 2016, for U.S. Appl. No. 14/052,477, filed Oct. 11, 2013, 11 pages.
Final Office Action dated Oct. 6, 2016, for U.S. Appl. No. 14/697,451, filed Apr. 27, 2015, 11 pages.
Non-Final Office Action dated May 2, 2016, for U.S. Appl. No. 14/697,451, filed Apr. 27, 2015, 12 pages.
Extended European Search Report dated Oct. 16, 2017, for EP Application No. 11841243.6, filed Nov. 16, 2011, 6 pages.
Final Office Action dated Aug. 29, 2017, for U.S. Appl. No. 14/697,451, filed Apr. 27, 2015, 16 pages.
International Search Report and Written Opinion dated May 19, 2017, by the International Searching Authority for Application No. PCT/US2017/013610, filed Jan. 15, 2017, 10 pages.
International Search Report and Written Opinion dated Sep. 28, 2017, by the International Searching Authority for Application No. PCT/US2017/042937, filed Jul. 19, 2017, 11, pages.
International Search Report and Written Opinion dated Jun. 1, 2017, for PCT Patent Application No. PCT/US2017/13613, filed Jan. 15, 2017, 18 pages.
International Search Report and Written Opinion dated Mar. 31, 2017, for PCT Patent Application No. PCT/US17/13611, filed on Jan. 15, 2017, 10 pages.
Invitation to Pay Additional Fees and, Where Applicable, Protest Fee dated Mar. 31, 2017, for PCT Application No. PCT/US17/13613, filed Jan. 15, 2017, 3 pages.
Non-Final Office Action issued by The United States Patent and Trademark Office for U.S. Appl. No. 14/657,997, dated Oct. 18, 2017, 10 pages.
Non-Final Office Action dated Apr. 13, 2017, for U.S. Appl. No. 14/697,451, filed Apr. 27, 2015, 19 pages.
Non-Final Office Action dated Jul. 10, 2017, for U.S. Appl. No. 14/214,503, filed Mar. 14, 2014, 11 pages.
Final Office Action issued by The United States Patent and Trademark Office for U.S. Appl. No. 14/657,997, dated Jun. 22, 2018, 12 pages.
Non-Final Office Action issued by The United States Patent and Trademark Office for U.S. Appl. No. 14/214,503, dated Mar. 19, 2018, 16 pages.
Extended European Search Report for EP Application No. 17739123.2, dated Jul. 29, 2019.
International Search Report and Written Opinion pertaining to PCT/US2019/034896, dated May 12, 2020.
Extended European Search Report for EP Application No. 17853586.0, dated Apr. 29, 2020.

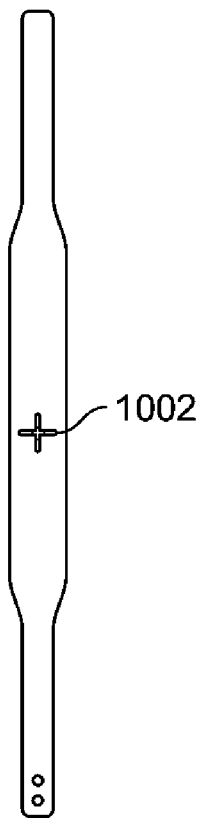
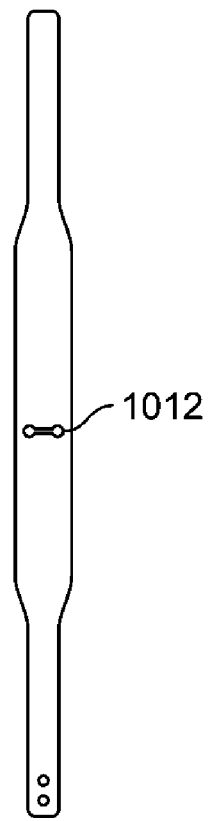
*FIG. 10A*  *FIG. 10B*

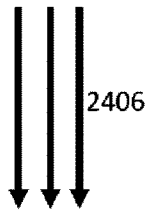
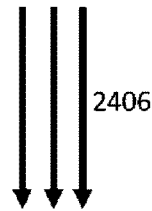
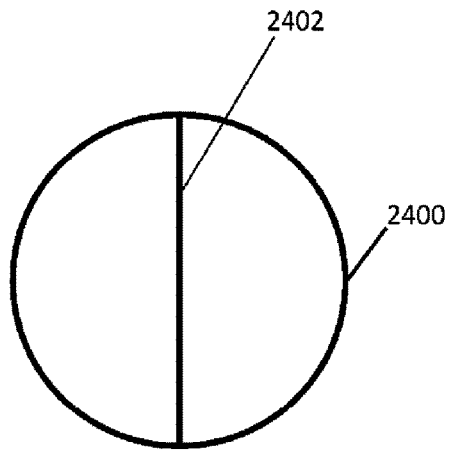
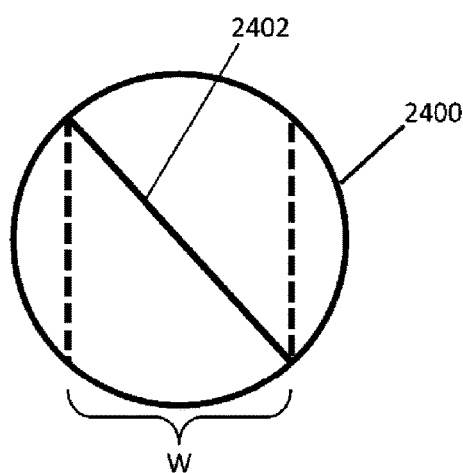
*FIG. 24A*      *FIG. 24B*
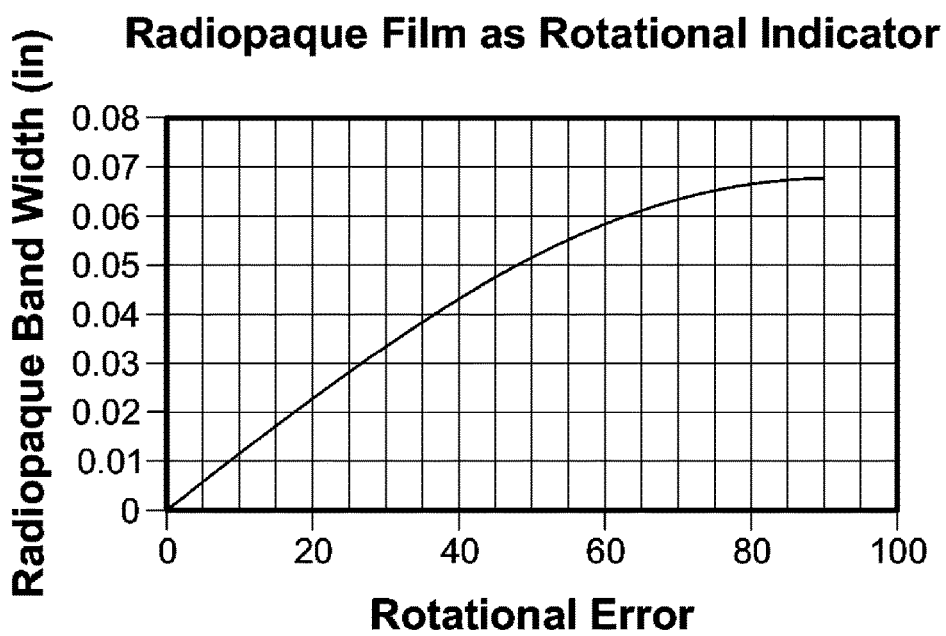
*FIG. 24C*

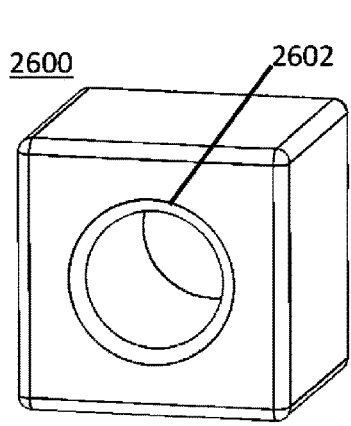
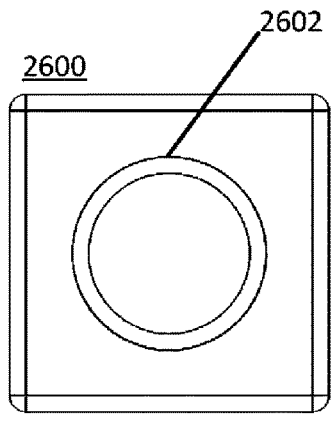
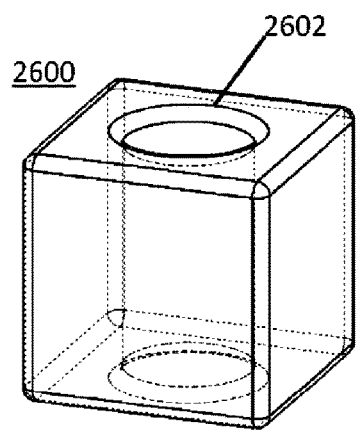
*FIG. 26A*  *FIG. 26B*  *FIG. 26C*
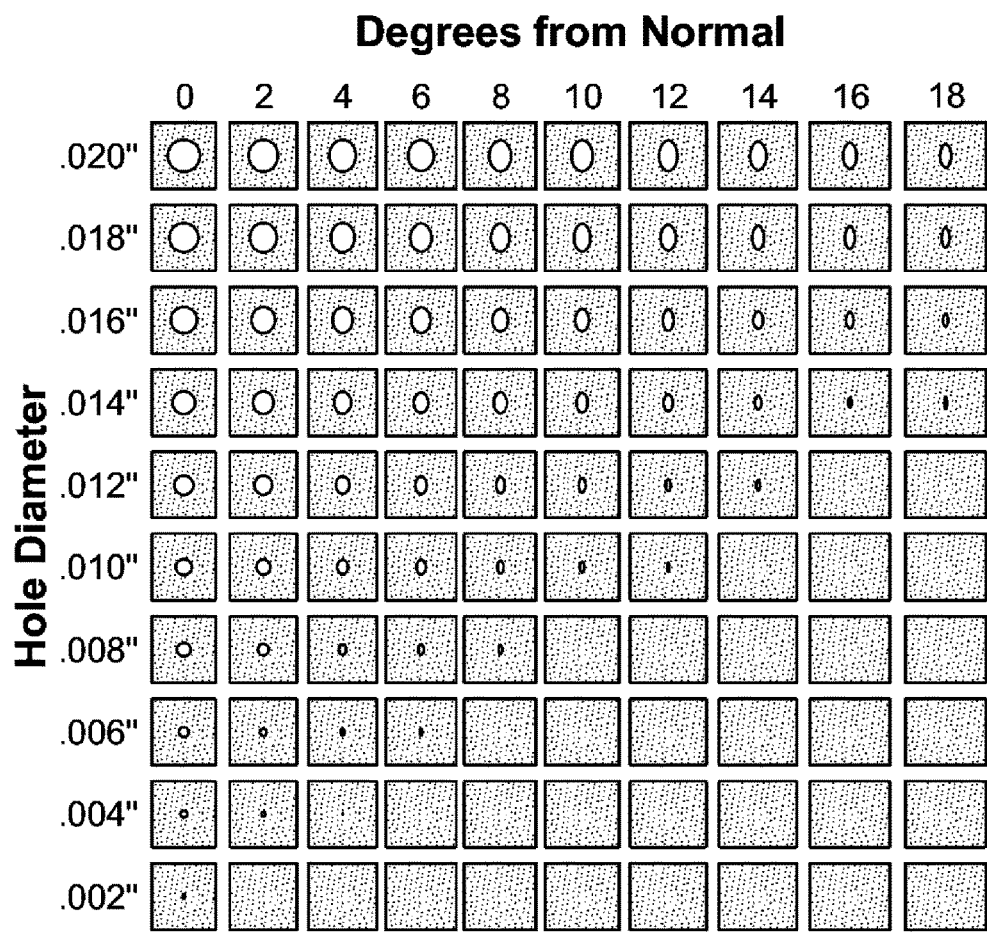
*FIG. 26D*

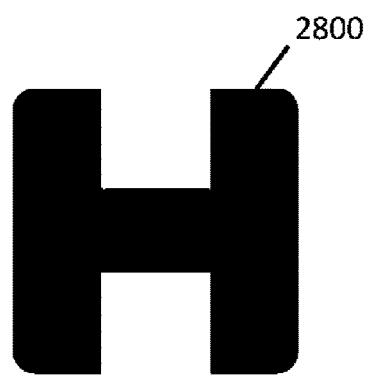
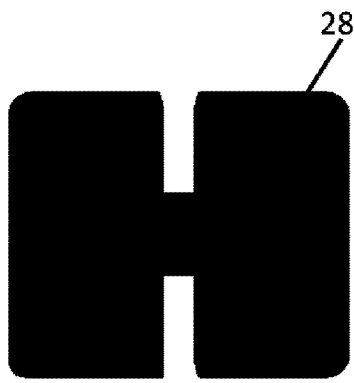
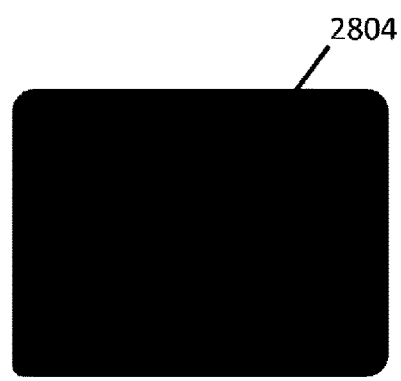
FIG. 28A  FIG. 28B  FIG. 28C
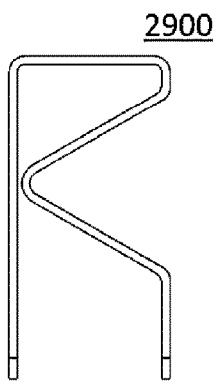
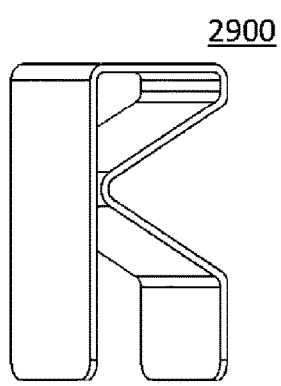
FIG. 29A  FIG. 29B
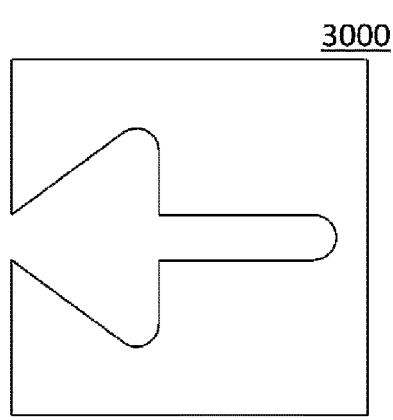
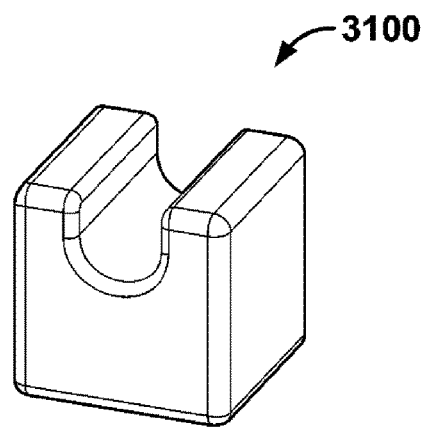
FIG. 30  FIG. 31

DEVICES AND METHODS FOR FORMING A FISTULA

CROSS-REFERENCE TO RELATED APPLICATIONS

This application is a continuation of U.S. patent application Ser. No. 15/406,755, filed Jan. 15, 2017, and titled "DEVICES AND METHODS FOR FORMING A FISTULA," which claims the benefit and U.S. Provisional Application No. 62/399,471, filed Sep. 25, 2016, and titled "DEVICES AND METHODS FOR FORMING A FISTULA" and U.S. Provisional Application No. 62/279,603, filed Jan. 15, 2016, and titled "DEVICES AND METHODS FOR FORMING A FISTULA," the entireties of which are hereby incorporated by reference.

FIELD

The current invention relates to devices and methods for forming a fistula. The devices and methods may be used to form a fistula between two blood vessels.

BACKGROUND

A fistula is generally a passageway formed between two internal organs. Forming a fistula between two blood vessels can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. In other instances, a fistula may be formed between two veins to form a veno-venous fistula. Generally, fistula formation requires surgical dissection of a target vein, and transecting and moving the vein for surgical anastomosis to the artery. It may therefore be useful to find improved ways to form a fistula between two blood vessels.

BRIEF SUMMARY

Described here are devices, systems, and methods for forming a fistula between two or more blood vessels. Generally, the system for forming a fistula between two vessels described here comprises a first catheter including a housing and an electrode having a proximal end and a distal end. The proximal end may be fixed relative to the housing and the distal end may be longitudinally slidable within the housing.

In some variations, the housing may comprise an opening and the electrode may comprise an intermediate portion between the proximal end and the distal end. In some variations, the intermediate portion may extend into and out of the opening. In some variations, the electrode may comprise a leaf spring. In some variations, the first catheter may comprise a fluid seal to prevent fluid ingress into the first catheter at the proximal end of the electrode. In some variations, the housing may comprise a heat insulating portion adjacent to at least the proximal end of the electrode. In some variations, the electrode may vary in width and/or height along its length. In some variations, the electrode may be configured to self-expand away from the housing. For example, a user may not need to actuate the electrode between a low-profile configuration and an extended configuration.

In some of these variations, the intermediate portion of the electrode may comprise a plurality of bends. In other of these variations, the intermediate portion may comprise a bend of less than about 40 degrees. In some variations, the electrode may comprise a low-profile configuration in which the electrode is recessed into the housing. In some variations, the housing may comprise a reservoir between the proximal end of the electrode and a distal end of the first catheter. The reservoir may be configured to hold fluid. The electrode may be configured to generate plasma from the fluid in the reservoir. In some variations, a feedback circuit may be configured to apply a constant square wave voltage to the electrode.

In some variations, a second catheter may comprise a second housing and a protruding backstop. In some of these variations, the protruding backstop comprises a compression region configured to oppose the electrode and compress tissue therebetween. In some of these variations, the electrode is configured to ablate the tissue along a length based on a length of the compression region. In some of these variations, the second catheter may comprise a recessed portion opposite the protruding backstop. The recessed portion may have a complementary shape to the protruding backstop. In some of these variations, the system may comprise an introducer sheath. The protruding backstop and the recessed portion may be within the introducer sheath.

In some variations, the system may further comprise a second catheter comprising a recessed backstop. The recessed backstop may have a shape that is complementary to a portion of the electrode. In some of these variations, the electrode may comprise an intermediate portion between the proximal end and the distal end. The recessed backstop may have a shape that is complementary to the intermediate portion of the electrode. In some of these variations, the electrode may comprise an extended configuration in which the electrode is extended away from the housing. The complementary shape may correspond to a shape of the electrode in the extended configuration. In some of these variations, the shape may comprise a concave portion comprising an opening configured to receive the electrode. In some of these variations, the electrode may be configured to bias towards the extended configuration.

In some variations, the first catheter may comprise a first coaption region comprising a flat coaption surface. In some of these variations, the first coaption region may have a square or rectangular cross-section. In other of these variations, the system may further comprise a second catheter comprising a second coaption region comprising a flat coaption surface. In some of these variations, the second coaption region may have a square or rectangular cross-section. In some of these variations, the first coaption region may comprise a first magnet and the second coaption region may comprise a second magnet.

The system may include one or more additional features. In some variations, the first catheter may comprise a first handle, and the system may further comprise a second catheter comprising a second handle. The first handle and the second handle may each comprise a flat surface. In some of these variations, the first catheter may comprise a first shaft and the second catheter may comprise a second shaft. The first shaft and the second shaft may each comprise braiding configured to enhance torsional stiffness. In some of these variations, the first handle may comprise a first magnet and the second handle may comprise a second magnet.

In some variations, the first catheter comprises a rotational indicator comprising a radiopaque material. In some of these variations, the rotational indicator may comprise a radiopaque film. In some of these variations, the radiopaque film may have a thickness of about 0.025 mm. In other of these variations, the rotational indicator may have a square or rectangular cross-section. In other of these variations, the rotational indicator may have a cross-section having a shape of a written character. In other of these variations, the rotational indicator may comprise a cube comprising a cylindrical cut-out. In other of these variations, the rotational indicator may comprise an arrow-shaped cut-out.

Also described herein are other systems for forming a fistula between two blood vessels. In general, these devices described herein may comprise a first catheter having a fixed height electrode comprising a wire comprising an internal portion and an external portion, and a protrusion. In some variations, the fixed height electrode may be configured to be supported by the protrusion. In some variations, the external portion of the fixed height electrode may extend away from the housing by up to about 3 mm.

Also described here are methods of forming a fistula between two blood vessels. In one variation, a method of forming a fistula between two vessels comprises advancing a first catheter into a first blood vessel. The first catheter may comprise an electrode. The method may further comprise ablating tissue with the electrode. Ablating tissue may comprise applying a constant square wave voltage to the electrode.

In some of these variations, the catheter may comprise a housing and the electrode may comprise a proximal end and a distal end. The proximal end may be fixed relative to the housing and the distal end may be longitudinally slidable within the housing. In other of these variations, a second catheter comprising a backstop may be advanced into a second blood vessel.

In some of these variations, the first catheter may comprise a first coaption region comprising a first magnet and the second catheter may comprise a second coaption region comprising a second magnet. Magnetic attraction forces between the first magnet and the second magnet may compress tissue between the backstop and the electrode.

Other methods of forming a fistula between two vessels are also described herein and may comprise advancing a first catheter into a first blood vessel and a second catheter into a second blood vessel. The first catheter may comprise a first electrode and the second catheter may comprise a conductive portion. Tissue in the first blood vessel and the second blood vessel may be ablated with the first electrode. The first electrode may contact the conductive portion after the tissue is ablated. Tissue in the second blood vessel may be ablated with the conductive portion while the conductive portion is in contact with the first electrode. In some variations, the first blood vessel may comprise a venous blood vessel and the second blood vessel may comprise an arterial blood vessel.

In some variations, a method of forming a fistula between two vessels may comprise advancing a first catheter into a first blood vessel and a second catheter into a second blood vessel. The first catheter may comprise a first electrode and the second catheter may comprise a second electrode. An ablation cycle may be performed and comprise measuring a first impedance between the first electrode and the second electrode, selecting an ablation parameter based on the first impedance, ablating tissue based on the selected ablation parameter, measuring a second impedance between the first electrode and the second electrode, and determining that a fistula has been created based on the second impedance.

In some variations, determining that the fistula has been created may comprise measuring a second impedance of about 150 ohms or less between the first electrode and the second electrode. In some of these variations, measuring may comprise measuring the first impedance and the second impedance over a measurement period of about 20 msec and ablating tissue comprises ablating tissue for an ablation period of about 40 msec. In some of these variations, the measuring may comprise measuring the first impedance and the second impedance over a measurement period of about 1 second and ablating tissue comprises ablating tissue for an ablation period of about 500 msec. In some of these variations, a first current and a second current may be applied to the electrode to induce neuromuscular stimulation, and a distance of a nerve to a fistula site may be calculated based on the induced neuromuscular stimulation. In some of these variations, the first current may comprise about 1 microampere and the second current may comprise about 3 microamperes. In other of these variations, the first catheter and the second catheter may be repositioned based on the distance of the nerve to the fistula site. In some variations, a denaturing parameter may be selected based on the first impedance, and tissue may be denatured based on the selected denaturing parameters to shrink the tissue.

Also described here are methods of positioning a first catheter and a second catheter within two vessels may comprise advancing a first catheter into a first blood vessel and a second catheter into a second blood vessel. The first catheter may comprise a first radiopaque portion and the second catheter may comprise a second radiopaque portion. An orientation of the first radiopaque portion and the second radiopaque portion may be fluoroscopically imaged using an X-ray beam. The orientation of the first radiopaque portion may be matched to that of the second radiopaque portion. The X-ray beam may be non-perpendicular to the first and second radiopaque portions.

Also described here are methods of positioning a first catheter within a first blood vessel and a second catheter within a second blood vessel comprising advancing the first catheter into the first blood vessel and the second catheter into the second blood vessel. The first catheter may comprise a first electrode and the second catheter may comprise a second electrode. An impedance may be measured between the first electrode and the second electrode. The first catheter may be aligned with the second catheter based on the measured impedance.

In some variations, aligning the first catheter with the second catheter may comprise rotationally and axially aligning the first catheter to the second catheter. In some variations, an audio and/or visual alignment signal may be generated based on the measured impedance.

BRIEF DESCRIPTION OF THE DRAWINGS

FIG. 7A is a perspective view and FIG. 7B is a cross-sectional side view.

FIGS. 10A-10B are plan views of an electrode having variations of an electrode shape.

FIG. 11A is a side view and FIG. 11B is a cross-sectional view of two vessels having a fistula formed therebetween.

FIG. 13A is a perspective view of a portion of the second catheter. FIG. 13B is a cross-sectional side view of portions of the first catheter and the second catheter.

FIG. 14A is a perspective view of a portion of the second catheter. FIG. 14B is a side view of a portion of the second catheter. FIG. 14C is a cross-sectional side view of portions of the first catheter and the second catheter.

FIG. 17A is a perspective view of a portion of the second catheter. FIG. 17B is a cross-sectional perspective view of a portion of the second catheter. FIG. 17C is a cross-sectional side view of a portion of the first catheter and the second catheter.

FIG. 19A is a perspective view of a portion of the first catheter and the second catheter. FIG. 19B is a side view of a portion of the first catheter and the second catheter. FIGS. 19C-19D are cross-sectional side views of portions of the first catheter and the second catheter.

FIG. 20A is a perspective view of a portion of the second catheter comprising the conductive portion. FIGS. 20B-20D are cross-sectional side views of portions of the first and second catheters in blood vessels.

FIGS. 22A-22B are plan views, and FIGS. 22C-22D are cross-sectional views.

FIGS. 23A and 23B are perspective views of portions of the first catheter and second catheter. FIGS. 23C-23D are cross-sectional side views of portions of the first catheter and the second catheter.

FIGS. 24A-24B are illustrative depictions of a variation of a rotational indicator. FIG. 24C depicts visualized rotational indicator width as a function of rotational error of the rotational indicator of FIGS. 24A-24B.

FIG. 25A is a perspective view and FIG. 25B is a side view of the rotational indicator.

FIGS. 26A-26C are illustrative depictions of another variation of a rotational indicator. FIGS. 26A and 26C are perspective views and FIG. 25B is a side view of the rotational indicator. FIG. 26D depicts fluoroscopic visualization of rotational indicators similar to those depicted in FIGS. 26A-26C having varying hole diameters and orientation.

FIGS. 28A-28C depict fluoroscopic visualizations of another variation of a rotational indicator having different orientations.

FIGS. 29A-29B are side and perspective views, respectively, of another variation of a rotational indicator.

FIG. 30 is a cross-sectional side view of another variation of a rotational indicator.

FIG. 31 is a perspective view of another variation of a rotational indicator.

FIG. 34A is a perspective view of the handle. FIG. 34B is a perspective view of the handle with a top portion removed. FIG. 34C is a cross-sectional perspective view of the handle.

FIG. 36A shows a side view of a distal portion of the catheters, FIG. 36B shows a cross-sectional side view of the catheter depicted in FIG. 36A, FIG. 36C shows an electrical plug of the catheter, FIG. 36D shows a side view of the electrode and backstop depicted in FIG. 36A, FIG. 36E shows a perspective view of the catheter system, FIG. 36F shows an introducer sheath over the catheter, and FIG. 36G shows a handle of the catheter.

DETAILED DESCRIPTION

Figure 1A:
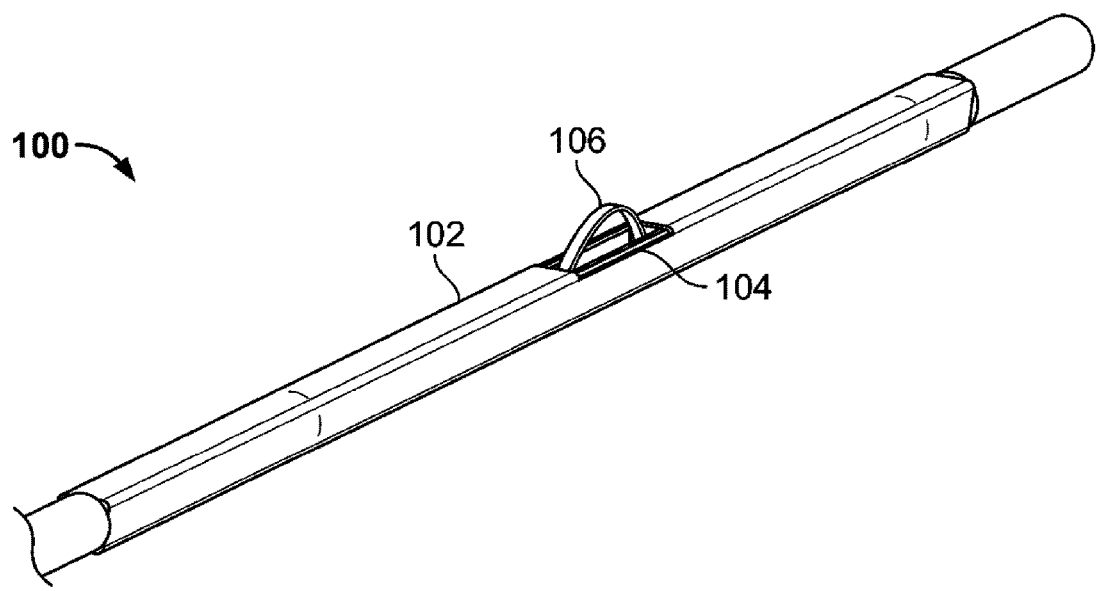
FIG. 1A is a perspective view of a portion of a catheter comprising an electrode.
Figure 1B:
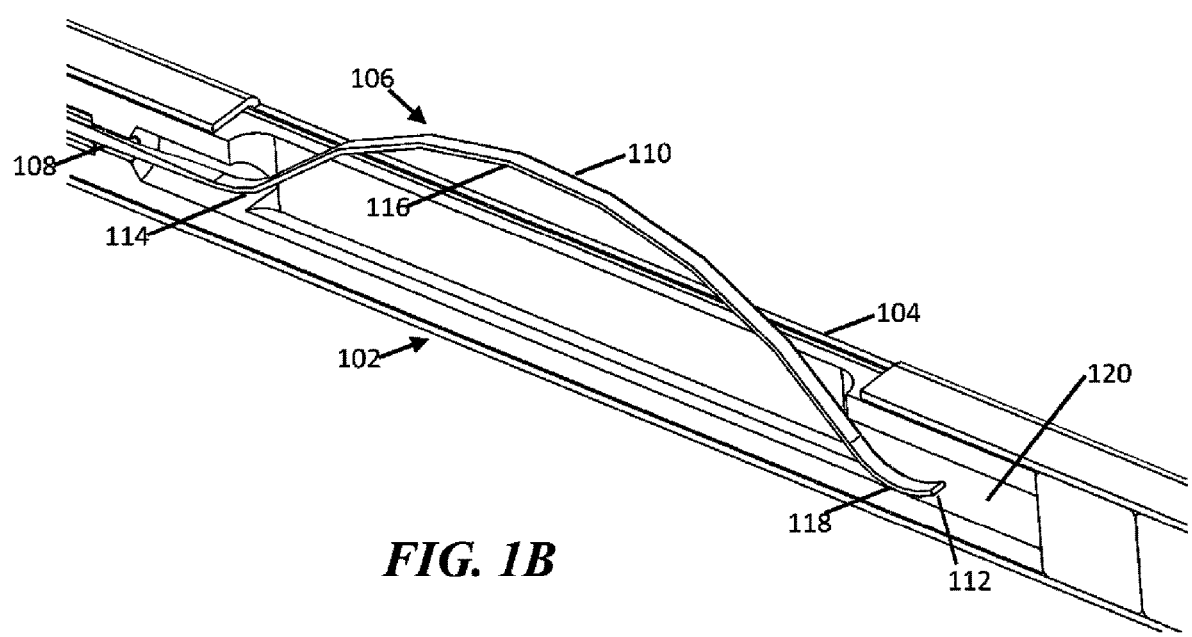
FIG. 1B is a cross-sectional perspective view of a portion of the catheter of FIG. 1A.

Generally described here are devices, systems, and methods for forming a fistula. In some variations, the devices and methods may be used to form a fistula between two blood vessels (e.g., an arteriovenous fistula between an artery and a vein or a veno-venous fistula between two veins). Generally, to form such a fistula between two blood vessels, one or more catheters may be advanced in a minimally invasive fashion through the vasculature to a target location. In some instances, a single catheter may be placed in a blood vessel to form a fistula with an adjoining blood vessel. In other instances, a system comprising multiple catheters may be used to form a fistula. For example, in some instances a catheter may be placed in each of the two blood vessels. In these instances, it should be appreciated that each catheter may or may not have the same configuration of elements, and that some catheters may be different from and/or complementary to other catheters, as will be described in more detail below. In some variations, the catheter may be removed from the vasculature after fistula formation without leaving foreign objects in the body such as a stent, coil, plug, and so forth. In some instances, a catheter configuration may be selected based on the fistula to be formed and the vessels in which the fistula is to be located. The variations as described herein below may improve treatment outcomes and reduce complications associated with fistula formation.

Generally, the systems described here comprise one or more catheters. The at least one catheter may generally comprise a housing and a fistula-forming element such as an electrode. The electrode may be attached to the housing and used to ablate tissue to form a fistula. During ablation, sufficient energy may be delivered to tissue such that the tissue is removed to form a fistula. A size and shape of an electrode and the energy applied to the electrode may be selected to form a desired fistula with minimal energy to reduce collateral damage to tissue. The electrodes described herein may allow targeted fistula formation that may accommodate a wide range of patients and fistula requirements. In some instances, an electrode may be configured to be advanced through blood vessels of varying diameters without damaging tissue. Once positioned at a fistula formation site, the electrode may in some variations naturally extend into proper position without user manipulation. During fistula formation, the electrode may continue to extend as tissue is ablated. As such, a separate electrode actuation mechanism may be rendered moot. The electrode may be formed compactly to reduce a size of the catheter and/or manufacturing complexity.

In some variations of the system, a first catheter and a second catheter may be complementary to each other where, for example, the first catheter may comprise an electrode and the second catheter may comprise a backstop that may shape and control tissue ablation performed by the first catheter electrode. In other variations, a first catheter and a second catheter may each comprise at least one electrode. In some of these variations, the first and second catheter may each comprise at least one electrode, and the electrode(s) of one of the catheters may be an active electrode, while the electrode(s) of the other of the catheters may be a return electrode. In others of these variations, the first and second catheters may form a dual ablation system that may be energized to ablate tissue from opposing sides. This may in some instances reduce an ablation time. The electrodes may be activated in a simultaneous ablation mode, alternating mode, or a combination of modes. The dual ablation systems described in more detail herein may improve safety, decrease a fistula formation time, and/or allow for a compact catheter system. In other variations, synergistic ablation may be provided where a conductive portion of one catheter is activated by electrode activation of another catheter. For example, an activated first electrode may contact a second catheter to energize a conductive portion of the second electrode.

The catheter may further comprise one or more alignment features that help align one catheter relative to another catheter in adjacent blood vessels and/or bring the catheters (and blood vessels) in closer approximation relative to each other. Alignment of the catheters relative to each other may position the fistula-forming element(s) (e.g., electrodes) of the catheters at a desired axial location and/or rotational angle relative to each other when both catheters comprise at least one fistula-forming element. When only one of two catheters comprise a fistula-forming element, alignment of the catheters relative to each other may position the fistula-forming element(s) of a first catheter at a desired axial and/or rotational angle relative to a corresponding component of a second catheter (e.g., a backstop). In some instances, alignment features of two catheters may hold respective blood vessels in a desired position throughout fistula formation and may help achieve efficient fistula formation with reduced collateral damage. In these or other instances, the alignment features may stretch and/or compress tissue at a fistula site in such a manner to allow tissue to be ablated more quickly and with less energy.

Furthermore, the alignment features as discussed in detail herein may increase user confidence in achieving catheter alignment and do so with a reduced amount of effort. In some variations, the alignment features may comprise one or more magnets, coaption surfaces (e.g., flat surfaces), visual alignment aids, and/or handles. For instance, opposing magnetic coaption surfaces may bring the catheters into rotational alignment with each other and closer together with the blood vessels. In some variations, at least a portion of the catheters described herein may have a square cross-sectional shape in order to promote rotational alignment. Magnets located within these catheters may also have a square cross-sectional shape. In some variations, the catheters may comprise magnet arrays comprising a plurality of square magnets. Additionally or alternatively, a handle may be used to align at least a portion of one catheter relative to at least a portion of another catheter. In some variations, a rotational indicator may be visualized under fluoroscopy for a user to visualize the catheters in the blood vessels and manipulate the catheter(s) into a desired position.

The electrodes disclosed herein may in some variations not only ablate tissue, but may also measure tissue and/or fistula characteristics (e.g., impedance) such as for catheter alignment and confirming fistula formation. The electrodes may be connected to, for example, a generator under control of an electrosurgical controller. Energy delivery may be tuned by the controller to improve fistula formation and limit collateral damage to tissue based on, for example, measured impedance data.

One or a combination of the catheters described herein may be used to form a fistula, as will be described in more detail herein. Generally, the methods described herein for forming a fistula between two vessels may comprise advancing a first catheter into a blood vessel in a minimally invasive manner through vasculature. After aligning the catheters at a desired location, the vessels may optionally be measured to determine tissue characteristics for tissue modification based on the measurement. Power may then be delivered to one or more electrodes to ablate tissue. For instance, an electrosurgical controller may control energy delivery based on real-time measurements to improve energy efficiency and reduce ablation time. In other variations, the amount of energy delivered may be fixed or predetermined. The catheters may be removed upon confirmation of fistula formation, which may optionally be confirmed via measurement of one or more properties. As disclosed in more detail herein, the methods described here may improve fistula patency and longevity using less energy, time, and damage to tissue.

I. Systems

A. Catheters

Generally, the systems and devices described here may be useful in measuring, modifying, and ablating tissue to form a fistula. The systems described here typically comprise one or more catheters. The one or more catheters may comprise one or more fistula-forming elements. The catheters may be configured to be advanced through vasculature in a minimally invasive manner. In some variations, a fistula may be formed by one or more active electrodes of one catheter. In other variations, two catheters each comprising one or more electrodes may simultaneously ablate tissue from opposing sides to form a fistula. In some other variations, a first catheter comprising one or more electrodes may form a fistula with a second catheter comprising one or more backstops opposing the one or more electrodes. In still other variations, a first catheter comprising one or more electrodes may form a fistula with a second catheter comprising one or more conductive portions, where the one or more conductive portions form a return electrode or are energized by contact with one or more electrodes of the first catheter.

The catheters may have any suitable diameter for intravascular use, such as, for example, about 4 French, about 5.7 French, about 6.1 French, about 7 French, about 8.3 French, between about 4 French and about 9 French, between about 4 French and about 7 French, between about 4 French and about 6 French, or the like. The catheters described may further comprise elements to aid in visualization and/or alignment of one or more catheters as described in more detail herein. Any suitable catheter or catheters may be used with the systems described herein to form the fistulas using the methods described herein.

FIG. 1A is a perspective view of a distal portion of an illustrative first catheter (100) that may be used to form a fistula between two vessels. The first catheter (100) may comprise a housing (102). An electrode (106) may protrude from an opening (104) of the housing (102), and may be activated to form a fistula. In some variations, the housing (102) may comprise one or more insulating materials which may shield or otherwise protect the catheter (100) and its components from heat generated by the electrode (106) during use. For instance, one or more portions of the housing (102) adjacent to the electrode (106) may comprise a heat insulating portion that may be ceramic.

The catheters may additionally comprise one or more lumens or passageways extending at least partially along or through the catheter. The distal end of the catheter may be configured to aid in advancement of the catheter and/or to be atraumatic. In some variations, the distal end may comprise one or more rapid exchange portions or other lumens for advancement of the catheter over a guidewire. In still other variations, the distal end may have a guidewire attached to or otherwise integrally formed with the catheter.

B. Fistula-Forming Elements

As mentioned above, the catheters described here may comprise one or more elements for forming a fistula. A fistula-forming element may comprise any element capable of forming a fistula between two vessels. For example, the fistula-forming element may comprise one or more electrical mechanisms (e.g., electrodes or electrocautery mechanisms). Generally, at least a portion of each electrode may be exposed to the surrounding environment (e.g., through one or more openings in a catheter housing) when the catheter is in a configuration for fistula formation. This exposed electrode surface may be configured to contact surrounding tissue (e.g., a blood vessel wall) and/or fluids, and may act as an ablation surface such that current may be supplied to and/or carried from tissue and fluid via the ablation surface to facilitate ablation (e.g., dissolution of solids) or vaporization (e.g., fluid to gas phase change) of tissue. In some variations, the exposed electrode surfaces may additionally or alternatively be used to perform different functions other than fistula formation. For example, the exposed electrode surface may be used to deliver an amount of energy that causes it to act as a heating surface to heat and modify tissue, rather than removing tissue to form a fistula. Additionally or alternatively, in some variations the electrode may be used to apply neuromuscular stimulation. Additionally or alternatively, in some variations the electrode may be used to measure tissue and/or fistula characteristics.

1. Low-Profile and Extended Configurations

In some variations, the electrodes described herein may be configured to have a low-profile configuration and an extended configuration. In the low-profile configuration, the electrode may be configured to be atraumatic when the catheter comprising the electrode is delivered to a location for fistula formation. For example, in the low-profile configuration, the electrode may be recessed into the catheter body, such that the outer surface of the electrode does not extend radially beyond the outer surface of the catheter body. As such, the catheter comprising the electrode may be delivered through a tubular body (e.g., blood vessel, sheath) in an atraumatic fashion. In some variations, the outer surface of the electrode may be flush with the outer surface of the catheter body in the low-profile configuration, while in other variations the outer surface of the electrode may be below the outer surface of the catheter body in the low-profile configuration. In the extended configuration, at least a portion of the electrode may extend radially outward from the outer surface of the catheter body (i.e., radially beyond the outer surface of the catheter body), and a portion of the electrode may be spaced away from the outer surface of the catheter body. As such, the electrode may contact, and in some instances press into, tissue in order to form a fistula (as described in more detail herein).

In some variations, the electrodes described herein may be biased toward the extended configuration. That is, the electrode may be configured to self-expand from the low-profile configuration to the extended configuration. In some variations, the electrode may be held in the low-profile configuration by the inner surface of a vessel wall during delivery. The electrode may then self-expand toward the extended configuration as energy delivery through the electrode results in tissue ablation (as described in more detail herein). In other variations, the electrode may be held in the low-profile configuration by another component of the catheter system, such as but not limited to a sheath.

The electrode may have any suitable shape in the low-profile and extended configurations. For example, in some variations the electrode may be curved, such that in an extended configuration it forms a convex curve extending away from the outer surface of the catheter body. When the electrode moves from a low-profile to an extended configuration, the radius of curvature of the electrode may decrease, causing the electrode to protrude from the catheter body. Conversely, when the electrode moves from an extended configuration to a low-profile configuration, the radius of curvature of the electrode may increase, causing the electrode to recess into the catheter body. As another example, in some variations the electrode may comprise one or more bends that allow it to move between low-profile and extended configurations.

In some variations, the electrodes described herein may be configured such that one or both ends of the electrode slide within the catheter body when the electrode moves between low-profile and extended configurations. For example, an electrode may comprise a first end and a second end, where both the first and second ends are located within the catheter body. A first end of the electrode may be fixed, while a second end of the electrode may be slidable within a lumen inside of the catheter body. When the slidable second end of the electrode moves toward the fixed first end of the electrode, the electrode may move toward an extended configuration. When the slidable second end of the electrode moves away from the fixed first end of the electrode, the electrode may move toward a low-profile configuration. If the electrode is curved, for example, as the slidable second end moves toward the fixed first end of the electrode, the radius of curvature of the electrode may decrease, causing the electrode to protrude from the catheter body.

An example of such a curved electrode is shown in FIGS. 1A-2B. Shown in FIG. 1A is a distal portion of an exemplary catheter (100) comprising an electrode (106), with the electrode (106) shown in an extended configuration. FIG. 1B is a cross-sectional perspective view of the catheter (100). The housing (102) of the catheter comprises an opening (104), through which the electrode (106) may extend when in the extended configuration. As shown in FIG. 1B, the electrode (106) may comprise a proximal end (108), a distal end (112), and an intermediate portion (110) between the proximal end (108) and distal end (112). The electrode (106) may comprise a proximal bend (114) between the proximal end (108) and the intermediate portion (110), an intermediate bend (116) within the intermediate portion (110), and a distal bend (118) within the distal end (112). The proximal end (108) of the electrode (106) may be fixed relative to the housing (102) in order to fix an axial and/or rotational orientation of the distal end (112) of the electrode (106) relative to the housing (102). The distal end (112) of the electrode (106) may be located within a lumen (120) within the catheter housing (102). The distal end (112) of the electrode (106) may be able to slide distally and proximally within the lumen (120) (e.g., slide longitudinally within the housing (102)), such that the intermediate portion (110) of the electrode (106) extends into and out of the opening (104) in the housing (102).

Figure 2A:
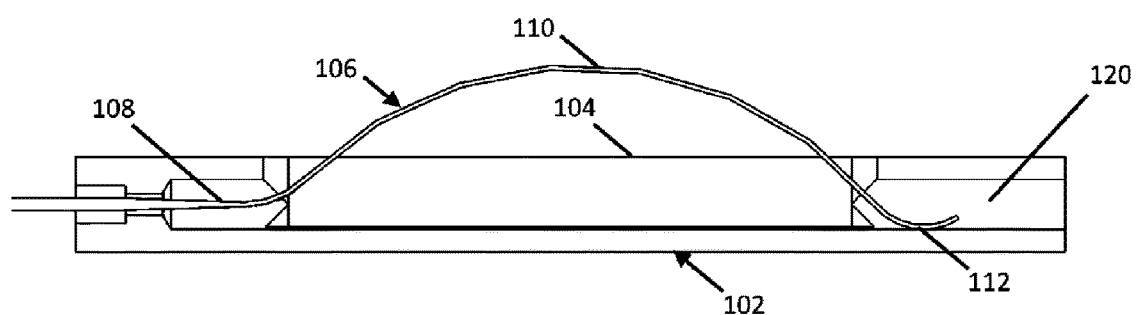
FIGS. 2A-2B are cross-sectional side views of a portion of the catheter of FIG. 1A, showing the electrode in extended (FIG. 2A) and low-profile (FIG. 2B) configurations.
Figure 2B:
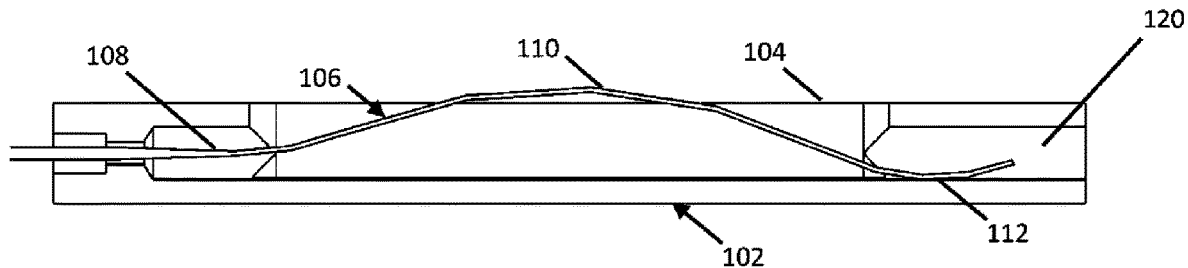

FIGS. 2A-2B illustrate detailed cross-sectional side views of the electrode (106) in various states of extension and recession with respect to a catheter housing (102). FIG. 2A illustrates the electrode (106) in an extended configuration. In the extended configuration, the intermediate portion (110) of the electrode (106) extends out of the opening (104) in the housing (102), and is thus extended radially away from the housing (102). FIG. 2B illustrates the electrode (106) in a low-profile or recessed configuration. In the low-profile configuration, the intermediate portion (110) of the electrode (106) is recessed into the opening (104). As shown, a small portion of the intermediate portion (110) of the electrode (106) may extend slightly radially beyond the outer radius of the catheter housing (102), but in other variations the intermediate portion (110) of the electrode (106) may be flush with or below the outer radius of the catheter housing (102). In the low-profile recessed configuration, the electrode (106) may be able to be atraumatically advanced through vasculature for positioning for fistula formation. It should be appreciated that in the variation shown in FIGS. 2A-2B, the proximal end (108) of the electrode (106) remains fixed relative to the catheter housing (102) regardless of the position of the intermediate portion (110) and the distal end (112) of the electrode (106).

In some variations, the electrode (106) may be biased toward the extended configuration from the low-profile configuration. That is, the electrode (106) may be configured to self-expand from the low-profile configuration toward the extended configuration. Put yet another way, the electrode (106) may be in its natural resting state in the extended configuration, with the intermediate portion (110) of the electrode (106) extending through the opening (104) in the catheter housing (102) at a predetermined distance away from the outer surface of the catheter housing (102). In these variations, a force may be required to hold the electrode (106) in the low-profile configuration. Such a force may be, for example, an external radially inward force applied to the intermediate portion (110) of the electrode (106), or a longitudinal force applied to an end of the electrode (e.g., a distal end (112) of the electrode (106) configured to slide proximally and distally within a lumen of the catheter). When an external force is no longer applied to the intermediate portion (110) of the electrode (106), the electrode (106) may return to the extended configuration such as shown in FIG. 2A and thereby allow the catheter to be compact. This design may obviate the need for a complex and/or bulky electrode actuation mechanism.

For example, the electrode (106) may be held in the low-profile configuration due to external radially inward force applied by one or more of a vessel wall (not shown for clarity), second catheter, sheath, or other object that may compress the intermediate portion (110) of the electrode (106) into the opening (104). Such a force may also cause the distal end (112) of the electrode (106) to slide longitudinally within the housing (102). For example, in some variations, when the catheter (100) is delivered through vasculature to a target location, the intermediate portion (110) of the electrode (106) may contact the interior surface of a vessel wall. The interior surface of the vessel wall may exert a radially inward force on the intermediate portion (110) of the electrode (106) that forces the electrode (106) into a low-profile recessed configuration in which the electrode (106) is recessed into the opening (104) while the electrode (106) contacts and advances through the vessel. The distal end (112) of the electrode (106) may slide distally within the lumen (120) as the intermediate portion (110) of the electrode (106) recesses into the opening (104). As shown, the electrode (106) may comprise a leaf spring—that is, an electrode formed from a curved slat or ribbon having a curvature configured to flex when an external force is applied against it.

That is, as the electrode (106) of a catheter (100) is advanced through a vessel, the electrode (106) may extend into and out of the opening (104) based on the force encountered. Accordingly, trauma to tissue may be reduced as the electrode (106) is advanced through a blood vessel. For instance, the electrode (106) may be in the recessed configuration while the electrode (106) contacts and advances through a vessel. In the recessed configuration, the electrode (106) may be compressed such that substantially the entire electrode (106) is within the opening (104). The compressed electrode (106) may store energy that allows the electrode (106) to automatically return to its natural extended configuration once the external force is removed. In some variations, a small diameter vessel may compress the electrode (106) into the opening (104) while a large diameter vessel may allow the electrode (106) to extend away from the housing (102) before contacting a vessel wall.

The bias of the electrode (106) toward the extended configuration may increase the energy efficiency of fistula formation by applying energy to tissue to be ablated rather than to fluid in the vessel. In some variations, when a leaf spring electrode, as described herein, is energized and tissue is ablated, the electrode may extend further from the opening by virtue of its spring force to maintain continuous contact with tissue. In this way, the electrode may naturally conform to the size of the vessel encountered and may eliminate the need for a user-actuated mechanism to deploy and/or extend the electrode from the housing, while still allowing the catheter comprising the electrode to be atraumatically delivered through vasculature. Put another way, rather than the catheter comprising a user-actuated control that in a first state holds the electrode in an atraumatic position for delivery through the vasculature and in a second state that allows the electrode to enter a configuration for tissue ablation, in some variations described herein the catheter may not comprise such a user-actuated control. Although the electrode may be moveable between low-profile and extended configurations, this movement may occur as a natural result of the bias of the electrode in combination with external forces (such as from a vessel wall and/or tubular body), and the electrode remains in a single state throughout use. That is, during both delivery and tissue ablation, the catheter is in a state in which the electrode would be able to be in the extended configuration, in the absence of a force external to the catheter (e.g., from a vessel wall) pressing on the electrode. Put yet another way, in these catheters described herein, the electrode need not be released or deployed from a delivery configuration by the user prior to fistula formation. As such, variations of the electrode as described herein may improve usability by reducing the number of steps and complexity of catheter operation, increase catheter reliability by reducing the number of internal moving parts, and simplify catheter manufacturing by reducing the component count.

In some variations, an ablation surface of the electrode may optionally be temporarily covered (e.g., by a sheath or tubing) such that the electrode will not contact tissue and/or other components as it is advanced through one or more vessels. In these instances, the temporary covering may be moved, removed, or reciprocated to expose the ablation surface to the surrounding environment. The covering may slide longitudinally along an outer surface of the catheter and hold the electrode in a low-profile configuration. In some variations, a temporary covering disposed over a catheter may aid advancement of the catheter through an access site (e.g., a hemostasis valve) without damage to either the catheter or access site. For example, a sheath slidably located on a catheter may be configured such that as the catheter is introduced through a hemostasis valve and into the vasculature, the distal end of the sheath protects the electrode from contacting the valve. In this manner, the electrode in a low-profile configuration may be covered by the sheath to protect the electrode from transitioning into the extended configuration and catching on the valve as it is advanced into a patient. In other variations, the configuration of the electrode as described herein may aid in temporarily covering and/or packaging a catheter assembly, as the electrode and housing may advance as easily through a tubular body (e.g., packaging) as it does in a blood vessel.

Figure 3A:
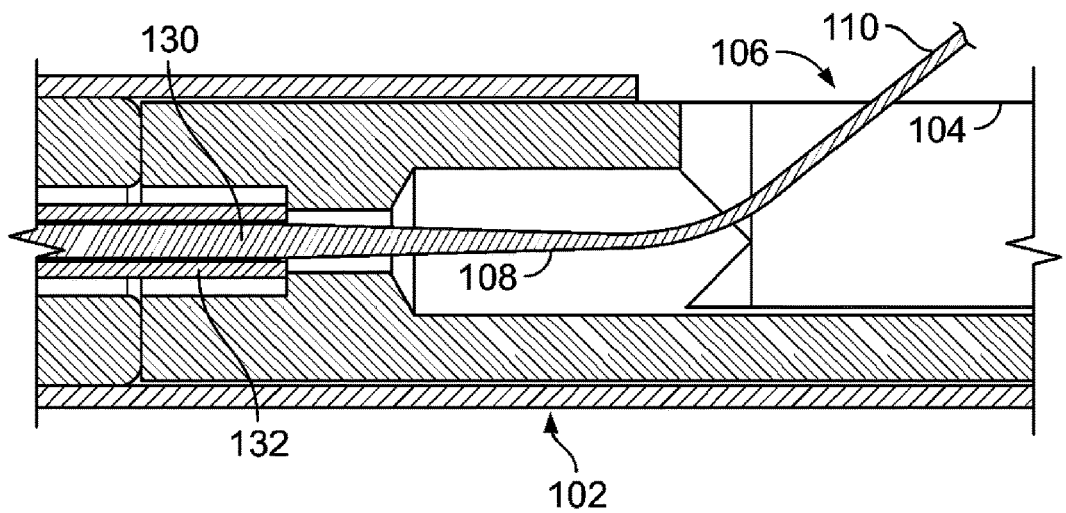
FIGS. 3A-3C are cross-sectional side views (FIG. 3A) and cross-sectional perspective views (FIGS. 3B-3C) of portions of the housing and electrode of the catheter of FIG. 1A.
Figure 3B:
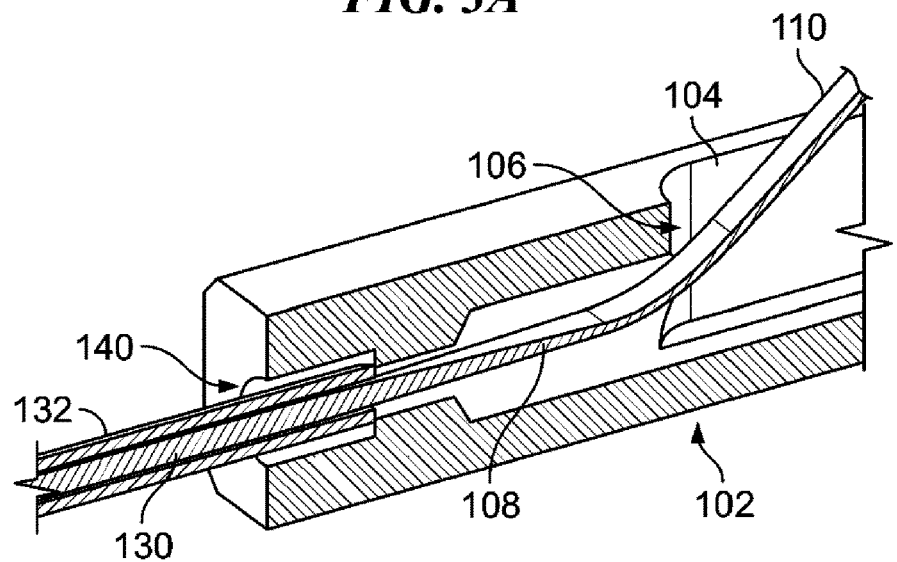
Figure 3C:
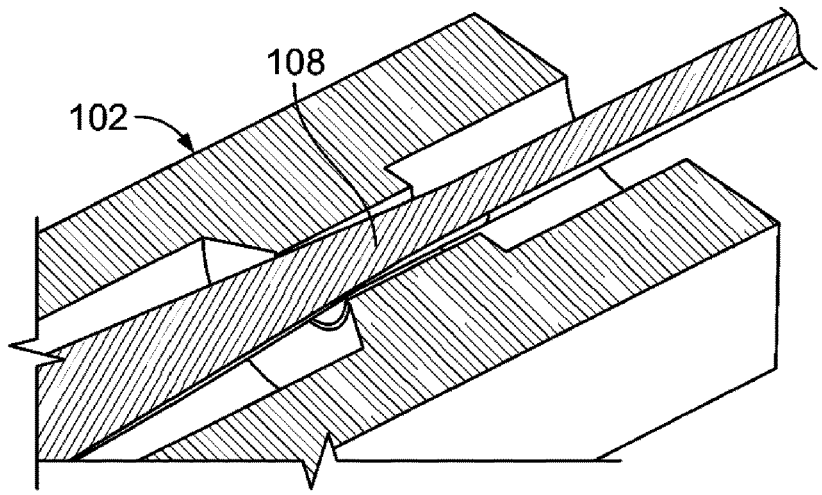

FIGS. 3A-3C are detailed depictions of the proximal end (108) of the electrode (106) at its point of fixation to the catheter housing (102). An electrical lead (130) may be coupled to the proximal end (108) of the electrode (106). Lead insulation (132) may cover electrical lead (130). A proximal end of the electrical lead (130) may be coupled to an energy source such as a radiofrequency current generator, as discussed in detail herein, to protect against the heat generated when the electrode (106) is activated. The proximal end (108) of the electrode (106) may be fixed to the catheter housing (102) in any suitable manner. For example, FIG. 3B illustrates an adhesive (140) applied between the proximal end (108) of the electrode (106), the lead (130), insulation (132), and the housing (102). The adhesive (140) may protect the insulation (132) from heat and/or plasma generated from fluid in the opening (104), securely fix the electrode (106) relative to the housing (102), and/or prevent fluid ingress from the opening (104) into other portions of the catheter. In other variations, the proximal end (108) of the electrode (106) may be mechanically fixed to the housing (102). FIG. 3C provides a cross-sectional perspective view of the proximal end (108) of the electrode (106) reducing in width (e.g., tapering) through the housing (102) to further secure and fix the proximal end (108) of the electrode (106) to the housing (102). In some variations, the opening (104) may form a reservoir for fluid to fill. When the electrode (106) is in an extended configuration, fluid may enter and be held in a reservoir underneath an outer surface of the electrode (106) and be relatively undisturbed by fluid flow around the catheter such as blood flow through the vessel. As discussed in further detail herein, the electrode (106) may be configured to generate plasma from the fluid in the reservoir. The proximal end (108) of the electrode (106) may be sealed from any fluid ingress from the reservoir such as through adhesive (140).

Figure 4:
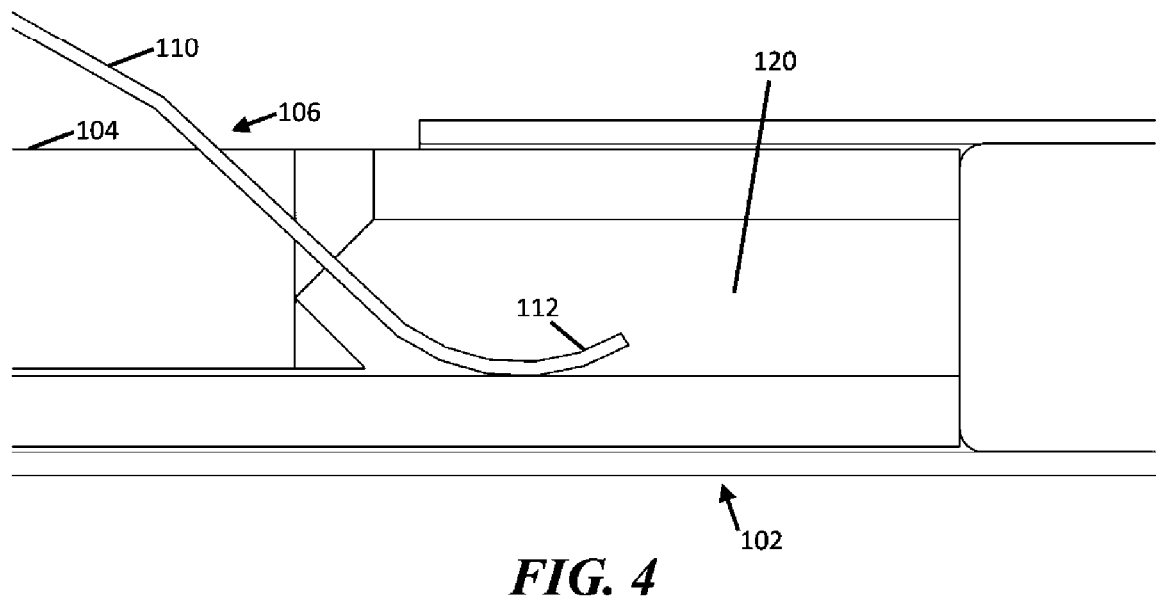
FIG. 4 is a cross-sectional side view of a portion of the housing and electrode of the catheter of FIG. 1A.

In variations in which the distal end of the electrode is configured to slide within the catheter in order to transition the electrode between low-profile and extended configurations, the distal end of the electrode may comprise one or more features that allow it to move smoothly within the catheter. The distal end of the electrode may move longitudinally between a first, proximal position when the electrode is in an extended configuration and a second, distal position when the electrode is in a low-profile configuration. For example, as shown in most clearly in FIG. 4, the distal end (112) of the electrode (106) may comprise a shape, such as a bend and/or an upturned shape. The distal end (112) of the electrode (106) may be shaped to promote smooth sliding of the distal end (112) of the electrode (106) within the lumen (120) of the housing (102) without catching or snagging. In the variation shown, the distal end (112) of the electrode (106) is curved, such that the curve moves along the wall of the lumen (120), rather than the tip of the distal end of the electrode (106) contacting the wall of the lumen (120). In other variations, the distal end (112) of the electrode (106) may have other configurations in order to allow for smooth translation within the lumen. For example, the distal end (112) of the electrode (106) and/or a wall of the lumen (120) may comprise a lubricating coating. The lumen (120) of the electrode (106) may extend distally from the opening (104) and have a length configured to accommodate a full distal extension of the distal end (112) of the electrode (106) when in a low-profile configuration (i.e., the intermediate portion (110) of the electrode (106) is recessed within the opening (104)).

Figure 5:
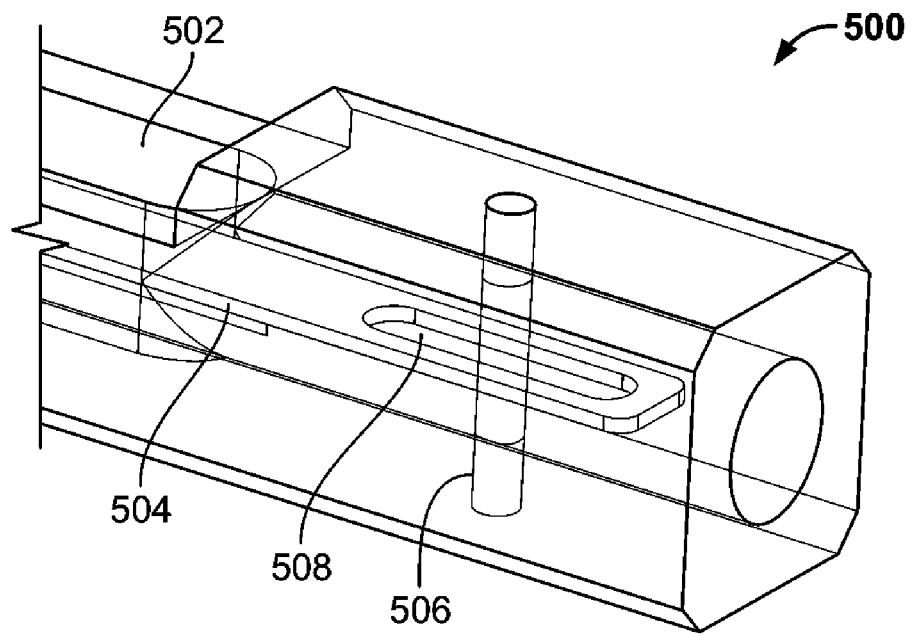
FIG. 5 is a perspective view of a portion of another variation of a catheter housing and electrode.

While a catheter may comprise an electrode having a fixed proximal end and a movable distal end, it should be appreciated that in some variations, one or more ends of the electrode may be partially fixed, such that the end may translate within a fixed range of motion. FIG. 5 is a detailed perspective view of a variation of a distal end of an electrode (504) having a distal end with a fixed range of motion. Shown there is a portion of a catheter housing (500) having an opening (502) through which the electrode (504) may extend in the extended configuration. The distal end of the electrode (504) is coupled to an anchor (506) via an elongate fenestration (508). As shown in FIG. 5, the anchor (506) may comprise a pin fixedly attached to a distal end of the housing (500). The distal end of the electrode (504) may be longitudinally slidable to move the elongate fenestration (508) of the electrode (504) relative to the anchor (506), such that the fenestration (508) moves between a first position with the anchor at its proximal end and a second position with the anchor at its distal end. The anchor (506) may serve as an axial catch structure to prevent the distal end of the electrode (504) from detaching from the housing (500) and passing through the housing opening (502).

Figure 6A:
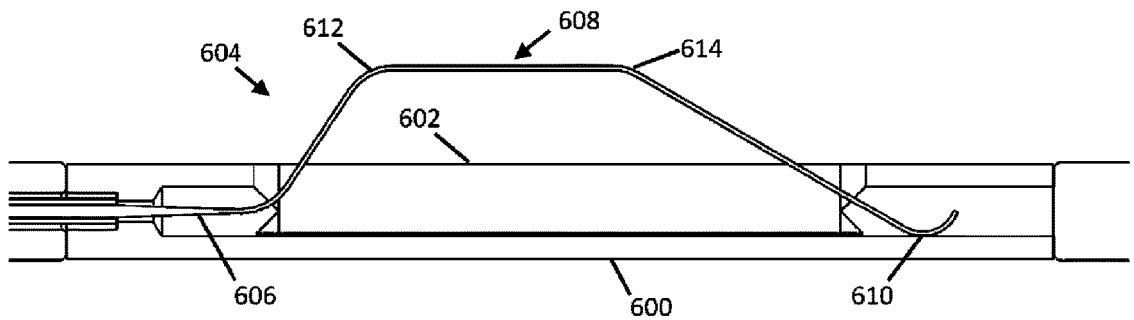
FIGS. 6A-6B are cross-sectional side views of portions of other variations of catheters comprising bent electrodes.

While in some variations, such as electrode (106) described herein, an intermediate portion (110) of the electrode (106) may have a curved shape throughout, in other variations, the intermediate portion of the electrode may comprise one or more discrete bends that allow the electrode to extend and recess into a housing. For example, FIG. 6A shows a cross-sectional side view of portion of a catheter comprising a housing (600) and electrode (604), where the electrode (604) comprises a proximal end (606), an intermediate portion (608) comprising a first bend (612) and a second bend (614), and a distal end (610). The first and second bends (612, 614) may have the same or different angles. As shown, the first bend (612) may be a smaller angle than the second bend (614). In some variations, a leading angle of the intermediate portion (608) of the electrode (604) (e.g., angle of the second bend (614)) may be maintained at about less than a 40 degree angle with respect to a longitudinal axis of the electrode (604) into the housing (602) when the electrode (604) transitions between a low-profile configuration and an extended configuration. In some of these variations, the first bend (612) may flatten as the electrode (604) transitions from the extended configuration (as shown in FIG. 6A) to the low-profile configuration. The housing (600) may comprise an opening (602), into which the electrode (604) may recess in the low-profile configuration. In the low-profile configuration, a distal end (610) of the electrode (604) may move smoothly through a lumen of the housing (600). In some of these variations, the second bend (614) of the electrode (604) may flatten to a lesser extent than the first bend (612) of the electrode (604).

Figure 6B:
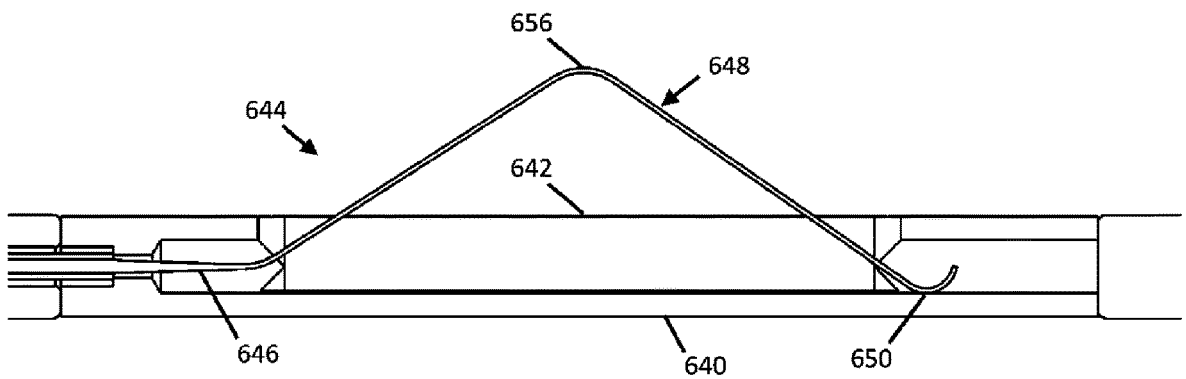

FIG. 6B shows a cross-sectional side view of another exemplary electrode (644) comprising a proximal end (646), an intermediate portion (648), and a distal end (650), where the intermediate portion (650) of the electrode (644) comprises a single bend (656). The catheter housing (640) may comprise an opening (642), into which the electrode (644) may recess in the low-profile configuration. In some variations, the bend (656) may flatten as the electrode (644) transitions from the extended configuration (as shown in FIG. 6B) to the low-profile configuration. As shown in FIG. 6B, the bend (656) may be located substantially in the center between the proximal end (646) and distal end (650) of the electrode (644). In the low-profile configuration, a distal end (650) of the electrode (644) may move smoothly through a lumen of the housing (640). It should be appreciated that the bend (656) may be located at a suitable location along the intermediate portion (650) of the electrode (644) such as closer to a proximal end (646) or distal end (650) of the electrode (644).

Figure 6C:
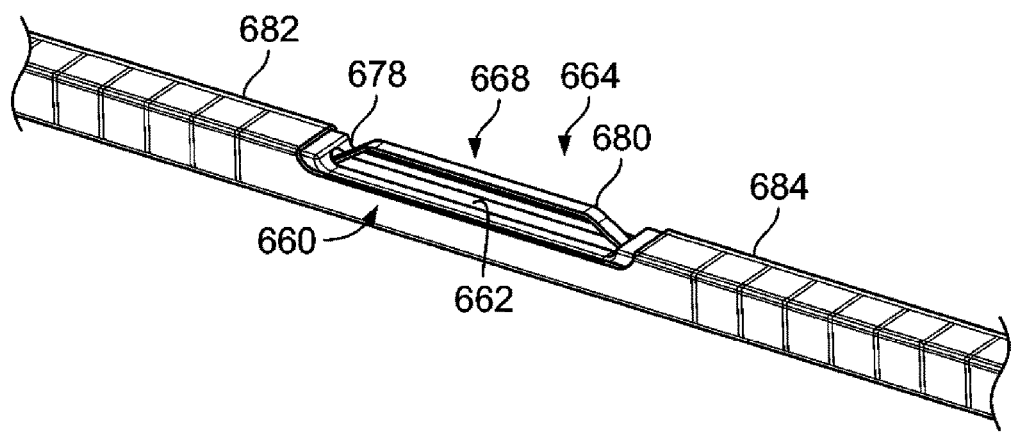
FIG. 6C is a perspective view of a portion of another variation of a catheter comprising a bent electrode.

FIG. 6C is a perspective view of another variation of a bent electrode. The electrode (668) includes a first bend (678) and a second bend (680), where the angles of the first bend (678) and second bend (680) are approximately equal and the portion of the electrode (668) between the first and second bends (678, 680) is substantially parallel to a longitudinal axis of the catheter. When the electrode (668) is in a low-profile configuration, it may recess into the opening (662) of the catheter housing (660). In some variations, the first and second bends (678, 680) may flatten as the electrode (668) transitions from the extended configuration (as shown in FIG. 6C) to the low-profile configuration. The first bend (678) may be located closer to a proximal end of the electrode (668) and the second bend (680) may be located closer to a distal end of the electrode (668). The distance between the first and second bend (678, 680) may correspond to an electrode ablation surface and a length of a fistula formed by the electrode (668). The catheter housing (660) may further comprise a first portion of a coaption region (682) and a second portion of the coaption region (684) with the opening (662) therebetween. The coaption region may aid in the visualization and positioning of one or more catheters relative to each other and their corresponding blood vessels, as will be discussed in more detail herein.

It should be appreciated that an electrode is not limited to one or two bends, and an intermediate portion of the electrode may comprise a plurality of bends. In general, the shape of the electrode may be configured to allow the electrode to extend to a maximum extended configuration (i.e., radially away from the outer surface of the catheter) while also being able to recess fully into a low-profile configuration (i.e., into an opening in the catheter housing, such that the outer surface of the electrode is flush with or below the outer surface of the catheter) without permanently deforming (e.g., retaining its shape memory) and configured to withstand proximal to distal and distal to proximal insertion into a tubular body (e.g., movement of the catheter proximally or distally within a vessel) without decoupling the electrode from the catheter.

The electrodes discussed herein may be made from any suitable material or combination of materials. In some variations the electrode may comprise one or more refractory metals. For example, an electrode may comprise tungsten, molybdenum, niobium, tantalum, rhenium, combinations or alloys thereof.

While the catheters shown in FIGS. 1A-6C have a single electrode, a catheter may have any suitable number (e.g., zero, one, two, three, or four or more) and combinations of the electrodes as described herein. The electrodes may be located in or on any suitable portion of the catheter (e.g., a distal end, an intermediate portion, or combinations thereof). In variations in which a catheter comprises two or more electrodes, multiple electrodes may be used to create multiple fistulas, either simultaneously or sequentially. In other variations, multiple electrodes may interact to form a single fistula.

2. Fixed Height Electrode

Figure 7A:
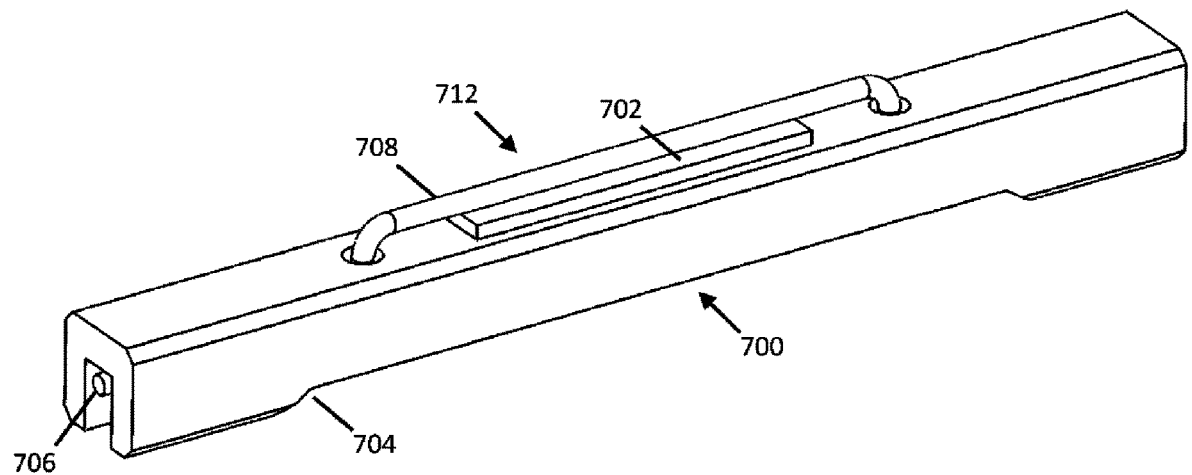
FIGS. 7A-7B are depictions of a portion of another variation of the catheter comprising a fixed electrode.
Figure 7B:
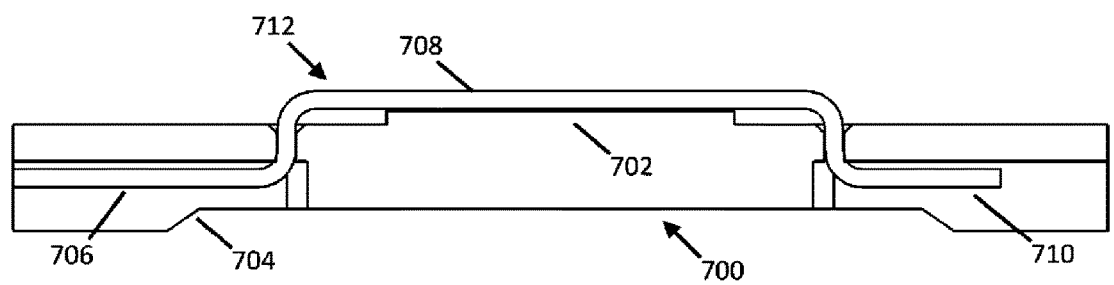

It should be appreciated that in other variations, the fistula-forming elements described herein need not extend into and out of an opening in a catheter housing. In some variations, the devices described herein may include a fixed or static electrode. FIGS. 7A-7B are illustrative depictions of a portion of a catheter comprising a fixed electrode. As shown, the catheter may comprise a fixed electrode (712). At least a portion of the electrode (712) may extend radially away from the outer surface of the catheter housing (700), such that it can contact or press into tissue to be ablated. In the variation shown, the electrode (712) may comprise a wire having proximal end (706) attached to the catheter, a distal end (710) attached to the catheter, and an intermediate portion (708) between the proximal and distal ends that is at a fixed distance away from the outer surface of the catheter.

In some variations of catheters comprising a fixed electrode, a portion of the electrode may be supported by a protrusion of a catheter. For example, housing (700) may comprise a protrusion (702) that protrudes from the housing (700) by a predetermined amount to support an intermediate portion (708) of the electrode (712). In some variations, the protrusion (702) may extend by up to about 3 mm from the housing (700). The intermediate portion (708) of the electrode (712) may sit on the protrusion (702). The protrusion (702) may prevent the electrode (708) from deforming under compression. In some variations, on the side of the catheter opposing the protrusion (702) and intermediate portion (708), the housing (700) may comprise a recess (704) to maintain an approximately consistent cross-sectional diameter of the catheter along a length of the housing (700). For instance, the depth of the recess (704) may correspond to a height of the protrusion (702). This may help, for example, the entire catheter to pass through an introducer sheath. In some variations, the recess (704) may be electrically insulated via epoxy.

3. Shape

The size, shape, and orientation of an electrode used to form a fistula may determine the size or other characteristics of the fistula, including the fistula resistance and flow rate. The electrode ablation surface may have any shape or size suitable for ablating tissue and forming a fistula of a desired size and shape. For example, an electrode ablation surface of greater width may generate a wider fistula aperture, resulting in decreased fistula resistance and improved flow. The shape of the electrode may in some instances be selected to promote wound healing, as well as to prevent undesirable fistula dilation and other complications. In some variations, a desired electrode shape having a desired width may be etched and then formed into a leaf spring. In some variations, a secondary electrode shape may be welded to an electrode to provide a desired shape and width to a formed fistula.

In some variations, a portion of an electrode may comprise a rolled portion of material (e.g., a flattened ribbon) configured to contact tissue for fistula formation, while a different portion of the electrode may comprise an unrolled portion (e.g., a round wire). The rolled portion may be flattened relative to the unrolled portion. For example, returning to FIG. 1B, the intermediate portion (110) and distal end (112) of the electrode (106) may comprise a rolled portion of material (e.g., flattened ribbon) while the proximal end (108) of the electrode (106) may comprise an unrolled portion. In some variations, the proximal end (108) of the electrode (106) may comprise a transition from the unrolled portion to the rolled portion. The distal end (112) of the electrode (106) may optionally comprise a transition from rolled material to unrolled material (not shown). Similarly, while the electrode (912) in FIGS. 7A-7B is shown as an unrolled wire, it should be appreciated that in some variations all or a portion of the electrode (712) may be rolled.

Figure 8:
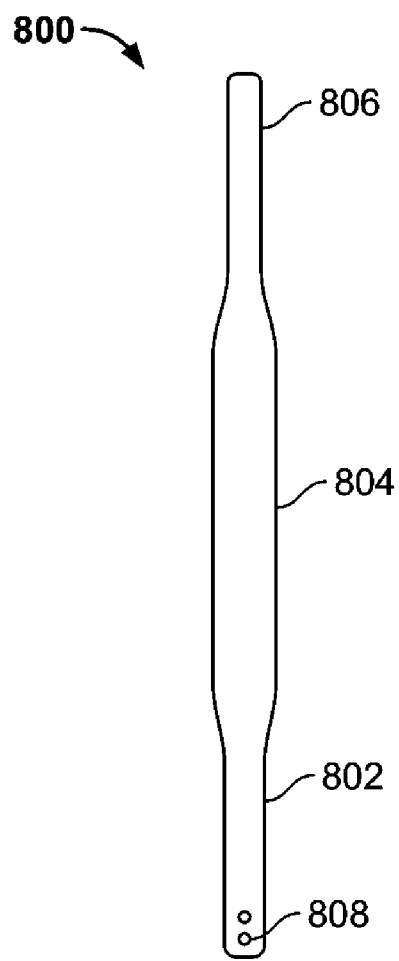
FIG. 8 is a plan view of another variation of an electrode.

FIG. 8 is a plan view of a variation of a rolled portion of an electrode (800). As shown there, the rolled portion of the electrode (800) comprises a proximal end (802), an intermediate portion (804), and a distal end (806). In some variations, a proximal end (802) may comprise a fixing portion (808) to fix the proximal end (802) relative to a catheter housing (not shown). The rolled portion of the electrode (800) may comprise a flat ribbon shape. The electrode (800) may vary in width along its length where, for example, an intermediate portion (804) is wider than a proximal end (802) and/or a distal end (806). The intermediate portion (804) of wider width may correspond to an ablation surface that contacts and ablates tissue. The electrode may comprise, for example, a ribbon of tungsten or tungsten rhenium formed in a leaf spring configuration. In some variations, the intermediate portion of an electrode may be formed with one or more shapes to aid in forming fistulas having a predetermined configuration. For example, a secondary electrode, such as those illustrated in FIGS. 9A-9P may be welded to an intermediate portion (804) of the electrode (800).

Figure 9A:
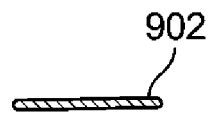
FIGS. 9A-9P are illustrative depictions of variations of electrode shapes.
Figure 9B:
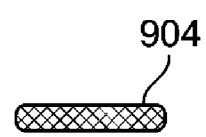
Figure 9C:
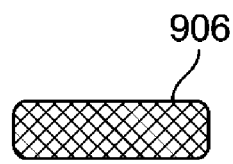
Figure 9D:
Figure 9E:
Figure 9F:
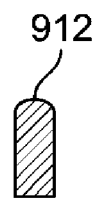
Figure 9G:
Figure 9H:
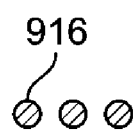
Figure 9I:
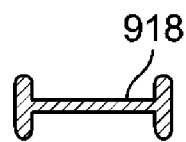
Figure 9J:
Figure 9K:
Figure 9L:
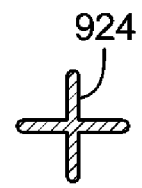
Figure 9M:
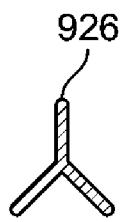
Figure 9N:
Figure 9O:
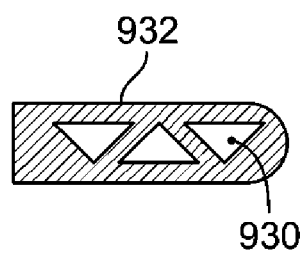
Figure 9P:
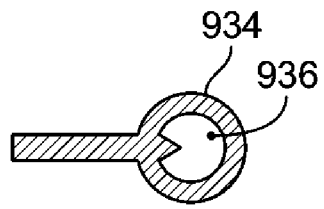

FIGS. 9A-9P illustrate exemplary variations of electrode shapes that may be desirable for fistula formation. Exemplary electrode shapes may include a longitudinally extending bar (902, 904, 906) shown in FIGS. 9A-9C, a laterally extending bar (908, 910, 912) shown in FIGS. 9D-9F, one or more circles (914, 916) shown in FIGS. 9G-9H, a dumbbell (918, 928) shown in FIGS. 9I, 9N, an asterisk (920) shown in FIG. 9J, a horseshoe (922) shown in FIG. 9K, a plus sign (924) shown in FIG. 9L, a Y-shape (926) shown in FIG. 9M. An exemplary electrode (932) having a plurality of triangular apertures (930) is shown in FIG. 9O. Another exemplary electrode (934) having a circular distal end and a semicircular aperture (936) is shown in FIG. 9P. These shapes may be provided on a surface of the fistula forming element on a side opposite a catheter opening.

In some of these variations, these shapes may be welded or formed on the electrode. For example, electrode shapes may be welded to an ablation surface of an electrode, such as an intermediate portion (804) of the flat ribbon electrode (800) of FIG. 8. FIG. 10A is an exemplary depiction of the electrode shape of FIG. 9L welded to the electrode depicted in FIG. 8. In particular, FIG. 10A illustrates a flat ribbon electrode (1000) having a plus shaped electrode (1002) welded thereon. In variations of systems described herein comprising first and second catheters both comprising an electrode, both electrodes may have the same shape. In others of these variations, an electrode of one catheter may be configured to nest with an electrode of the other catheter. In yet others of these variations, electrodes of both catheters may have similar shapes, but one electrode may be larger than the other. This may be desirable, for example, for making a larger opening in a first vessel (e.g., a vein) than in a second vessel (e.g., an artery). It should be noted that in some instances, fistula dilation may be reduced by forming a fistula in a circumferential direction of a blood vessel as opposed to an axial direction. For example, as shown in FIG. 10B, a shape may be welded or formed on an electrode having a lengthwise direction perpendicular to the longitudinal axis of the catheter. FIG. 10B is an exemplary depiction of the electrode shape of FIG. 9N welded to the electrode depicted in FIG. 8. In particular, FIG. 10B illustrates a flat ribbon electrode (1010) having a dumbbell shaped electrode (1012) welded thereon.

Figure 11A:
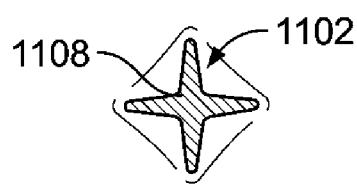
FIGS. 11A-11B are illustrative depictions of a fistula formed by an electrode having a shape as in FIG. 9L.
Figure 11B:
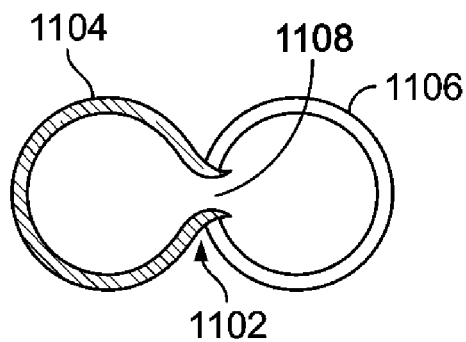
Figure 12A:
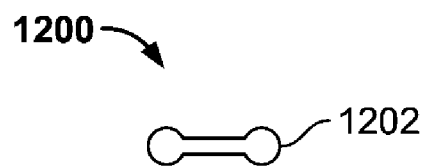
FIGS. 12A-12B illustrate side views of fistulas with strain relief ends.
Figure 12B:
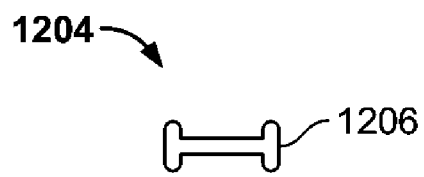

In some variations, the electrode shape may be configured to have beneficial effects. For instance, an electrode may be configured to form tissue flaps. These tissue flaps may facilitate neointimal generation through the extravascular space and may promote wound healing and reduce the likelihood of thrombosis. Exemplary electrode shapes that may form tissue flaps include an asterisk shape (920), plus shape (924), or Y-shape (926), as shown in FIGS. 9J, 9L, and 9M, respectively. For instance, FIG. 11A shows a side view of a fistula (1108) formed using an electrode having a plus shape, such as an electrode comprising the plus shape (924) shown in FIG. 9L. FIG. 11B shows a cross-sectional view of two vessels (1104, 1106) between which the fistula (1108) is formed. As shown in FIGS. 11A-11B, the fistula (1108) may form tissue flaps (1102). As shown in the cross-sectional view of FIG. 11B, the tissue flaps (1102) may fold over from the first vessel (1104) into the second vessel (1106) when a fistula (1108) is formed. As another example, the electrode shape may be configured to form a fistula with a shape configured to distribute fluid flow strain across a wider surface area to prevent undesirable fistula enlargement, dilation, or tearing due to arterial blood pressure. For example, FIG. 12A illustrates a side view of a fistula (1200) with strain relief ends (1202) formed by an electrode comprising a dumbbell shape with rounded ends as shown in FIG. 9N. FIG. 12B illustrates a side view of a fistula (1204) with strain relief ends (1206) formed by an electrode comprising a dumbbell shape with flat ends as shown in FIG. 9I.

A size (e.g., radius) and shape of tissue ablation created using a given electrode may depend not only on the size and shape of the electrode, but also on the energy delivered to the electrode and adjacent tissue and/or fluid. For example, a lower voltage may ablate tissue to form a cut that corresponds to the shape of the electrode, while a higher voltage may increase an ablation radius of the electrode, such that the ablated area is larger than the electrode. In some variations, energy may be applied such that the fistula does not exceed the dimensions of the electrode by more than about 0.1 mm.

In some variations, an electrode may have one or more apertures or recesses, such that energy applied to the electrode to ablate tissue may ablate an outer circumference of tissue while generally leaving intact one or more inner tissue portions within the outer circumference. In variations having recesses, the recesses may vary in height. After initial formation of the fistula with the electrode, blood flow through the fistula may naturally push the inner tissue portions out of the fistula. An exemplary electrode (932) having a plurality of triangular apertures (930) is shown in FIG. 9O. In some of these variations, it may be desirable that the aperture be about 0.07 mm or less in diameter to prevent the separated tissue released into the bloodstream from forming an embolism. In the electrode (934) shown in FIG. 9P, the aperture (936) may comprise asperities that may aid bubble formation and create electric field concentrations in the electrode, thereby increasing the local current densities and increasing localized resistive heating. This may speed up ablation by reducing a vapor generation time preceding plasma generation.

C. Single-Sided Electrode Systems

In the systems described herein comprising two catheters, each catheter may comprise a fistula-forming element, but need not. In some variations, only one catheter may comprise a fistula-forming element. In some of these instances, a second catheter that lacks a fistula-forming element may not directly ablate tissue, but may help align the catheters, bring the blood vessels into apposition, and/or otherwise improve formation of a fistula. Generally, in these variations, the second catheter may comprise a backstop configured to be positioned within a vessel such that the backstop opposes a fistula-forming element of the first catheter. The backstop of a second catheter may protrude from one side of the second catheter body. In some variations, the backstop may have a shape corresponding to a fistula-forming element of a first catheter to extend into the second catheter, which may in some instances increase an ablation surface and therefore a length of a fistula. For example, the backstop may comprise one or more concave or convex portions configured to be corresponding and complementary to the fistula-forming element of the first catheter. In some variations, the second catheter may comprise a recessed portion on the opposite side of the catheter body from the backstop. In some variations, a catheter comprising a protruding backstop may encounter difficulty passing through a tubular body such as an introducer sheath. A recessed portion may define a relief cut to accommodate passage of the catheter through a tubular body such as an introducer sheath. This may allow an approximate cross-sectional diameter of the catheter to be maintained through the region comprising the backstop. In this way, a catheter may be able to fit through a lumen of an introducer sheath and/or a blood vessel, since the diameter of a catheter may not exceed, even at the location of the backstop, a lumen diameter of an introducer sheath and/or blood vessel.

The backstop may be configured to compress tissue in a localized region for ablation by a fistula-forming element of a first catheter. Compressing tissue between a backstop and a fistula-forming element may reduce the required height or ablating reach of the fistula-forming element. The backstop may comprise any suitable nonconductive material. For example, the backstop may comprise a ceramic and/or polymeric material.

Figure 13A:
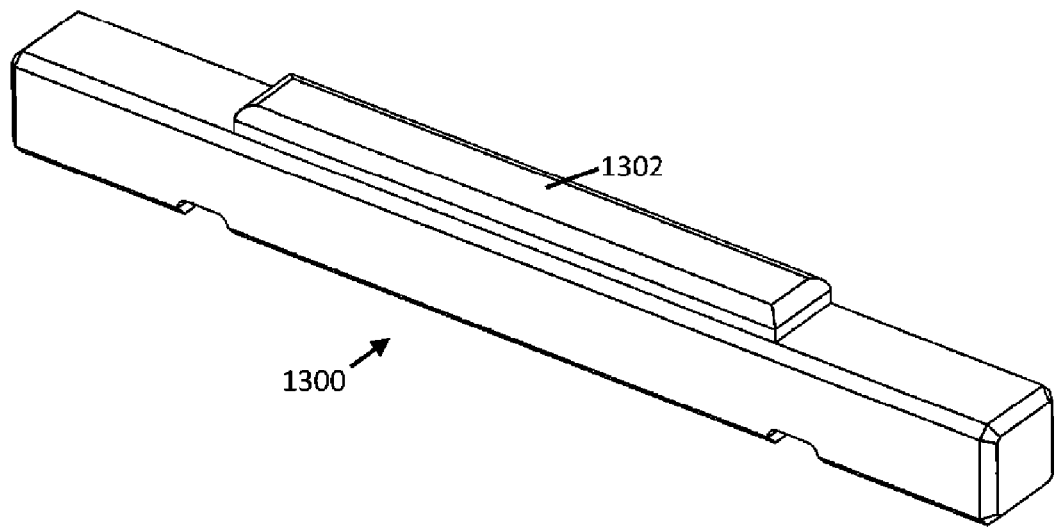
FIGS. 13A-13B depict portions of another variation of a system comprising a first catheter having an electrode and a second catheter having a backstop.
Figure 13B:
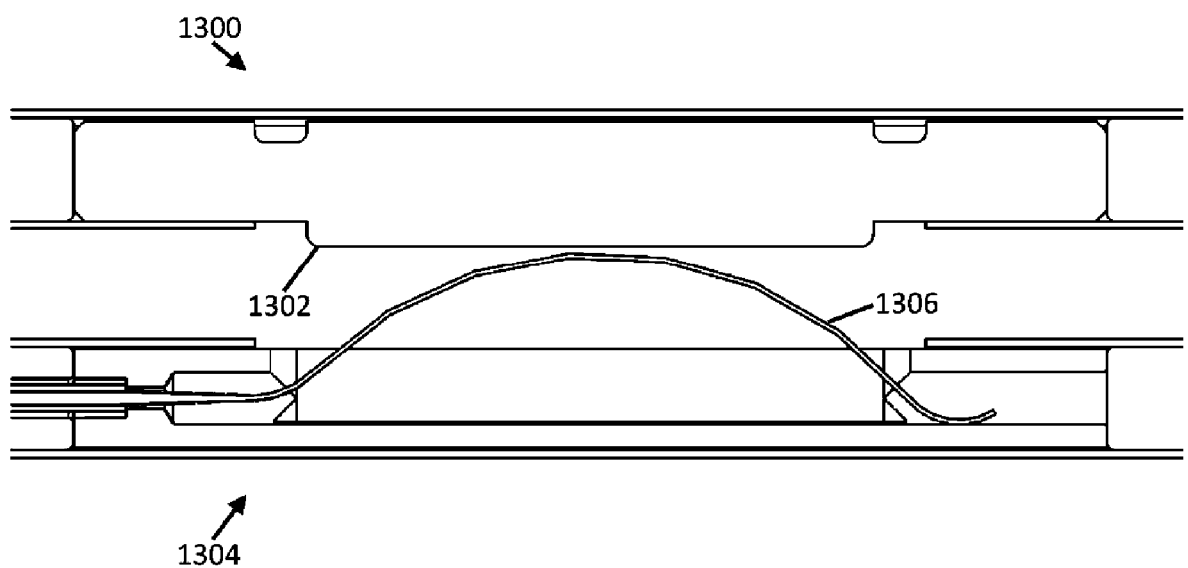

FIG. 13A depicts a portion of a second catheter comprising a protruding backstop (1302) having a flat surface protruding from a square second catheter (1300). FIG. 13B shows the backstop (1302) aligned with an electrode (1306) of a first catheter (1304). In use, after advancement of the first and second catheters into respective blood vessels (not shown), the catheter housings may be aligned as shown in FIG. 13B. The convex portion (1302) of the second catheter (1300) may oppose the electrode (1306) and compress tissue therebetween. As shown and discussed in more detail herein, the size and shape of a backstop may be varied based on factors including tissue thickness and density, as well as a desired fistula size, shape, and location.

Figure 14A:
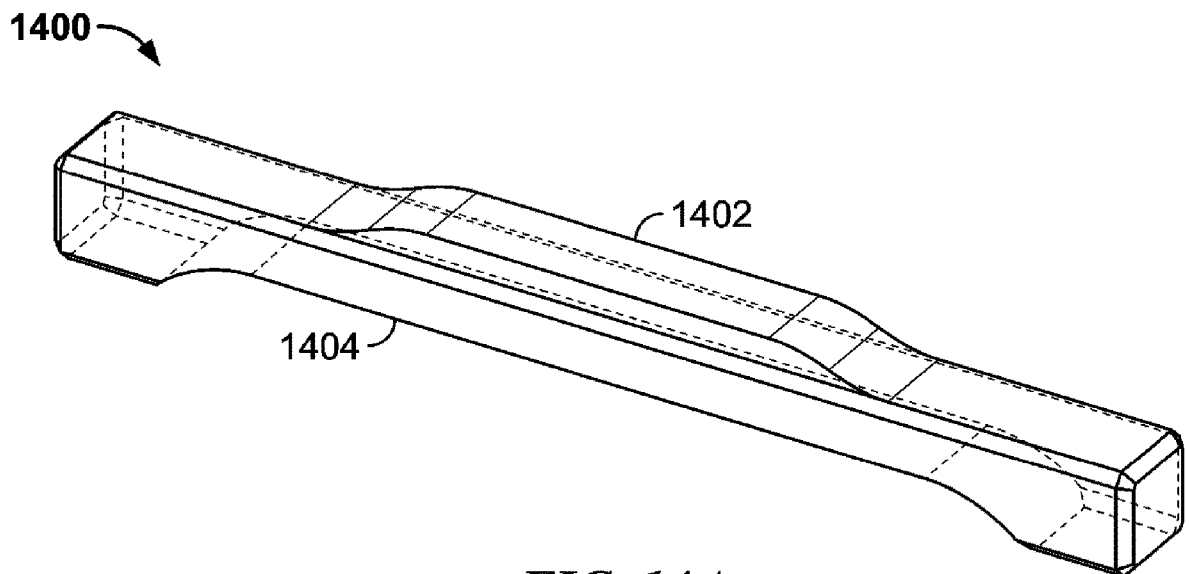
FIGS. 14A-14C depict portions of another variation of a system comprising a first catheter having an electrode and a second catheter having a backstop.
Figure 14B:
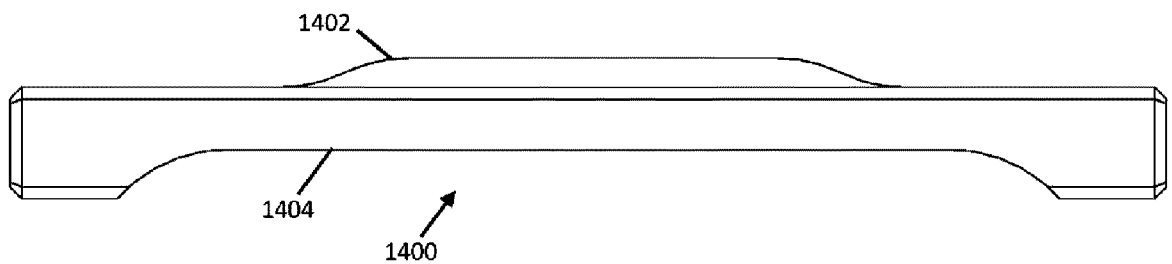
Figure 14C:
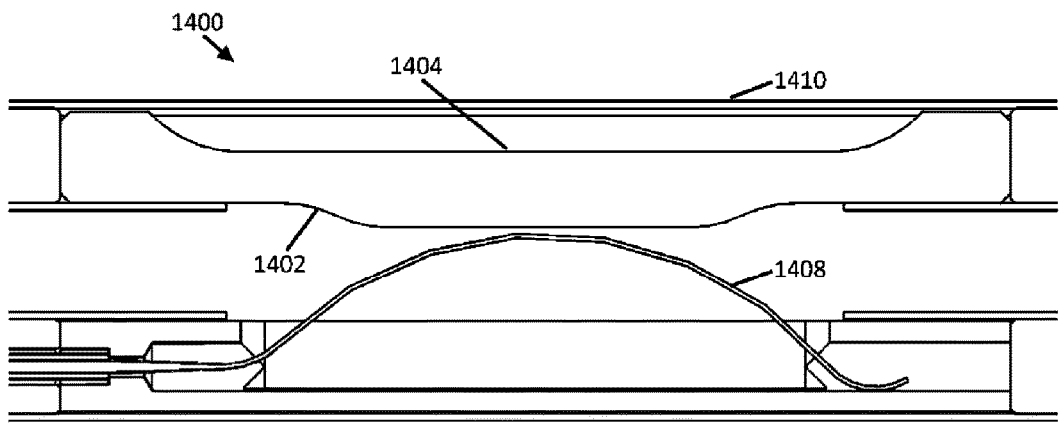

FIGS. 14A-14B show perspective and side views, respectively, of a portion of a second catheter (1400) comprising a protruding backstop (1402). Opposite the backstop (1402), the second catheter comprises a recessed portion (1404) having a complementary shape to the protruding backstop (1402). FIG. 14C shows a portion of the second catheter (1400) aligned with a portion of a first catheter (1406) comprising an electrode (1408). In some variations, the protruding backstops (1302, 1402) may aid ablation of thicker tissue by further compressing tissue against the electrode (1306, 1408).

Figure 15A:
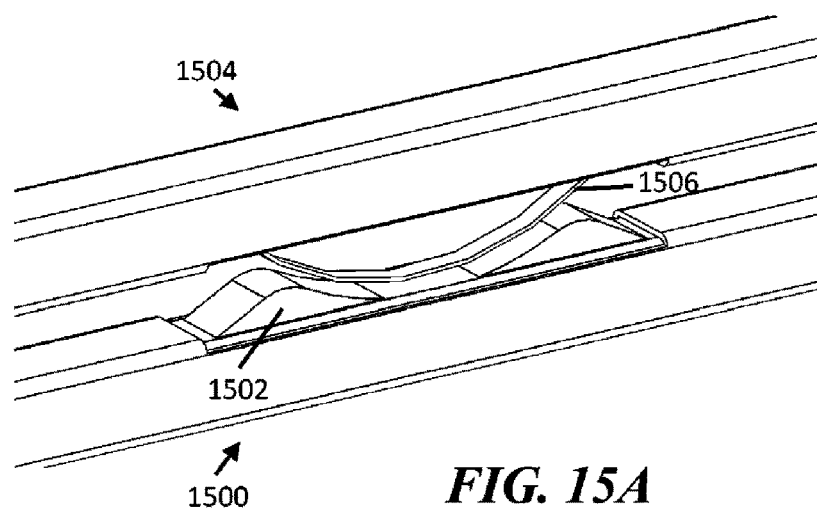
FIGS. 15A-15B depict perspective and cross-sectional side views, respectively, of a portion of another variation of a system comprising a first catheter having an electrode and a second catheter having a backstop.
Figure 15B:
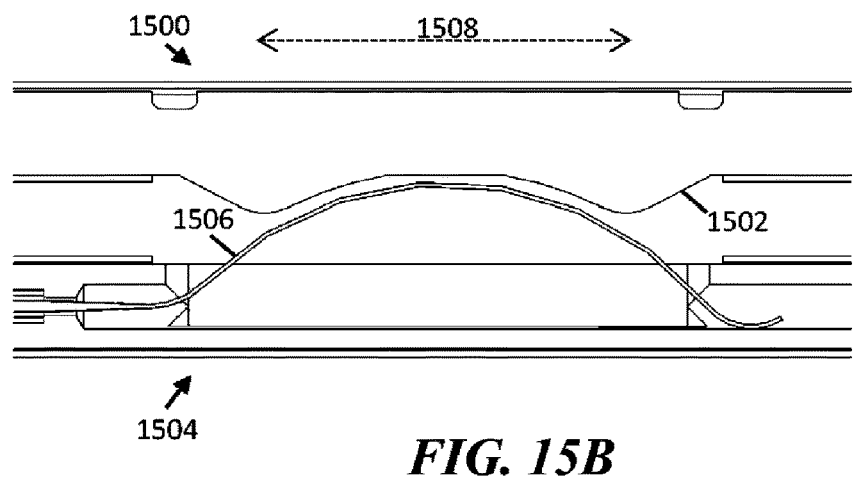

FIGS. 15A-15B depict a protruding backstop having a complementary shape to a corresponding electrode. A system is shown there comprising a first catheter (1504) comprising an electrode (1506) and a second catheter (1500) comprising a protruding backstop (1502). The backstop (1502) comprises a concave portion having a shape that is a corresponding and complementary (e.g., inverse, reciprocal) for matching or conforming to the electrode (1506) when the first and second catheters (1504, 1500) are aligned. As shown best in FIG. 15B, the shape of the concave portion of the backstop (1502) may correspond to a shape of the intermediate portion of the electrode (1506) in an extended configuration. As such, when the first and second catheters (1504, 1500) are located in adjacent vessels and properly aligned, the backstop (1502) may promote tissue compression between the backstop (1502) and the electrode (1506). While shown in FIGS. 15A-15B as comprising a concave curved portion, in other variations, a backstop may have any suitable shape based on the shape of an electrode, such as, for example, a complementary shape to the electrodes depicted in FIGS. 6A-6C. In some variations, such as shown in FIGS. 15A-15B, the lowest point of the concave portion may be approximately at the same height as the catheter body adjacent to the backstop. However, it should be appreciated that in other variations, the lowest point of the concave portion may be below the height of the catheter body adjacent to the back stop—i.e., in some variations the backstop may be partially protruding and partially recessed.

Figure 16:
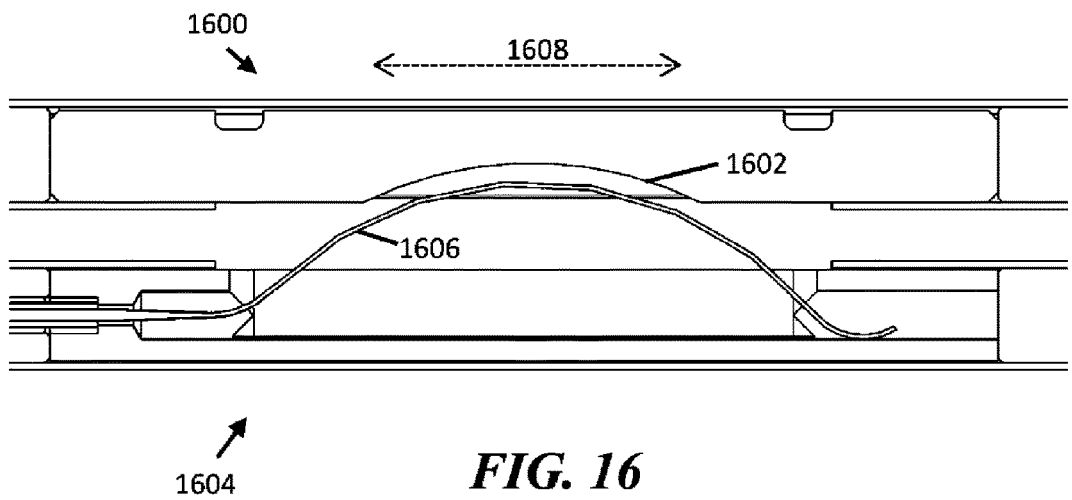
FIG. 16 is a cross-sectional side view of a portion of another variation of a system comprising a first catheter having an electrode and a second catheter having a backstop.

While FIGS. 13A-15B show backstops protruding from a second catheter, in other variations, the backstop may be recessed into the catheter, or the backstop may have some portions extending from and some portions recessed into the catheter. For example, FIG. 16 shows a catheter system comprising a catheter with a recessed backstop having a complementary shape to a portion of an electrode of another catheter. Shown there is a cross-sectional side view of a system comprising a first catheter (1604) comprising a curved electrode (1606) and a second catheter (1600) comprising a curved, concave recessed backstop (1602). The concave backstop (1602) may have a complementary (e.g., inverse, reciprocal) shape matching or conforming to a portion of the electrode (1606) of the first catheter (1604).

In variations of a system comprising a backstop having a complementary shape to a corresponding electrode (e.g., FIGS. 15A-16), a length of a fistula formed may be based on a length of the corresponding regions of the backstop and electrode, i.e., a compression region of the backstop. For example, in the variation of FIGS. 15A-15B, the fistula formed by the system may have a length corresponding to the peak-to-peak distance of a saddle shape formed by the backstop, shown in FIG. 15B as distance 1508. As another example, in the variation of FIG. 16, the fistula formed by the system may have a length corresponding to the end-to-end distance of the recess, shown in FIG. 16 as distance 1608.

Figure 17A:
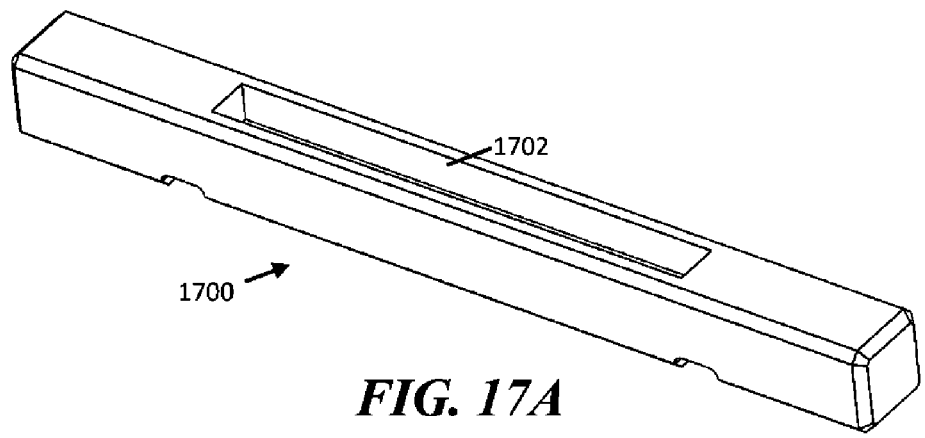
FIGS. 17A-17C depict portions of another variation of a system comprising a first catheter having an electrode and a second catheter having a backstop.
Figure 17B:
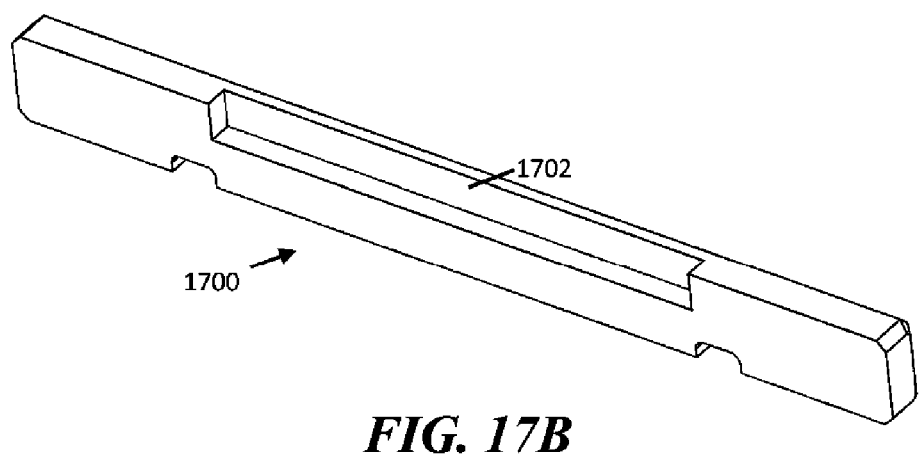
Figure 17C:
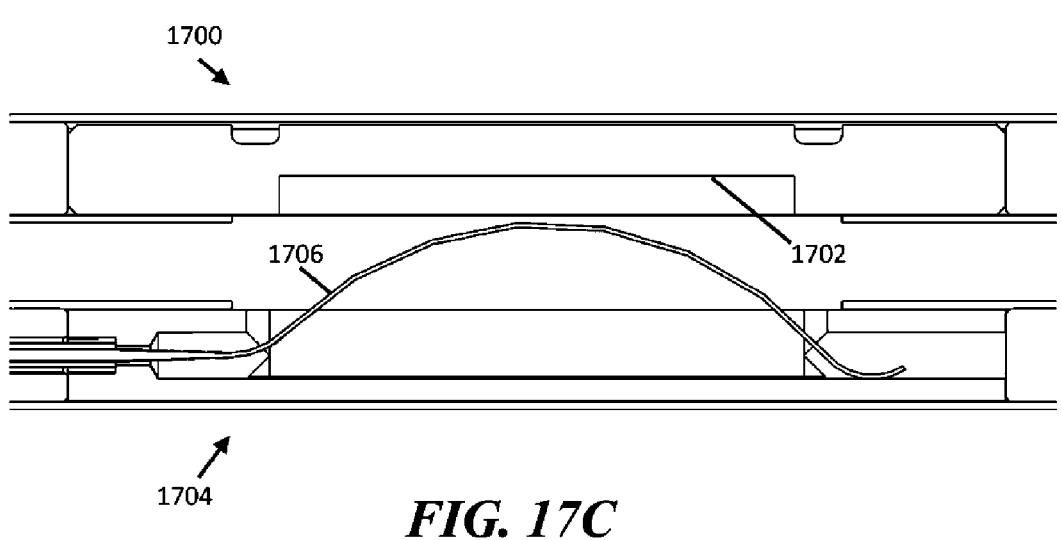

In other variations, second catheters described herein may comprise recessed backstops not having a complementary shape to the electrode of an opposing first catheter. For example, in some variations, a second catheter may comprise a rectangular recess configured to receive a portion of an electrode of an opposing first catheter during or after fistula formation. An exemplary recessed backstop (1702) is shown in perspective and cross-sectional views in FIGS. 17A and 17B, respectively. As shown there, the recess (1702) may comprise a rectangular recess (e.g., slot) to receive a portion an electrode. An exemplary system comprising the recessed backstop (1702) is shown in FIG. 17C, comprising a first catheter (1704) comprising a curved electrode (1706), and a second catheter (1700) comprising the rectangular recessed backstop (1702). The portion of the electrode (1706) radially furthest from the first catheter (1704) may fit into the rectangular recess. As such, the width of the slot may be configured to be at least the width of the electrode (1706).

Figure 18A:
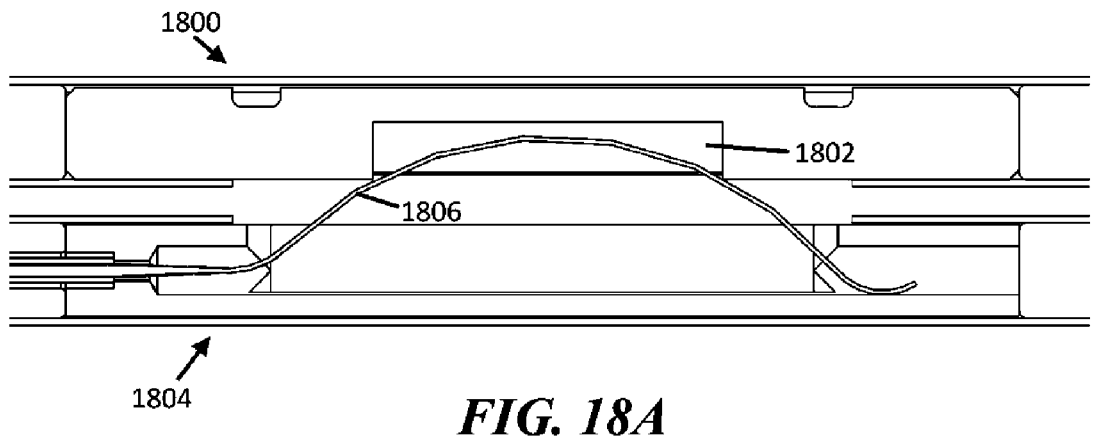
FIGS. 18A-18B are cross-sectional side views of portions of variations of systems comprising a first catheter having an electrode and a second catheter having a backstop.
Figure 18B:
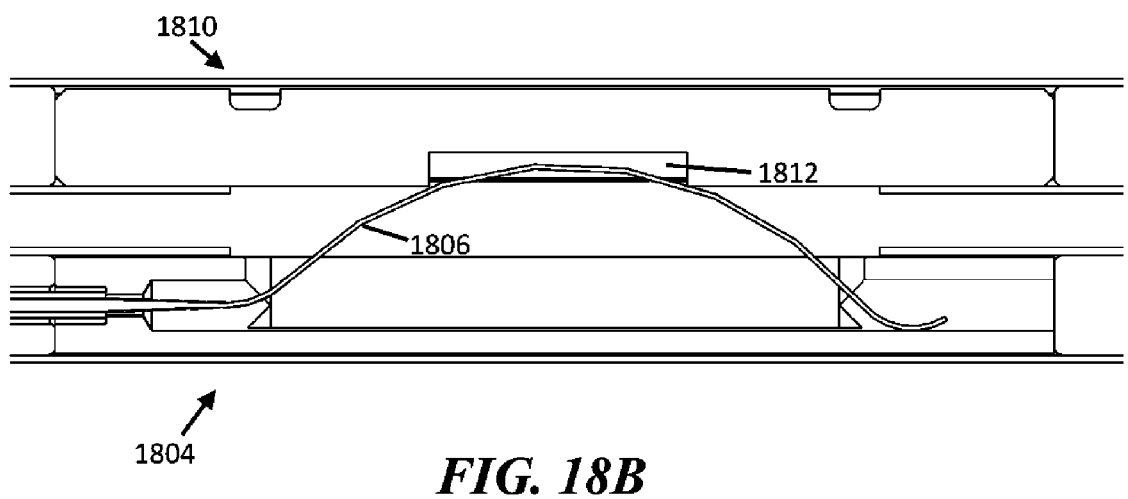

A rectangular recessed backstop may have any suitable length and depth. FIGS. 18A-18B are cross-sectional views of two systems comprising a first catheter with an electrode and a second catheter with a rectangular recessed backstop. FIG. 18A shows a variation comprising a first catheter (1804) comprising a curved electrode (1806), and a second catheter (1800) comprising a backstop comprising a rectangular recess (1802). FIG. 18B shows the first catheter (1804) of FIG. 18A with a different second catheter (1810). As shown there, the second catheter (1810) comprises a backstop comprising a rectangular recess (1812), where the rectangular recess (1812) is shorter and shallower than the rectangular recess (1802). As such, a smaller portion of the electrode (1806) is able to be received by the recess (1812) as compared to the recess (1802). This may result in formation of a smaller fistula when formed by delivering current from the electrode (1806). More generally, second catheters comprising backstops with recesses having different depths and/or lengths may allow for the generation of fistulas of different dimensions when using the same electrode. A deeper recess may allow a larger portion of the electrode to extend into the recess, thus increasing an ablation surface of the electrode. In some non-limiting variations, the backstop may be between about 2 mm and about 20 mm in length, and the recess may be between about 1 mm and about 10 mm in length. In one variation, the backstop may be about 10 mm in length.

In single-sided electrode systems, a first catheter comprising an electrode may be connected to a monopolar output of a current generator. In some variations, a single-sided electrode system may comprise one or more return electrodes (e.g., ground pads) that may be disposed on a skin of a patient and configured to allow current to pass from an active electrode of the first catheter through the patient and then to the return electrode. A conductive gel may be applied between the return electrode and the skin to improve contact.

D. Dual-Sided Electrode Systems

In other variations, the catheter systems described herein may be dual-sided catheter systems. A dual-sided catheter system may comprise first and second catheters each including one or more electrodes. In some variations, the dual-sided catheter systems may be dual-ablation catheter systems, wherein one or more electrodes on each of the two catheters delivers energy for ablating tissue at a fistula site from opposing sides such that the electrodes on each catheter are active electrodes and deliver current. In order to both deliver energy, both catheters may be connected to an active output of a current generator. A dual-ablating system may comprise one or more return electrodes (e.g., ground pads) that may be disposed on a skin of a patient and configured to allow current to pass from the active electrodes through the patient and then to the return electrode. A conductive gel may be applied between the return electrode and the skin to improve contact. A dual ablating system as described herein may have the ability to ablate through twice as much tissue in a predetermined amount of time as compared to a single-sided ablation system. The energy applied to tissue may also be distributed more evenly when delivered with a dual-ablation system. In other variations, the dual-sided catheter systems may be configured such that one or more electrodes on one of the two catheters deliver energy, wherein one or more electrodes on the second of the two catheters provides a return path.

FIGS. 19A-19D are illustrative depictions of a distal portion of a variation of a dual-sided catheter system comprises a first catheter (1900) and a second catheter (1910) comprising a respective first electrode (1902) and second electrode (1912). The electrodes (1902, 1912) may have a low-profile configuration and an extended configuration, and may be biased toward the extended configuration, as described in more detail herein. As shown in FIGS. 19A-19D, each electrode may comprise a curved wire configured to at least partially flatten in the low-profile configuration, as described in more detail herein. In some variations, each electrode may include, for example, a cantilevered leaf spring element that may deflect to recess into its respective housing and may extend outward once energized to ablate tissue and cut through tissue, similar to the other leaf spring electrodes described herein. The leaf spring may be thin enough such that if the electrodes abut against each other, the leaf spring will conform to a flat mating surface.

Fistula formation using two such catheters may be achieved in multiple ways, including, for example, in either monopolar or bipolar configurations. In some variations when both catheters are designed for monopolar energy delivery, current may be delivered by the first electrode (1902) at the same time as the second electrode (1912). In other variations, the first electrode (1902) may be an active electrode and the second electrode (1912) may be a return electrode, or vice versa. In yet other variations, the first electrode (1902) may be activated and followed by the second electrode (1912), or vice versa. In some variations a combination of these modes may be combined or alternated. In some variations, the electrodes may be activated in alternation, for example for a fixed number of cycles. The electrodes may have the same or different shapes, widths, and geometry. It should be appreciated that any combination of electrode and catheter designs described herein may be used in the dual-sided electrode systems contemplated herein.

E. Synergistic Ablation Systems

In other variations, the catheter systems described herein may be configured for synergistic ablation. Synergistic ablation as referred to herein means tissue ablation through one blood vessel that relies on tissue ablation through another blood vessel. For instance, synergistic ablation may begin by ablating tissue with a first catheter disposed in a first blood vessel. Once a predetermined amount of tissue is ablated, a second catheter disposed in a second blood vessel may provide concurrent tissue ablation until fistula formation is complete. In this manner, tissue ablation may begin with one catheter but be subsequently combined with tissue ablation from a second catheter. As described in detail herein, synergistic ablation may improve the safety and increase the speed of fistula formation, and may be provided by a compact system.

More particularly, in synergistic ablation, tissue ablation may be performed in a first blood vessel by a first catheter for a predetermined period of time and is followed by tissue ablation performed in a second blood vessel by a second catheter in conjunction with tissue ablation by the first catheter. For example, a first catheter may comprise an electrode that acts as an active electrode, while a second catheter may comprise a conductive material that activates only upon contact with the electrode of the first catheter. The electrode of the first catheter may be energized by a power source to perform tissue ablation. Once sufficient tissue is ablated from the blood vessels, the electrode of the first catheter may make physical contact with the conductive material of the second catheter such that the conductive material is energized by the power source through contact with the electrode of the first catheter. It should be noted that even when the conductive portion is not energized, the conductive portion may stretch and/or compress tissue to improve tissue ablation by an electrode of the first catheter.

Figure 20A:
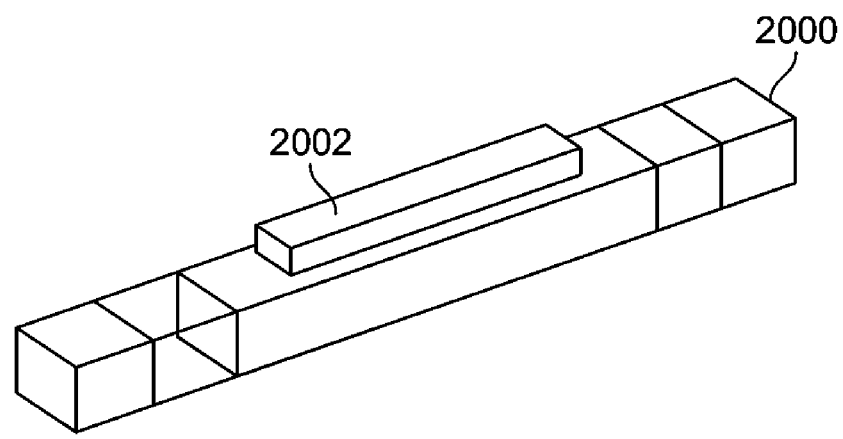
FIGS. 20A-20D depict several variations of a system comprising a first catheter comprising an electrode and a second catheter comprising a conductive portion.
Figure 20B:
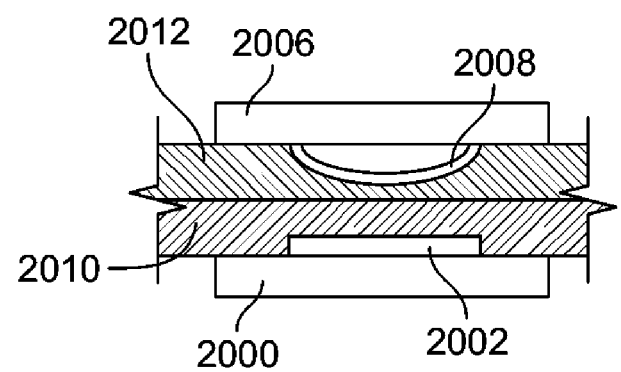
Figure 20C:
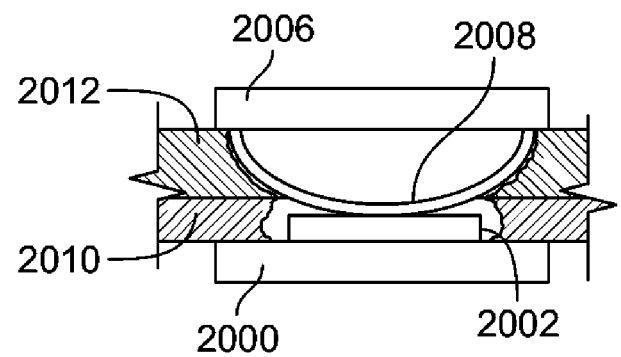
Figure 20D:
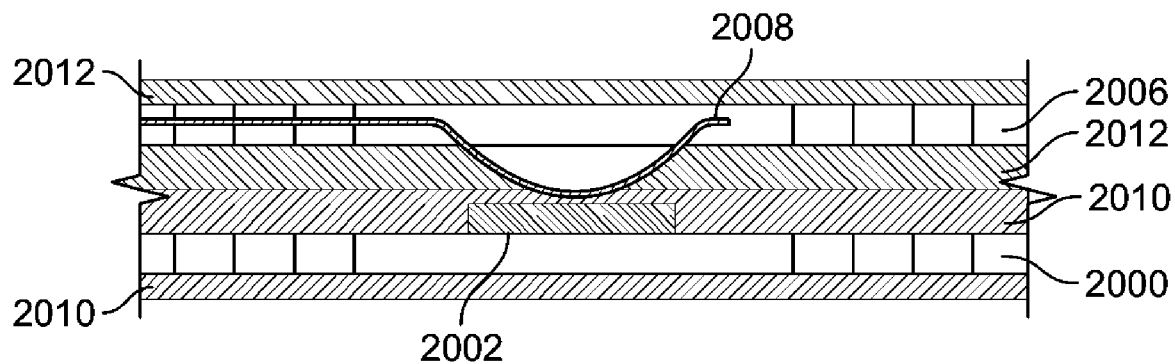

FIGS. 20A-20D are illustrative depictions of portions of a system including a first catheter (2006) comprising an electrode (2008) and a second catheter (2000) comprising a conductive portion (2002). FIG. 20A is a perspective view of a portion of the second catheter (2000). FIGS. 20B-20D show cross-sections of a portion of the first (2006) and second (2000) catheters disposed in blood vessels (2010, 2012). The first catheter (2006) may comprise an active electrode (2008) coupled to a power source (not shown). The second catheter (2000) may comprise an electrically conductive portion (2002), configured to be contacted by the electrode (2008). FIGS. 20C-20D are cross-sectional side views of the first catheter (2006) and second catheter (2000) disposed in blood vessels (2010, 2012). Upon activation of the electrode (2008), the electrode may generate plasma and the tissue adjacent to the active electrode in a first blood vessel (2012) may be ablated (FIG. 20C). The active electrode (2008) may advance through the walls of the first and second vessels to contact the electrically conductive portion (2002) of the second catheter (FIG. 20C). Contact between the two electrical surfaces may serve to electrically connect the active electrode (2008) to the electrically conductive portion (2002) such that they generally share the same electrical potential, and the electrically conductive portion (2002) serves as an extension of the electrode (2008). Subsequent to contact, energy supplied from the power source may conduct directly into the electrically conductive portion (2002), thereby promoting the formation of a plasma on the electrically conductive portion (2002). This may serve to ablate or further remove tissue that the conductive portion (2002) is in contact with from within the second blood vessel (2010), until the electrode (2008) has traveled fully through the walls of both vessels and rests against the conductive portion (2002) (FIG. 20D). In this way, a single electrical source may conduct energy into two separate electrodes in a system, the second electrode of which activates only when the first forming element has established contact.

Figure 21A:
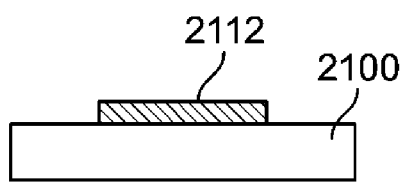
FIGS. 21A-21E are side views of several variations of a catheter comprising a conductive portion.
Figure 21B:
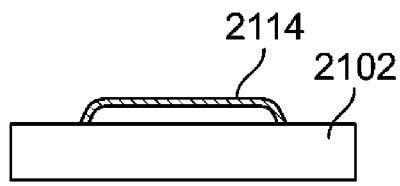
Figure 21C:
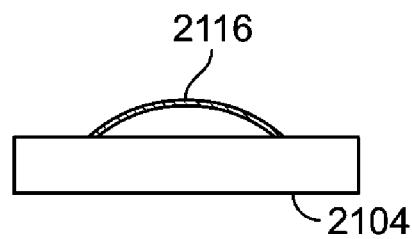
Figure 21D:
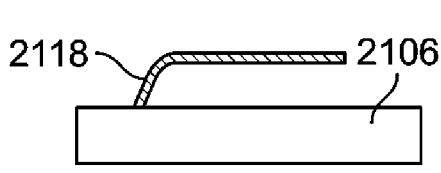
Figure 21E:
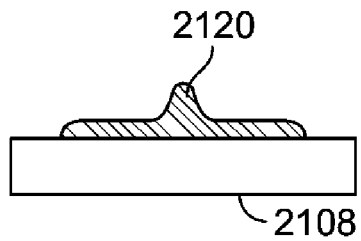

It should be appreciated that the conductive portion of the second catheter may have any suitable shape. That is, the conductive portion is not particularly limited in size and shape and may comprise a spring, a raised wire, and/or a rigidly fixed metallic surface. FIGS. 21A-21E depict side views of several variations of the conductive portion disposed on various catheters (2100, 2102, 2104, 2106, 2108), including a flat conductive portion (2112) as shown in FIG. 21A, a protruding conductive portion having a first and second bend (2114) as shown in FIG. 21B, a rounded conductive portion (2116) as shown in FIG. 21C, a protruding conductive portion having a one bend (2118) as shown in FIG. 21D, and a protruding conductive portion having a projection (2120) as shown in FIG. 21E. It should be appreciated that any combination of electrode designs described herein may be used in the synergistic ablation systems contemplated herein.

In some variations, the first catheter (2006) and second catheter (2000) shown in FIG. 20A-20D may be used to form an arteriovenous fistula by first ablating tissue from the venous side of a coapted artery-vein pair. Once a hole has been produced by the advancing electrode (2008) coming from the venous side, the arterial portion (2002) may be made to activate via electrical contact with the active electrode (2008) to further remove tissue on the arterial side. Synergistic ablation in this manner may prevent incomplete fistula formation due to a breach in the arterial wall when fistula formation begins from an arterial side. For instance, arterial ablation may be activated only when the conductive portion (2002) directly contacts the electrode (2008) from the venous side, which occurs only if a hole is formed from the venous lumen to the arterial lumen. Thus, the risk of high-flow arterial blood undesirably increasing the size of a fistula is reduced.

In some variations, synergistic ablation may enable enlargement of the fistula aperture using a leaf spring electrode of a first catheter advancing from a venous side of a coapted artery-vein pair. Where the conductive portion is energized by the electrode, the conductive portion need not include wires or other elements through the second catheter to energize the conductive portion. In some variations, a conductive portion of a second catheter opposing an electrode (e.g., leaf spring electrode) may be free of electrical components within the proximal section of the catheter (e.g., power source and wire to energize the conductive portion). Accordingly, a proximal coaption region of the second catheter comprising a set of magnets may be provided with more mass and attractive force, thus increasing tissue compression and catheter alignment. Additionally or alternatively, the second catheter may be formed with a smaller diameter relative to the first catheter or other alignment elements relative to the first catheter.

F. Energy Source

As described herein, the electrodes described herein may be connected to a radiofrequency current generator (e.g., via the monopolar or bipolar output of the current generator) to energize the electrodes for the various applications described herein (e.g., blood vessel modification, tissue ablation). The electrodes may be advanced into a first blood vessel adjacent a second blood vessel, and in some of these variations, a ground electrode may be placed external to the patient, and current may be applied to the tissue via the electrode to form a fistula between the two vessels. The tissue of a first blood vessel, being located closer to the electrode, may be ablated or vaporized more quickly than tissue of a second blood vessel. Additionally, in variations where the electrode is configured to extend through tissue while ablating, the electrode may first contact and ablate tissue of the first blood vessel prior to contacting and ablating tissue of the second blood vessel.

In some variations, one or more electrodes may be connected to an electrosurgical generator, power supply, or other waveform generator that is configured to generate an alternating current under the control of an electrosurgical controller. In some of these variations, one or more electrodes may be connected to a monopolar output of a generator. In other variations, two or more electrodes may be connected to the bipolar outputs of a generator. In some of these variations, a first electrode is attached to the active output of the generator, and a return electrode (e.g., a large metal plate or flexible metalized pad) may be temporarily attached or affixed to the patient and connected to the return output of the generator. In others of these variations, two or more electrodes may be attached to an active output of the generator, and a return electrode may be temporarily attached or affixed to the patient and connected to the return output of the generator. In still other variations, a first electrode may be attached to the active output of the generator, and a second electrode may be attached to the return output of the generator. In yet other variations, a first electrode may be connected to an output of a generator and a second electrode may be floating, that is, not directly connected to any output of the generator, in a focused monopolar configuration.

In some variations, the radiofrequency current generator may be a high voltage generator having a voltage range from about 180 V peak and about 500 V peak and a frequency range between about 150 kHz and about 8 MHz. The generator may be configured to generate, for example, sinusoidal and square waveforms.

G. Alignment Features

In variations in which a system having multiple catheters is used to create a fistula between two blood vessels, each catheter may be configured to promote rotational and/or axial alignment. Proper axial and rotational alignment between two catheters may facilitate alignment of one or more fistula-forming elements on a first catheter with one or more corresponding elements (e.g., one or more fistula-forming elements, one or more corresponding surfaces (e.g., a backstop)) on a second catheter.

Figure 22A:
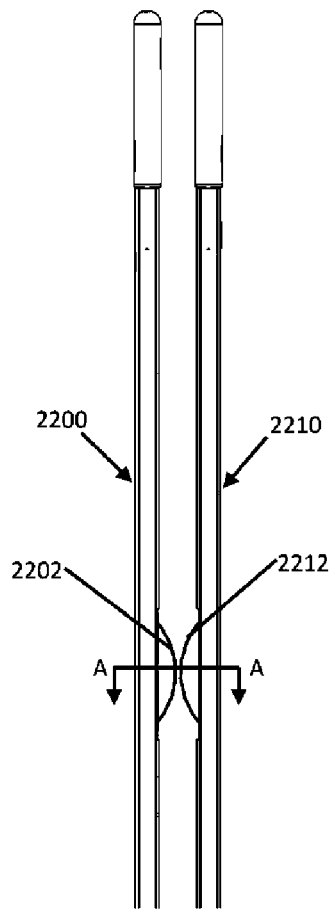
FIGS. 22A-22D depict another variation of a system comprising a first catheter and second catheter having respective first and second electrodes.
Figure 22B:
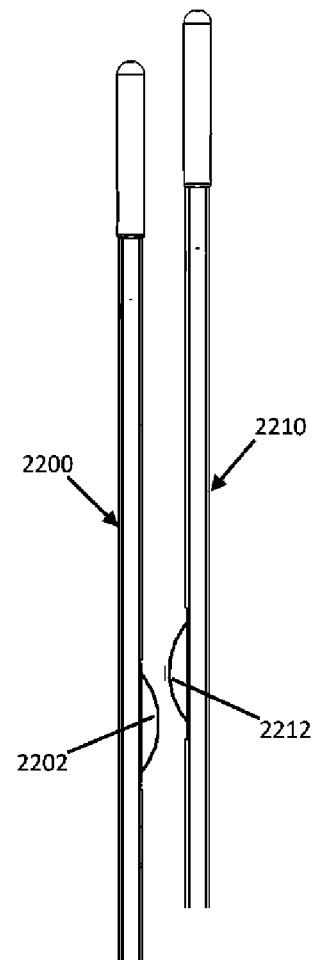

To illustrate axial and rotational alignment, FIG. 22A shows a catheter system comprising a first catheter (2200) and second catheter (2210), wherein the catheters are axially aligned such that their respective first electrodes (2202, 2212) may form a fistula from opposing sides of the same region of tissues (not shown for clarity). By contrast, FIG. 22B illustrates the first catheter (2200) and second catheter (2210) axially misaligned such that their respective first electrode (2202) and (2212) contact tissues at two different axial locations along the vessels.

Figure 22C:
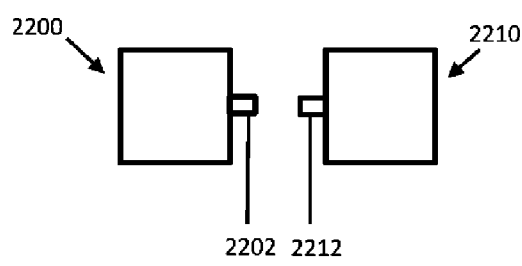
Figure 22D:
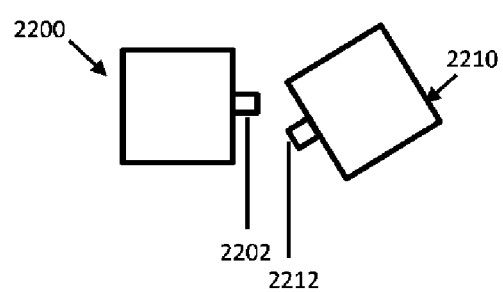

FIGS. 22C-22D each depict a cross-sectional view of the first catheter (2200) and second catheter (2210) along the A-A line of FIG. 22A. FIG. 22C illustrates the first catheter (2200) and the second catheter (2210) rotationally aligned. By contrast, FIG. 22D illustrates the first catheter (2200) rotationally misaligned to the second catheter (2210). One or more magnets, flat coaption surfaces, rotational indicators, and handle features may help to achieve axial and/or rotational alignment, as described in more detail herein.

1. Magnets

As mentioned above, the catheters of the systems described here may comprise one or more magnets, which may assist with rotational and axial alignment, as well as bring the catheters together to compress tissue. Generally, the magnets may be configured to be attracted to one or more magnetic fields (e.g., produced by one or more magnets of another catheter). The magnets may help to align or otherwise reposition the catheters when placed in the vasculature. In some instances, a system may comprise first and second catheters each having one or more magnets, such that magnets of the first catheter may be attracted to magnets of the second catheter to bring the catheters in closer approximation. The one or more magnets may help to ensure that one or more catheters are in proper axial and/or rotational alignment relative to another catheter or catheters. Such axial and/or rotational alignment of catheters may also facilitate alignment of one or more fistula-forming elements relative to a fistula site.

In variations in which the catheters of the systems described here comprise one or more magnets, each catheter may have any number of individual magnets (e.g., one, two, three, four, five, six, seven, or eight or more, etc.). In variations in which a catheter has a plurality of magnets, these magnets may be grouped into one or more magnet arrays. The magnets may be located inside and/or outside of a catheter body. The magnets may be positioned anywhere along the length of the catheter. In some variations in which a catheter comprises an electrode, an alignment portion may include one or more magnets proximal to an electrode. Additionally or alternatively, the first catheter may have one or more magnets distal to the electrode.

The magnets described here throughout may be permanent magnets comprising one or more hard magnetic materials, such as but not limited to alloys of rare earth elements (e.g., samarium-cobalt magnets or neodymium magnets, such as N52 magnets) or alnico. In some variations, the magnets may comprise anisotropic magnets; in other variations, the magnets may comprise isotropic magnetics. In some variations, the magnets may be formed from compressed powder. In some variations, a portion of the magnets (e.g., a permeable backing) may comprise one or more soft magnetic materials, such as but not limited to iron, cobalt, nickel, or ferrite. It should be appreciated that in some variations of systems comprising two catheters, either the first or second catheter may comprise ferromagnetic elements (i.e., elements attracted to but not generating a permanent magnetic field). For example, in some variations, the first catheter may include only one or more ferromagnetic elements while the second catheter may comprise one or more permanent magnets. In other variations, the second catheter may include only one or more ferromagnetic elements while the first catheter may comprise one or more permanent magnets. However, in other variations, one or both of the first and second catheters may include any suitable combination of ferromagnetic, permanent, and/or other suitable kinds of magnets.

Generally, the dimensions of the magnets described herein may be selected based upon by the size of the catheters carrying the magnets, which in turn may be selected based upon the anatomical dimensions of the selected blood vessels through which the catheters may be advanced. For example, if the catheter is to be advanced through a blood vessel having an internal diameter of about 3 mm, it may be desirable to configure any magnet to be less than about 3 mm at the widest part of its cross-section, to reduce the risk of injury to vessel walls during advancement and manipulation of the catheter. Each magnet may have any suitable length (e.g., about 5 mm, about 10 mm, about 15 mm, about 20 mm, or the like), although it should be appreciated that in some instances longer magnets may limit the flexibility of the catheter to maneuver through tissue. Accordingly, in some variations, a plurality magnets (e.g., square magnets, as described in more detail herein) may be arranged in a linear array along the length of a catheter to promote flexibility of the catheter.

Given the limitations on magnet size, it may be desirable in some instances to use magnets configured to produce magnetic fields that increase the magnetic force that can be generated with a magnet of a given size. For example, in some variations the system may comprise one or more of the magnets described in U.S. patent application Ser. No. 14/214,503, filed on Mar. 14, 2014, and titled "FISTULA FORMULATION DEVICES AND METHODS THEREFOR," and/or U.S. patent application Ser. No. 14/657,997, filed on Mar. 13, 2015, and titled "FISTULA FORMATION DEVICES AND METHODS THEREFOR," each of which is hereby incorporated by reference in its entirety.

Each magnet may be fixed in or on a catheter by any suitable method. For example, in some variations one or more magnets may be embedded in, adhered to, or friction-fit within a catheter.

2. Flat Coaption Surfaces

In general, proper rotational alignment between two catheters may be promoted by a flat coaption surface. For example, the two catheters may each comprise a flat surface configured to be aligned with the flat surface of the opposing catheter, and in some instances the catheters may have a rectangular or square cross-section for all or a portion of each catheter's length. In some variations, magnets within the catheters may also have a rectangular or square cross-section. These flat surfaces of opposing catheters may help to naturally align the two catheters with each other. This is similar to the phenomenon that a rigid body placed onto an angled surface will automatically align itself to be parallel to the surface due to gravitational forces. For instance, when an edge of a box is placed on a flat surface, gravity will produce a moment with respect to the center of gravity of the box such that the box will fall over and align itself with the flat surface to reach equilibrium. Similarly, magnetic coaption forces may bring two flat magnetic surfaces together in parallel with each other when brought in close proximity to each other. As such, flat coaption surfaces may bring a pair of catheters into rotational alignment and increase tissue compression to enhance fistula formation.

FIGS. 23A-23D illustrate a system having a first catheter (2300) and a second catheter (2310) each comprising a flat coaption surface. As shown there, the catheters (2300, 2310) each comprise a coaption region (2316, 2318) in a distal portion of the catheter, where the coaption region has a square cross-section. As such, one side of each coaption region (2316, 2318) forms a flat coaption surface (2306, 2314). When the first and second (2300, 2310) catheters are properly aligned as shown in FIGS. 23A-23D, the flat coaption surface (2306) of the first catheter faces the flat coaption surface (2314) of the second catheter (2310).

Figure 23A:
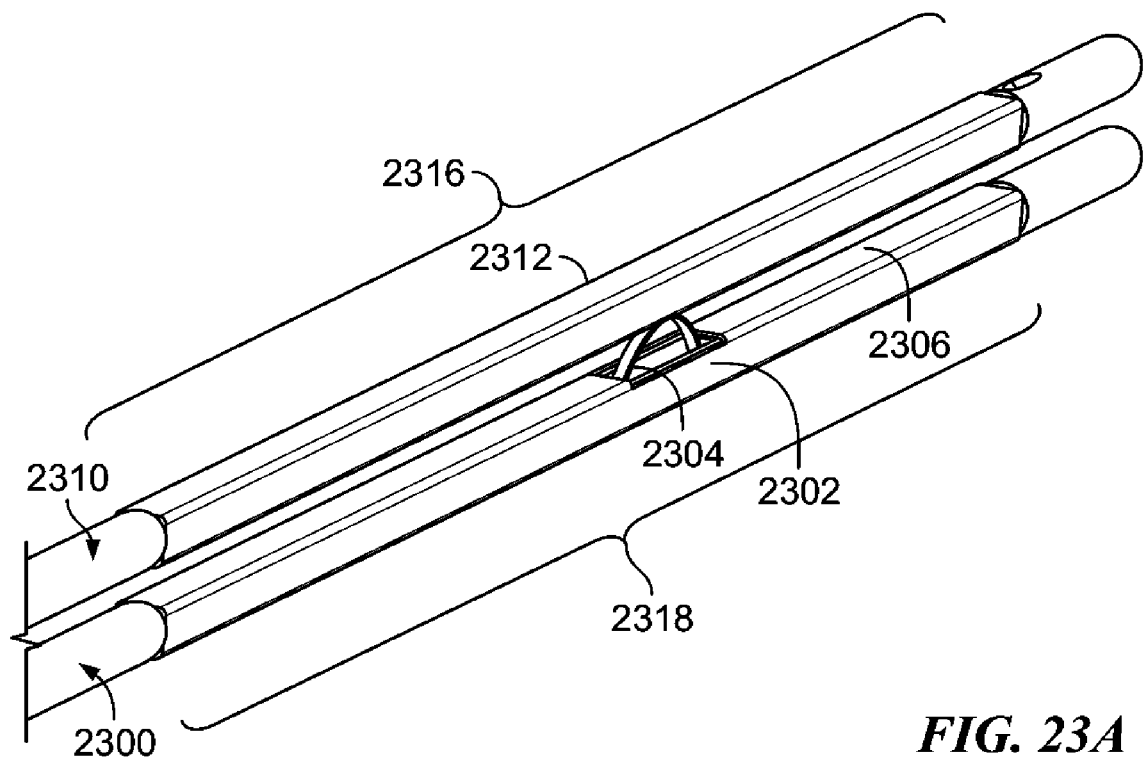
FIGS. 23A-23D depict another variation of a system including a first catheter comprising an electrode and a second catheter comprising a backstop.
Figure 23B:
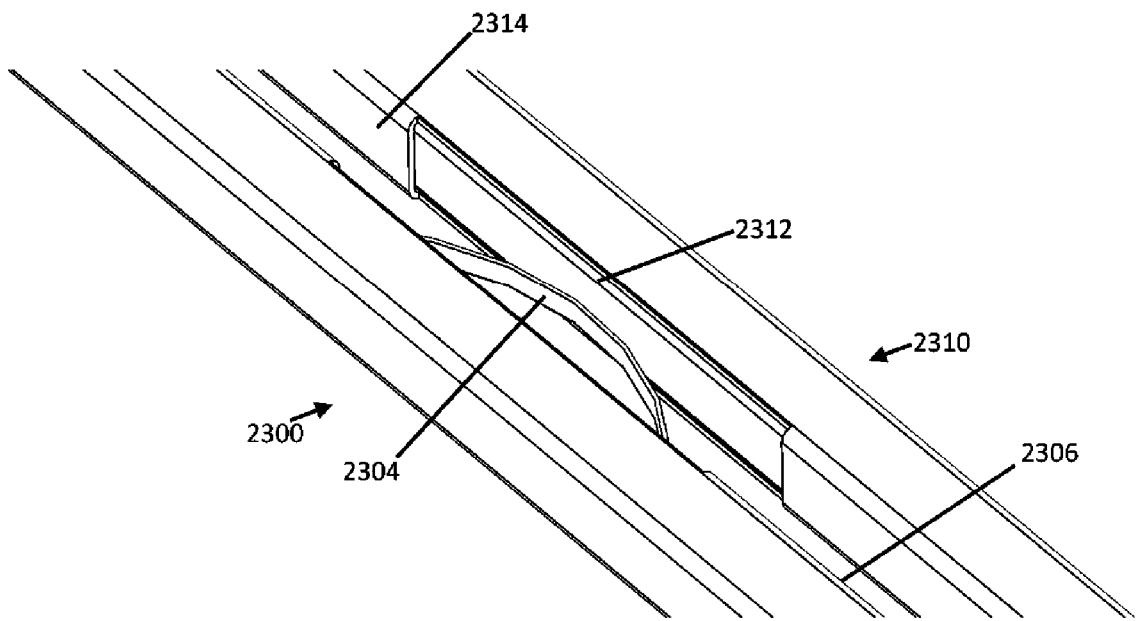
Figure 23C:
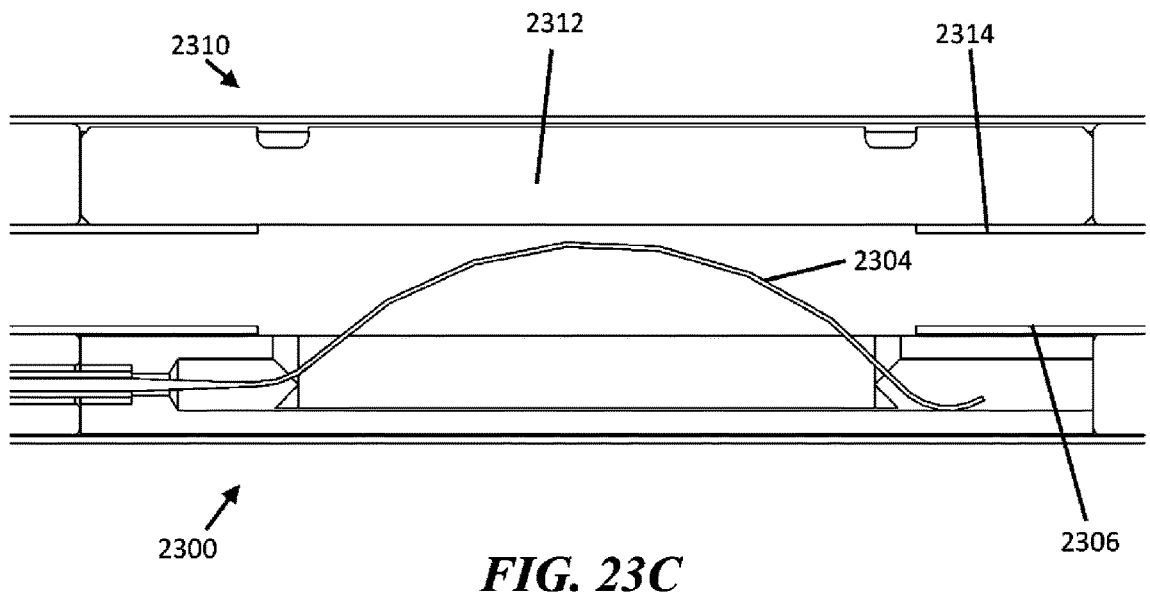
Figure 23D:
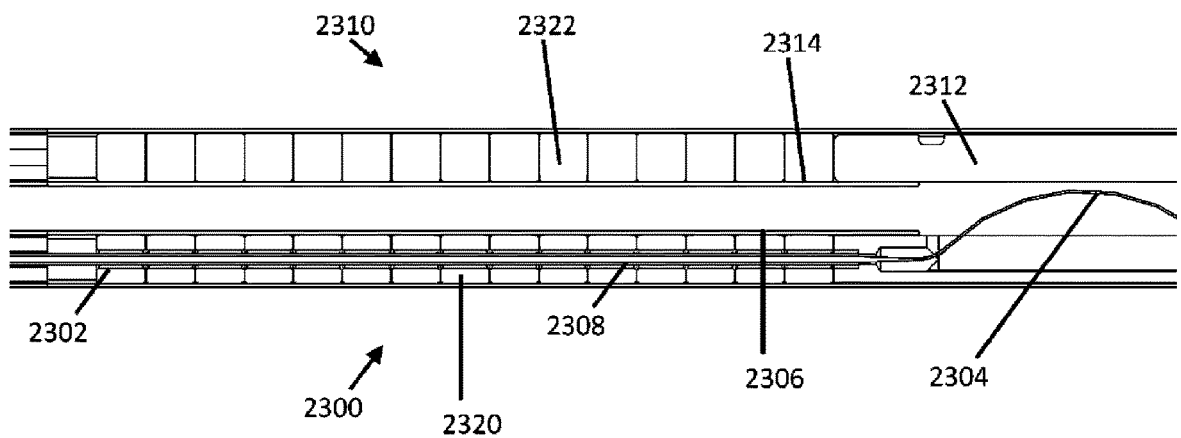

Each catheter may further comprise magnets within one or more portions of the coaption regions. In some variations, the first catheter may comprise one or more magnets proximal to the electrode and one or more magnets distal to the electrode, and the second catheter may comprise one or more magnets proximal to the backstop (or electrode or conductive contact in a dual-sided system) and one or more magnets distal to the backstop (or electrode or conductive contact in a dual-sided system). FIG. 23D is a cross-sectional view of a portion of the catheters (2300, 2310), showing a series of square magnets (2320, 2322) in the first and second coaption regions (2316, 2318) proximal to the electrode (2304) and backstop (2312), respectively. The magnets (2320) in the coaption region (2318) of the first catheter (2300) may comprise a lumen for a wire (2308) to electrically couple a power source to the electrode (2304). The wire (2308) may be covered by insulation (2302) to shield the magnets (2320) from current carried by the wire (2308).

In FIGS. 23A-23D, where the second catheter (2310) provides a backstop (2312), the magnetic forces of attraction are focused on the backstop (2312), which may increase tissue compression between the backstop (2312) and the electrode (2304). When the first catheter (2300) is located in a first vessel and the second catheter (2310) is located in an adjacent second vessel and the two catheters are properly aligned, magnetic forces of coaption may compress the electrode (2304) into the vessel tissue (not shown) by bringing the two catheters in close approximation, which may improve the ability to make a transmural cut. In addition to bringing the catheters closer together and compressing tissue, flat coaption surfaces may allow a lateral magnetic coaption force to be generated. An aligning torque corresponding to an attractive magnetic force may manifest when the first catheter (2300) and second catheter (2300) are rotationally misaligned, which may promote alignment of the catheters relative to each other. The aligning torque may increase as the catheters are brought closer together. Because the strength of the magnetic forces depends in part on the shape of the catheter surfaces (e.g., the aligning torque may be greater between a pair of flat magnetic surfaces than for a pair of magnetic cylinders), the two catheters each comprising a flat coaption surface may generate a greater aligning torque for a given amount of rotational misalignment than two catheters each comprising curved coaption surfaces. For example, for a pair of catheters each having a square cross-section forming a flat coaption surface, and each having a coaption region of magnets of approximately the same dimensions (e.g., diameter and length), the aligning torque generated between flat magnetic surfaces at 5 degrees of misalignment is at least approximately 18 times stronger than that of the aligning torque between magnetic cylinders.

Figure 19A:
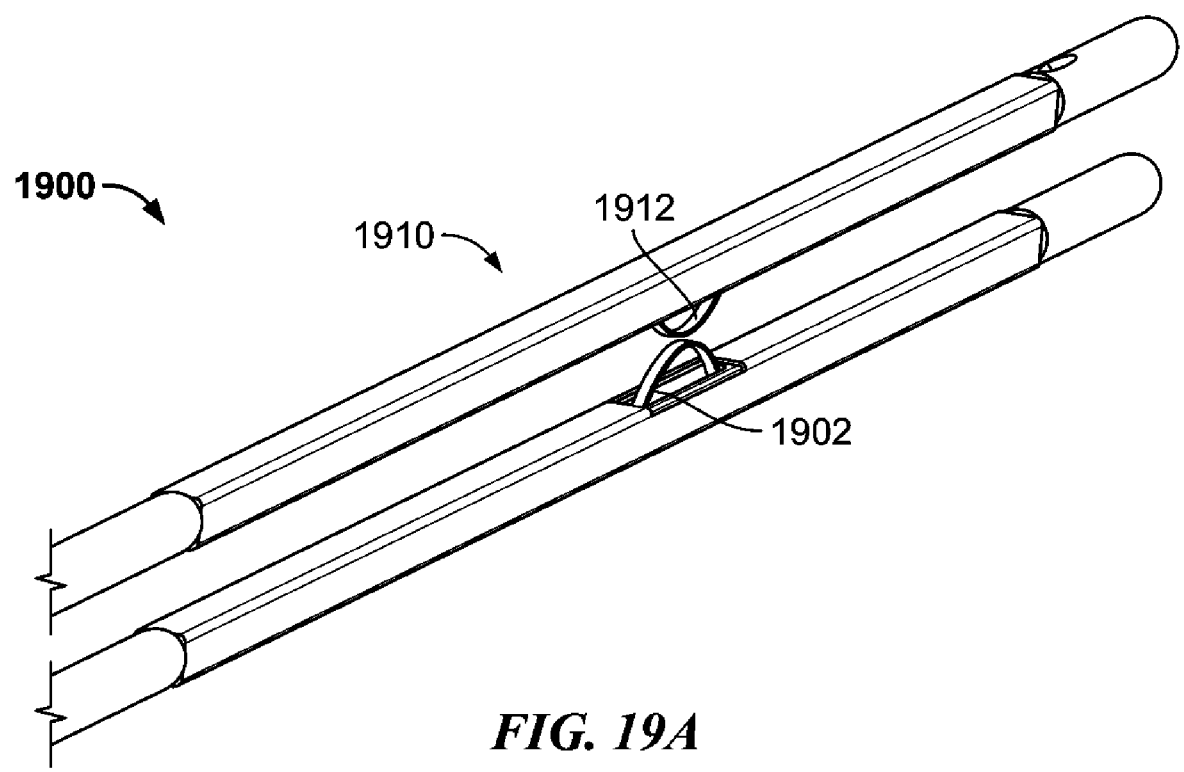
FIGS. 19A-19D depict another variation of a system comprising first and second catheters comprising respective first and second electrodes.
Figure 19B:
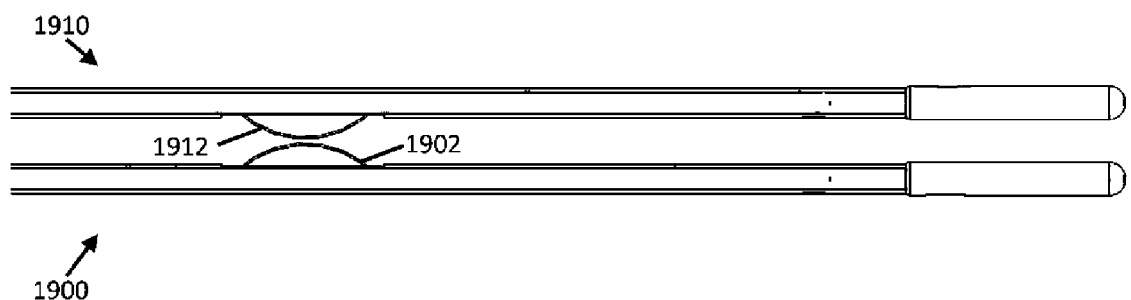
Figure 19C:
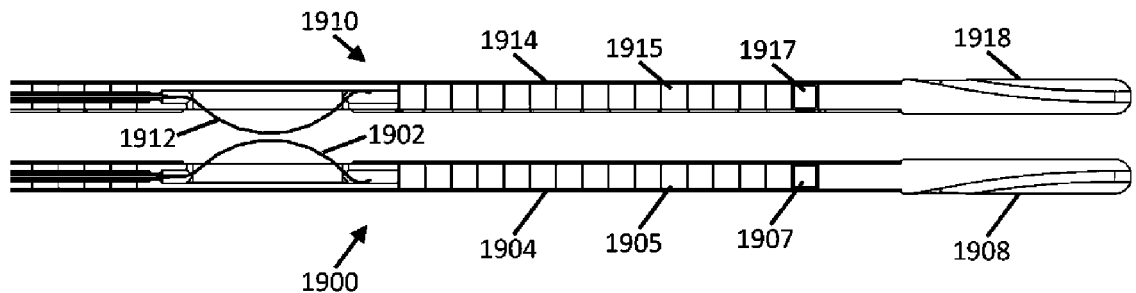
Figure 19D:
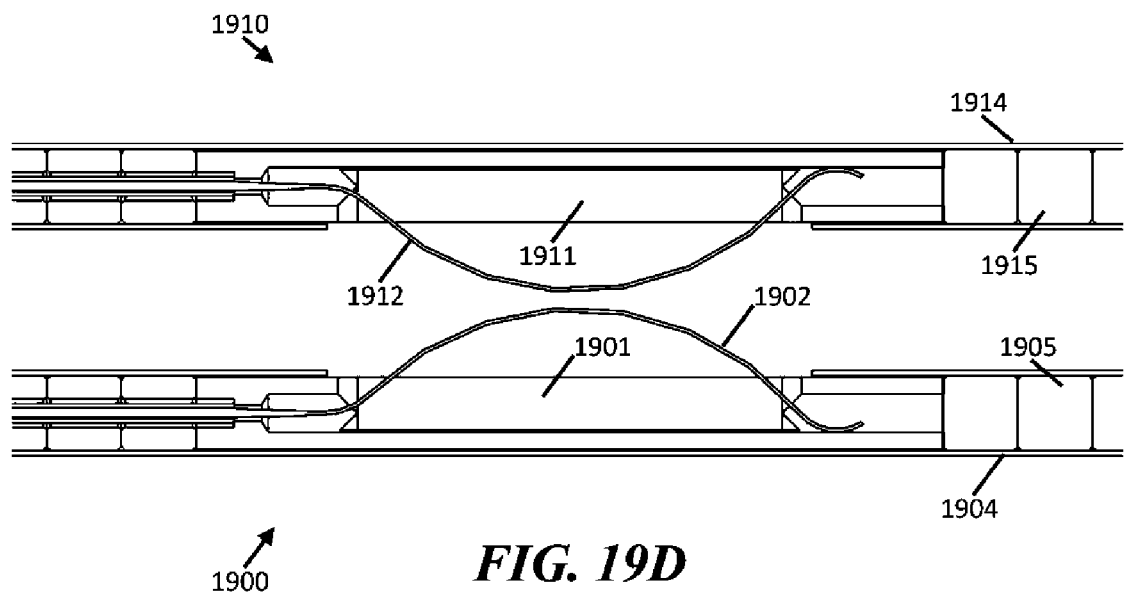

FIGS. 19C-19D show catheters (1900) and (1910) each comprising a coaption region with a flat coaption surface and an electrode. The coaption region may be located proximal and distal to the electrode and may have a square cross-section in to enhance the ability of the catheters to come into correct rotational alignment by virtue of magnetic aligning torque, as described in more detail herein. The first catheter (1900) comprising a first magnet array (1905). The second catheter (1910) comprises a second magnet array (1915). As shown, both catheters comprise magnet arrays proximal and distal to the electrode. The magnet arrays comprise a plurality of square magnets arrayed in a linear array. The magnets of the magnet arrays proximal to the electrode may comprise a central lumen therethrough that may allow for travel of a lead wire to the electrode. The linear arrangement of square magnets within catheters having a square cross-section may allow for improved rotational alignment, while still allowing for bending of the catheter. In some variations, a catheter may comprise one or more alignment features to assist with rotationally aligning the catheters, as described in more detail here. For instance, FIG. 19C a first rotational indicator (1907) (as described in detail herein) between the first magnet array (1905) and the first distal end (1908), and a second rotational indicator (1917) between the second magnet array (1915) and the second distal end (1918).

The coaption regions may have any suitable length along the catheters. For example, in one non-limiting variation, the coaption regions may extend about 15 mm distally and proximally from an electrode or backstop.

Once the first and second catheters have been positioned, the attractive force may also act to maintain the relative positions of the catheters. When the first and second catheters are placed in respective blood vessels, however, tissue positioned between the blood vessels and/or limited compliance of the blood vessels may limit the extent to which the magnets of the first and second catheters bring the first and second catheters toward each other. The size and strength of the magnets may be configured to provide a desired level of tissue compression, as described herein.

3. Visual Alignment Aids

In some variations, the catheters described herein may comprise visual alignment aids for indirectly visualizing alignment of catheters with respect to each other. Rotational alignment of the catheters may be difficult to discern. Fluoroscopically visualized rotational indicators, as described in detail herein, enable better rotational alignment of catheters relative to each other, and may also help with axial alignment.

A visual alignment aid may be visualized using a technique such as fluoroscopy during positioning and/or alignment of a catheter system. Fluoroscopy is a technique for real-time X-ray imaging and may be used to guide catheter insertion and movement through blood vessels. Generally, in fluoroscopy, an X-ray beam is emitted from a fluoroscope through an area of interest in a body. Objects to be visualized (e.g., catheters) may be imaged using an image intensifier. A user viewing the real-time images shown by the image intensifier may then determine the orientation and alignment of the catheters relative to each other. However, due to the two-dimensional nature of the X-ray images generated, some fluoroscopic visualization techniques may not be ideal for determining the three-dimensional orientation of one or more catheters. Thus, a rotational indicator may serve as a visual marker for guiding rotational alignment of two catheters as viewed under fluoroscopy. In some variations, when used in conjunction with a second catheter (not shown) having a second rotational indicator, the rotational indicators of each catheter may be used to rotationally and/or axially position the catheters relative to each other such that that one or more fistula-forming elements may be properly positioned to form a fistula. In some variations, a first catheter and a second catheter may each include identical rotational indicators having a radiopaque film. Imaging of rotational indicators having the same width and shape under fluoroscopy indicates rotational alignment of the first and second catheters relative to each other. Rotational indicators appearing the same under fluoroscopic visualization in adjacent catheters are aligned with respect to each other and indicate proper alignment for fistula formation. Accordingly, the catheters may be fluoroscopically aligned to each other rather than aligned to an X-ray beam.

Generally a rotational indicator may be configured such that its rotational orientation is discernable in a two-dimensional fluoroscopic image. One example is shown in FIGS. 24A-24B. FIGS. 24A-24B is are cross-sectional views of a catheter comprising a rotational indicator comprising a thin radiopaque film (2402) in a first rotational orientation parallel to an X-ray beam (2406) (FIG. 24A), and in a second rotational orientation rotated relative to the X-ray beam (2406) (FIG. 24B). The radiopaque film (2402) may block X-rays emitted from a fluoroscope to produce a shaded area when visualized on a user display (e.g. image intensifier). The width of the resulting shaded area, represented by width W between dashed lines in FIG. 24B, may correspond to an angular rotation of the catheter relative to the X-ray beam and is given by $2r \sin(\theta)$, where r is the thickness of the film and $\theta$ is the angle between the film and the X-ray beam. The radiopaque film (2402) may be configured to be very sensitive to rotational misalignment to allow for high precision rotational positioning. In some instances, a very thin (e.g., 0.025 mm thick) radiopaque film (2402) in parallel to the X-ray beam (FIG. 24A) may not be visible under fluoroscopy and may indicate to a user that the catheter (2400) is rotationally aligned with the X-ray beam. As the radiopaque film is rotated, a width of the visualized radiopaque band will increase. FIG. 24C depicts visualized rotational indicator width as a function of rotational error of a rotational indicator relative to an X-ray beam. Slight angular rotation errors of the rotational indicator (2402) may be easily visualized due to the sensitivity of the radiopaque film (2402).

Figure 25A:
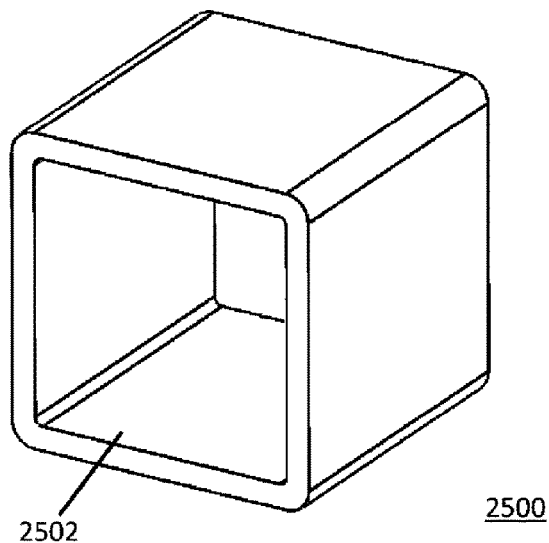
FIGS. 25A-25B are illustrative depictions of another variation of a rotational indicator.
Figure 25B:
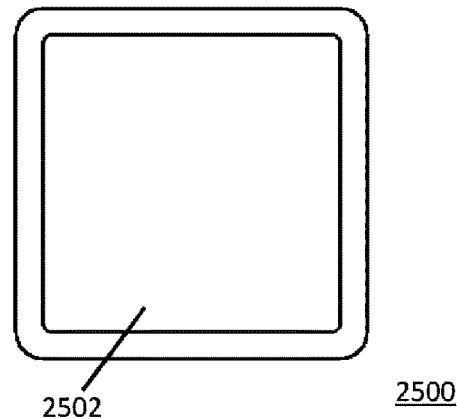
Figure 25C:
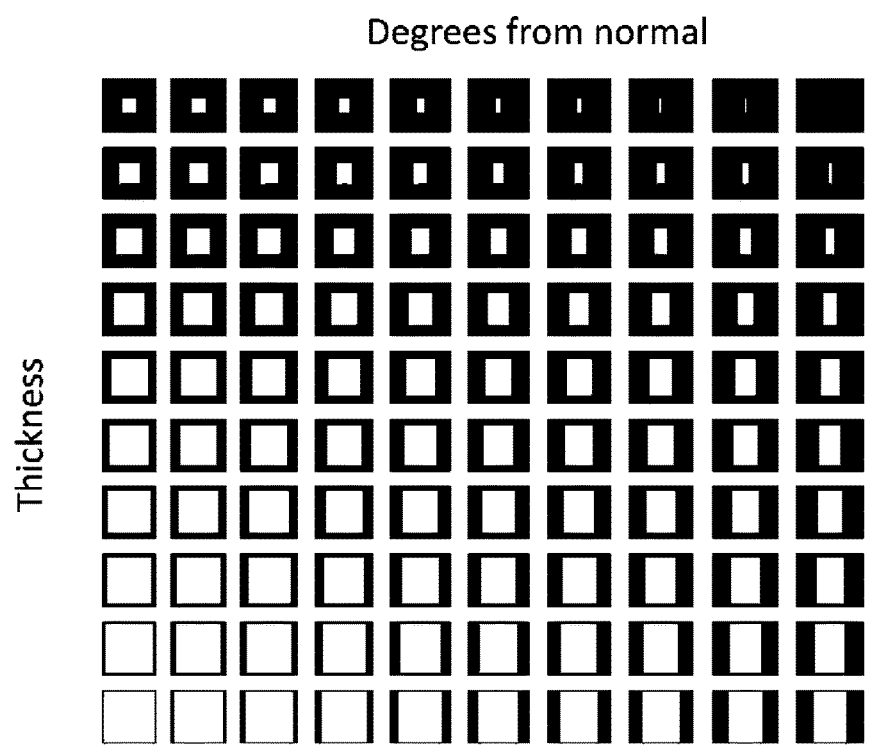
FIG. 25C depicts fluoroscopic visualization of rotational indicators similar to those depicted in FIGS. 25A-25B having varying thicknesses and orientation.

Other rotational indicators of various configurations may allow a user to visually match an orientation of a first rotational indicator in a first catheter to an orientation of a second rotational indicator in a second catheter. FIGS. 25A-25B show one variation of a rotational indicator (2500) having a cube shape with a corresponding cube-shaped cut-out (2502). The cube may have varying thicknesses, as shown in FIG. 25C which depicts fluoroscopic visualization of rotational indicators as shown in FIGS. 25A-25B as a function of varying levels of rotation from normal (e.g., X-ray beam perpendicularity), for differing indicator thicknesses. For two catheters having the same rotational indicator, if the rotational indicators appear the same in each catheter, no matter their misalignment from normal, then the catheters may be determined to be rotationally aligned with respect to each other and in position for fistula formation. In another variation, FIGS. 26A-26C depict a rotational indicator (2600) having a cube shape with a cylindrical cut-out (2602). FIG. 26D shows fluoroscopic images of rotational indicators (2600) as shown in FIGS. 26A-26C as a function of rotation from normal, for differing hole sizes.

Figure 27:
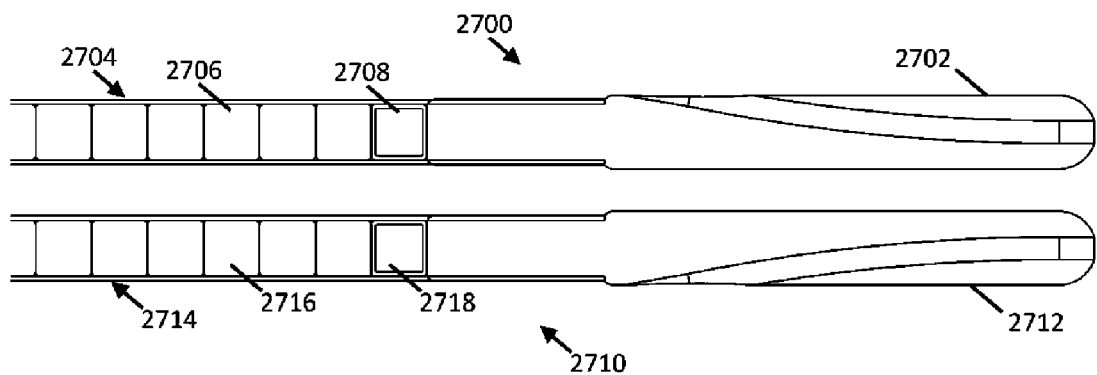
FIG. 27 is a cross-sectional side view of a distal portion of another variation of a system comprising first and second catheters each comprising a coaption region.

FIG. 27 shows distal portions of one variation of first and second catheters (2700, 2710) comprising rotational indicators (2708, 2718), which may be the rotational indicators of FIGS. 25A-25B or FIGS. 26A-26C. Each catheter may comprise a plurality of magnets (2706, 2716), which may be cube magnets. The rotational indicators (2708, 2718) may be located at the distal ends of the rows of cube magnets as shown, but it should be appreciated that the rotational indicators (2708, 2718) are not limited to a distal ends of the catheters and may be provided anywhere along the catheters. The distal ends (2702, 2712) of the catheters may optionally additionally include a rapid exchange atraumatic tip configured to pass a guidewire and allow tracking of the catheter over the guidewire.

FIGS. 28A-28C illustrate fluoroscopic images of another variation of a rotational indicator (2800) viewed fluoroscopically under different angles of rotation. For instance, the rotational indicator may have a shape corresponding to an alphanumeric character such as the letter "H" or any suitable written character. FIG. 28A shows a rotational indicator (2800) as imaged by a perpendicular X-ray beam. FIGS. 28B-28C show fluoroscopic images (2802, 2804) of the same rotational indicator as in FIG. 28A under increasing angles of deviation from perpendicularity with respect to the X-ray beam. For instance, the letter may appear thicker (2802) when slightly rotated or appear as a block (2804) after rotating 90 degrees.

FIGS. 29A-29B illustrate another variation of a rotational indicator (2900) having a cross-sectional shape of the letter "R," as shown in FIG. 29A. As the rotational indicator (2900) is rotated (FIG. 29B), the outline of the rotational indicator may increase in thickness. FIG. 30 is a cross-sectional view of a rotational indicator (3000) having an arrow shaped cut-out. FIG. 31 is a perspective view of a rotational indicator (3100) having a "U" shaped cut-out.

The rotational indicator may comprise any radiopaque metal, such as tungsten, platinum iridium, stainless steel, titanium, as well as a tungsten filled polymer, zirconia ceramic, or any suitable radiopaque material. A visual alignment aid, such as a rotational indicator, may be located at any suitable position on or within the catheter (e.g., one or more surfaces of the catheter, inside of the catheter, or the like). In some variations, one or more portions of the catheter may be made from a radiopaque material, or visual alignment aid may be attached to the catheter by any suitable method, for example, by mechanical attachment (e.g., embedded in a portion of the catheter, circumferential circumscription, or the like), adhesive bonding, welding, soldering, combinations thereof or the like. In some variations in which a second catheter has a backstop, the backstop itself may include a rotational indicator. For instance, a portion of the backstop may include a radiopaque material such as radiopaque zirconia ceramic. The shape of the radiopaque portion of the backstop may comprise any of the configurations described herein.

It should be appreciated that while the figures depict rotational indicators having various illustrated cross-sections, in other variations, the rotational indicators may have other shapes that allow for two-dimensional visualization of rotation. For example, in other variations the rotational indicators may be cylindrical, semi-cylindrical, or have a cross-section that is C-shaped (i.e., a D-shape or semi-cylindrical shape comprising a channel on the flat surface), rectangular, square, triangular, trapezoidal, ovoid, elliptical, or an $n^{th}$-order polygon, or the like.

A procedure for aligning catheters using the rotational indicators described is provided below. In some variations for positioning a first catheter and a second catheter within two vessels, a first catheter may be advanced into a first blood vessel and a second catheter may be advanced into a second blood vessel. The first catheter may include a first radiopaque portion and the second catheter may include a second radiopaque portion. An X-ray beam emitted from a fluoroscope may fluoroscopically image an orientation of the first radiopaque portion and the second radiopaque portion, which may be shown on a display for a user.

Figure 32A:
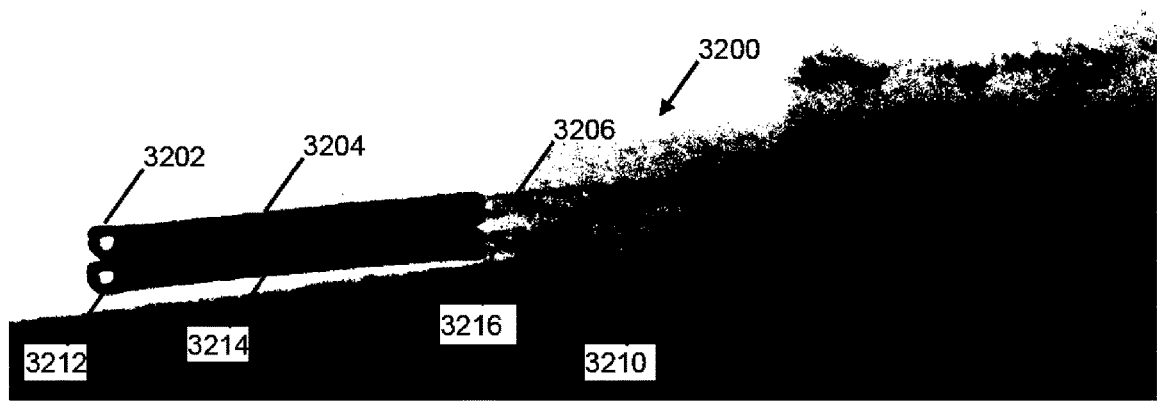
FIGS. 32A-32B are fluoroscopic visualizations of another variation of a system comprising first and second catheters each comprising rotational indicators.
Figure 32B:
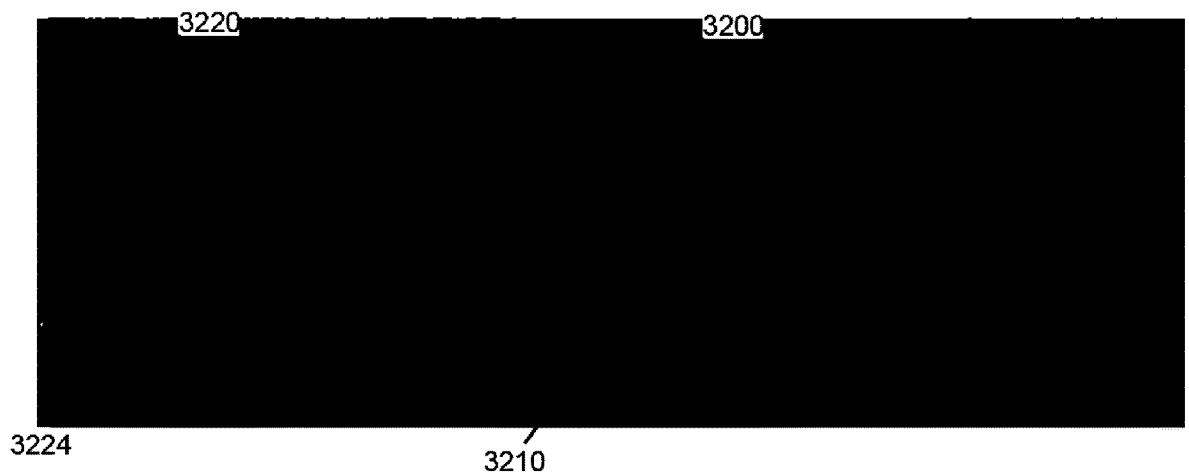

For example, FIGS. 32A-32B are illustrative fluoroscopic images of first and second catheters (3200, 3210). The first catheter (3200) comprises a first coaption region (3204) comprising magnets, a first rotational indicator (3202), and a first electrode (3206). Likewise, a second catheter (3210) comprises a second coaption region (3214) comprising magnets, a second rotational indicator (3212), and a second electrode (3216). The coaption regions (3204, 3214) and rotational indicators (3202, 3212) are of the same size and shape to allow comparison between the two under fluoroscopy. Axial alignment of the catheters (3200, 3210) is shown in FIG. 32A and may be confirmed by the coaption regions (3204, 3214) being in parallel with their edges lined up.

Rotational alignment of the first catheter (3200) relative to the second catheter (3210) may be confirmed by the rotational indicators (3202, 3212) appearing substantially identical in shape and thickness. To better illustrate this, FIG. 32B shows a detailed image of the first rotational indicator (3220) axially misaligned relative to the second indicator (3224). In particular, the rotational indicators (3220, 3224) have different thicknesses, indicating that they are rotationally offset from each other. The user may rotationally adjust one or both of the catheters (3200, 3210) until the appearance of the rotational indicators (3220, 3224) are substantially indistinguishable, thereby indicating rotational alignment the first catheter (3200) with the second catheter (3210). It should be appreciated that the rotational indicators and catheter alignment methods described here do not rely on an (often incorrect) assumption that the X-ray beam is perpendicular to a catheter plane. In other words, the catheters and rotational indicators described here may be aligned to each other irrespective of the incident angle of the X-ray beam to the catheter plane.

4. Handle

Generally, a proximal end of a catheter may comprise one or more handles, which a user may use to manipulate the catheter as it is advanced through vasculature. In some variations, a handle may have one or more features to assist with axial and/or rotation alignment with another catheter. For example, a handle may comprise a magnet and/or a flat mating surface. The handle may be coupled to a catheter shaft that may rotate as the handle is rotated. For example, in variations comprising a first catheter and a second catheter each having a handle, the handles may include magnets to bring and hold the handles in close approximation to and alignment with each other. Alignment of the handles may in turn bring distal ends of the catheters into alignment.

In variations of catheter pairs comprising handles each having a magnet for attracting and aligning the catheters in a preferred rotational and/or axial position, the handles may each have a flat mating surface to orient the catheters in the correct rotational position relative to each other. In some variations, catheter handles of first and second catheters may be configured to be attached to each other. They may be attached by any suitable method, such as but not limited to magnets, latches, snaps, adhesive, press fits, dovetails, etc.

In this way, correct internal orientation (i.e., orientation of the catheters within the blood vessels) may be achieved using external visible features (i.e., the handles located external to the body).

In some variations, the ability to orient an internal portion of a catheter based on the orientation of an external portion of the catheter (e.g., a handle) may be enhanced by utilizing a catheter shaft that is torsionally stiff (e.g., a braided shaft), so that rotational alignment at the external portion directly translates to rotational alignment of a more distal portion of the catheter. It may in some instances be desirable for different portions of a catheter to have different torsional stiffnesses. For instance, a proximal portion of the shaft may have a first torsional stiffness and a distal portion of the shaft may have a second torsional stiffness greater than the first torsional stiffness to ease rotation of the shaft along its length. In one variation, a proximal portion of the shaft having a lower torsional stiffness may be located distal to the handle and proximal to a magnet of a coaption region of the catheter.

Figure 33:
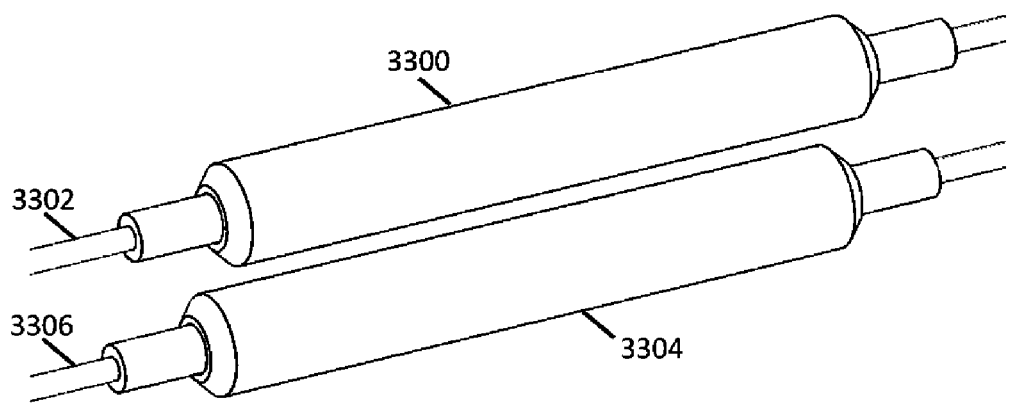
FIG. 33 is a perspective view of a variation of handles of first and second catheters.

As one example, FIG. 33 shows a first catheter shaft (3302) and a second catheter shaft (3306) coupled to a respective first handle (3300) and second handle (3304). The first handle (3300) and the second handle (3304) may include magnets to bring the handles together. The catheter shafts (3302, 3306) may be torsionally stiff such that rotation of the handle will provide corresponding rotation in the catheter shaft down through to a distal end of the catheter. In this manner, rotational and/or axial alignment of the handles (3300, 3304) may align the catheters as a whole.

Figure 34A:
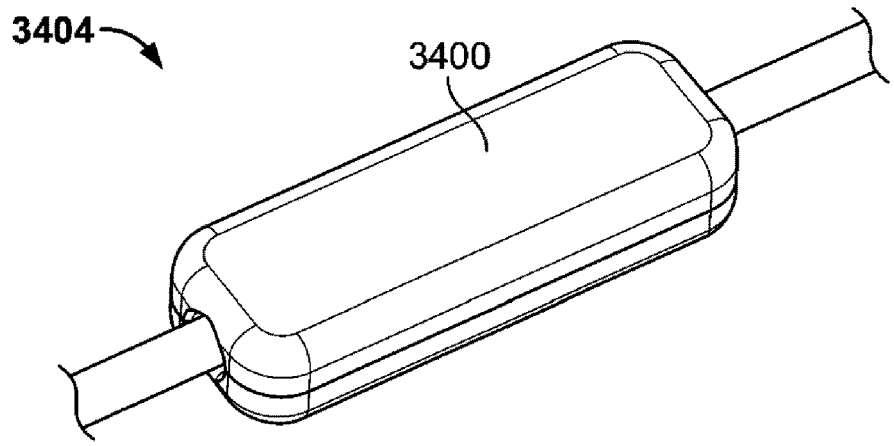
FIGS. 34A-34C depict another variation of a handle portion of a catheter.
Figure 34B:
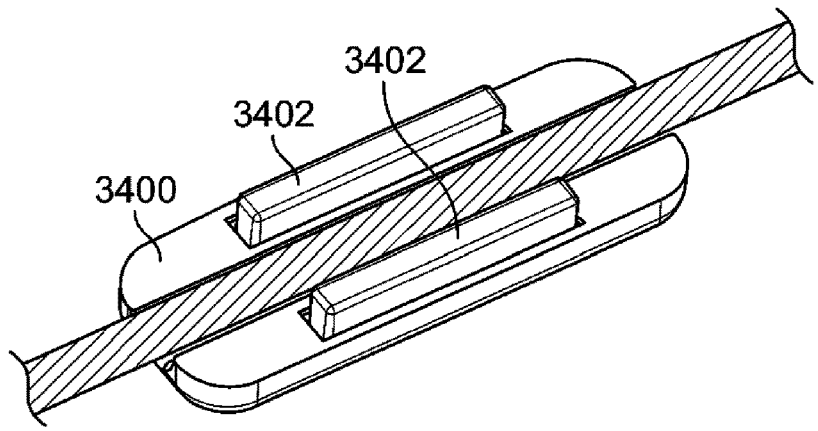
Figure 34C:
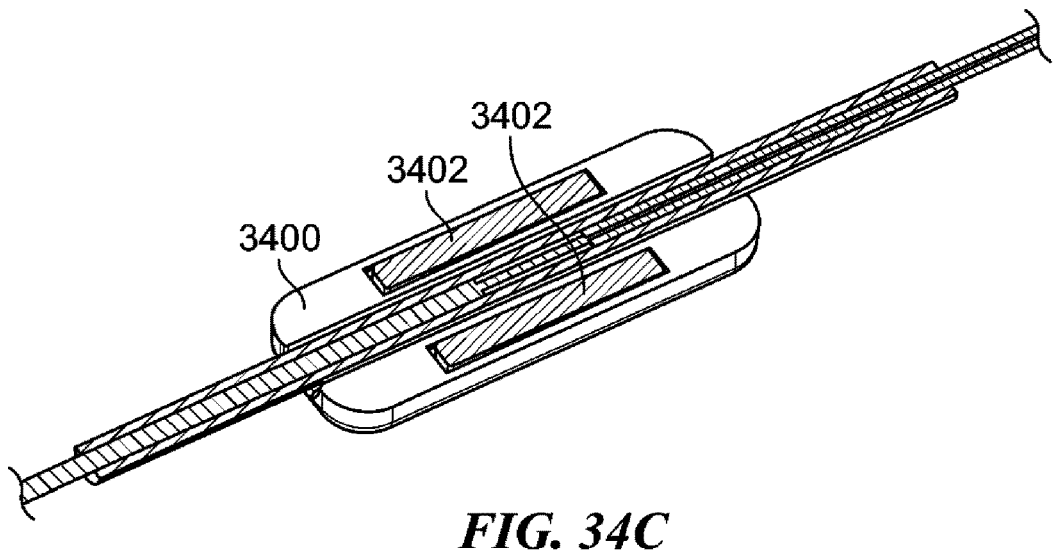

FIGS. 34A-34C depict a variation of a catheter (3404) comprising a handle (3400). FIG. 34A shows the handle (3400) comprising a flat surface for mating with a corresponding flat surface of another handle (not shown). FIGS. 34B-34C show magnets (3402) within the handle (3400) for attracting and aligning the handle in a preferred rotational and/or axial position. The handle (3400) may thus provide aligning torque for improved catheter alignment. It should be appreciated that the handle may need not further comprise one or more actuation components to deploy and retract a fistula-forming element through user manipulation.

H. Sensors

In one variation, systems comprising an electrode on both first and second catheters may further comprise an impedance metering circuit, such as a bipolar sensing circuit comprising the tissue ablation electrodes. To measure impedance of tissue between the electrodes, low power DC or alternating voltage may be applied to the electrodes. The resulting current and/or phase may be measured to determine impedance. As a user manipulates one or more catheters relative to each other and/or as the fistula is being formed, the measured impedance values may change to allow determination of a minimum impedance. The impedance values may be dependent on a number of factors, for example electrode size, but as a non-limiting example, in one variation an initial impedance (pre-fistula formation) may be between about 400Ω and about 500Ω, and a post-fistula formation impedance may be between about 0Ω and about 80Ω.

Additionally or alternatively, tetrapolar measurements with filtration/signal conditioning may be utilized to determine impedance. In some variations, one or more impedance measurements may be outputted to a user as one or more of visual and audio feedback. For example, the system may output an impedance value on a display meter coupled to the catheters. Impedance values may be output as audio tones. For instance, a predetermined tone may indicate a minimum impedance value corresponding to catheter alignment.

I. Example Catheter System

Figure 36A:
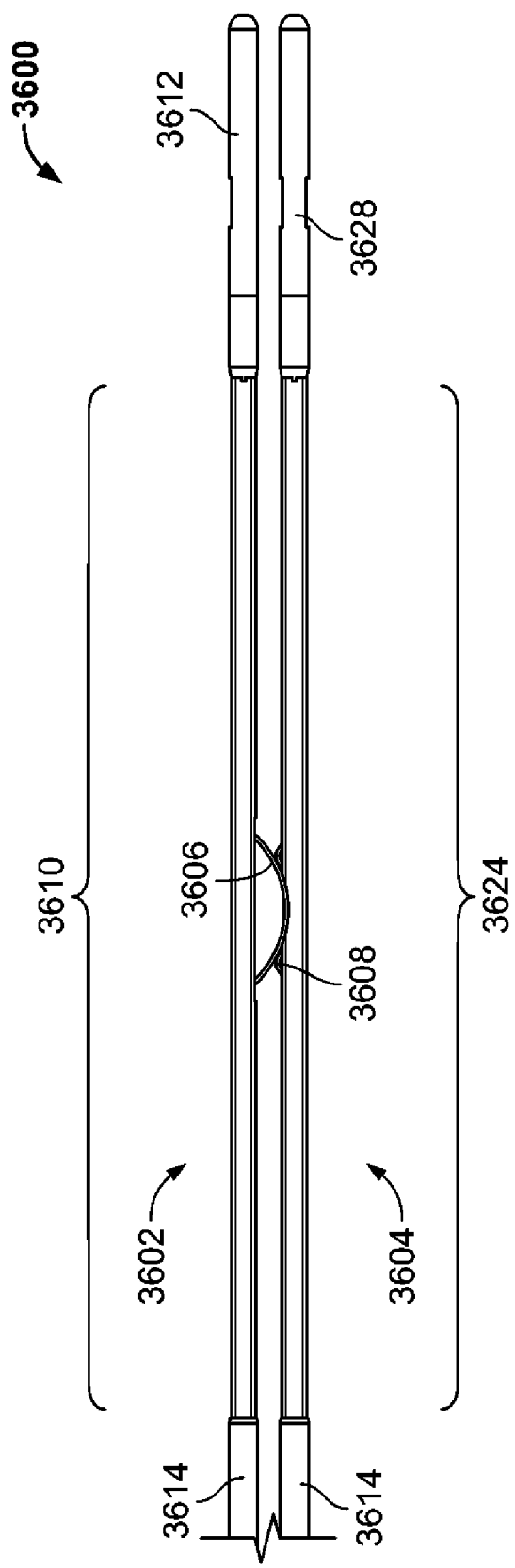
FIGS. 36A-36G are various side and perspective views of portions of another variation of a catheter system.

FIGS. 36A-36G depict an exemplary variation of a single-sided electrode catheter system (3600) comprising some of the components as described herein. FIG. 36A illustrates a distal portion of a first catheter (3602) and a second catheter (3604). The catheters (3602, 3604) may be configured to be advanced through vasculature in a minimally invasive manner. The catheters may have any suitable diameter for intravascular use, such as, for example, about 4 French, about 5.7 French, about 6.1 French, about 7 French, about 8.3 French, between about 4 French and about 9 French, between about 4 French and about 7 French, between about 4 French and about 6 French, or the like.

The first catheter (3602) may comprise a fistula-forming element (3606) and the second catheter (3604) may comprise a backstop (3608). The backstop (3608) may shape and control tissue ablation performed by the fistula-forming element (3606). The fistula-forming element (3606) may be an electrode and may have the features of electrode (106) described herein. The electrode may be attached to a housing of the first catheter (3602) and used to ablate tissue to form a fistula.

The electrode (3606) may be configured to have a low-profile configuration (not shown) and an extended configuration (as shown). The electrodes (3606) may be biased toward the extended configuration. That is, the electrode may be configured to self-expand from the low-profile configuration to the extended configuration. In some variations, the electrode may be held in the low-profile configuration by the inner surface of a vessel wall during delivery. The electrode may then self-expand toward the extended configuration as energy delivery through the electrode results in tissue ablation.

In the extended configuration, the electrode (3606) may be curved, such that it forms a convex curve extending away from the outer surface of the first catheter (3602). When the electrode (3606) moves from a low-profile to an extended configuration, the radius of curvature of the electrode (3606) may decrease, causing the electrode (3606) to protrude from the first catheter (3602). Conversely, when the electrode (3606) moves from an extended configuration to a low-profile configuration, the radius of curvature of the electrode may increase, causing the electrode to recess into an opening in the catheter body. The electrode (3606) may be configured to slide within the first catheter (3602) when the electrode (3606) moves between low-profile and extended configurations. More specifically, as shown in more detail with respect to FIGS. 1A-4, the electrode (3606) may comprise a first end and a second end, where both the first and second ends are located within the first catheter (3602). The first end of the electrode (3606) may be fixed, while a second end of the electrode (3606) may be slidable within a lumen inside of the first catheter (3602). When the slidable second end of the electrode (3606) moves toward the fixed first end of the electrode, the electrode (3606) may move toward an extended configuration. When the slidable second end of the electrode (3606) moves away from the fixed first end of the electrode (3606), the electrode (3606) may move toward a low-profile configuration. Because the electrode (3606) is curved, as the slidable second end moves toward the fixed first end of the electrode (3606), the radius of curvature of the electrode (3606) may decrease, causing the electrode (3606) to protrude from the first catheter (3602).

Figure 36B:
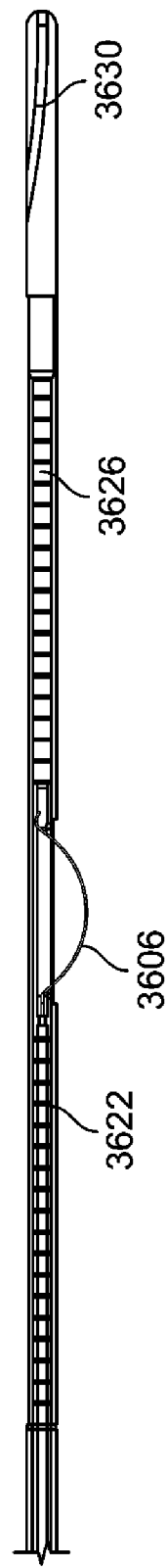
Figure 36C:
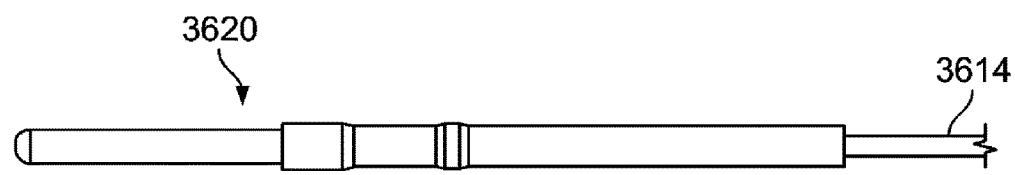

The electrode (3606) may be coupled to a power source (e.g., RF generator) by an electrical lead (3622) extending longitudinally through a catheter shaft (3614), that is in turn coupled to an electrical plug (3620), as shown in in the cross-sectional view of the first catheter in FIG. 36C.

Figure 36D:
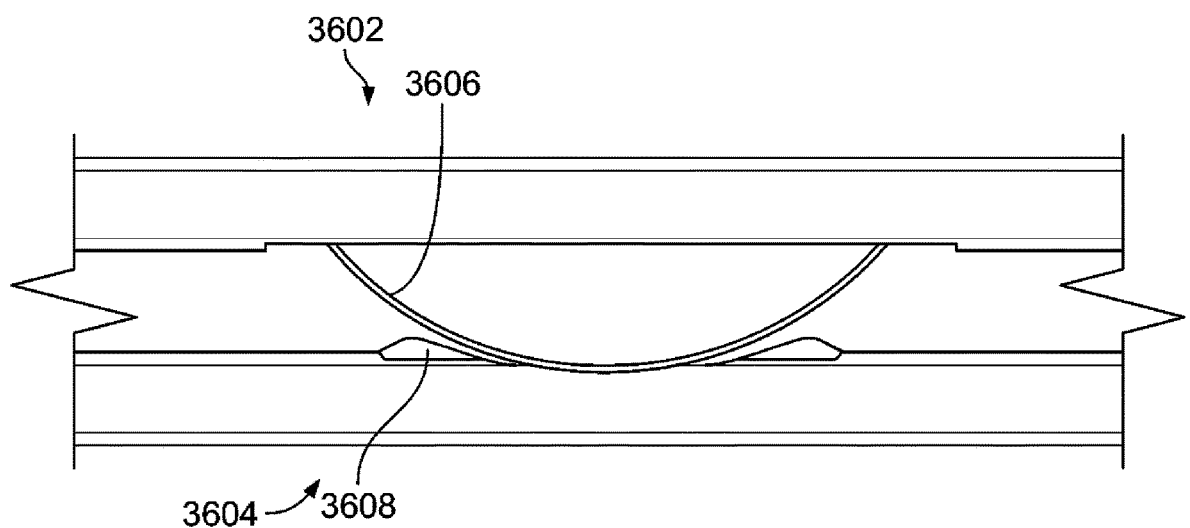

As best shown in FIG. 36D, the backstop (3608) of the second catheter (3604) may have a protruding backstop. The backstop (3608) may comprise a concave shape that is configured to be complementary to the electrode (3606) of the first catheter (3602). The concave portion of the backstop (3608) may correspond to the shape of an intermediate portion of the electrode (3606) when it is in the extended configuration. The backstop (3608) may be configured to compress tissue in a localized region for ablation by the electrode (3606) of a first catheter (3602).

The first and second catheters (3602, 3604) may further comprise respective coaption regions (3610, 3624) that help align one catheter relative to another catheter in adjacent blood vessels and/or bring the catheters (and blood vessels) in closer approximation relative to each other. Alignment of the first and second catheters (3602, 3604) relative to each other may position the electrode (3606) of the first catheter (3602) at a desired axial and/or rotational orientation relative to a corresponding backstop (3608) of the second catheter (3604). The coaption regions (3610, 3624) may comprise one or more magnets, flat coaption surfaces, and/or visual alignment aids (e.g., rotational indicators).

Figure 36E:
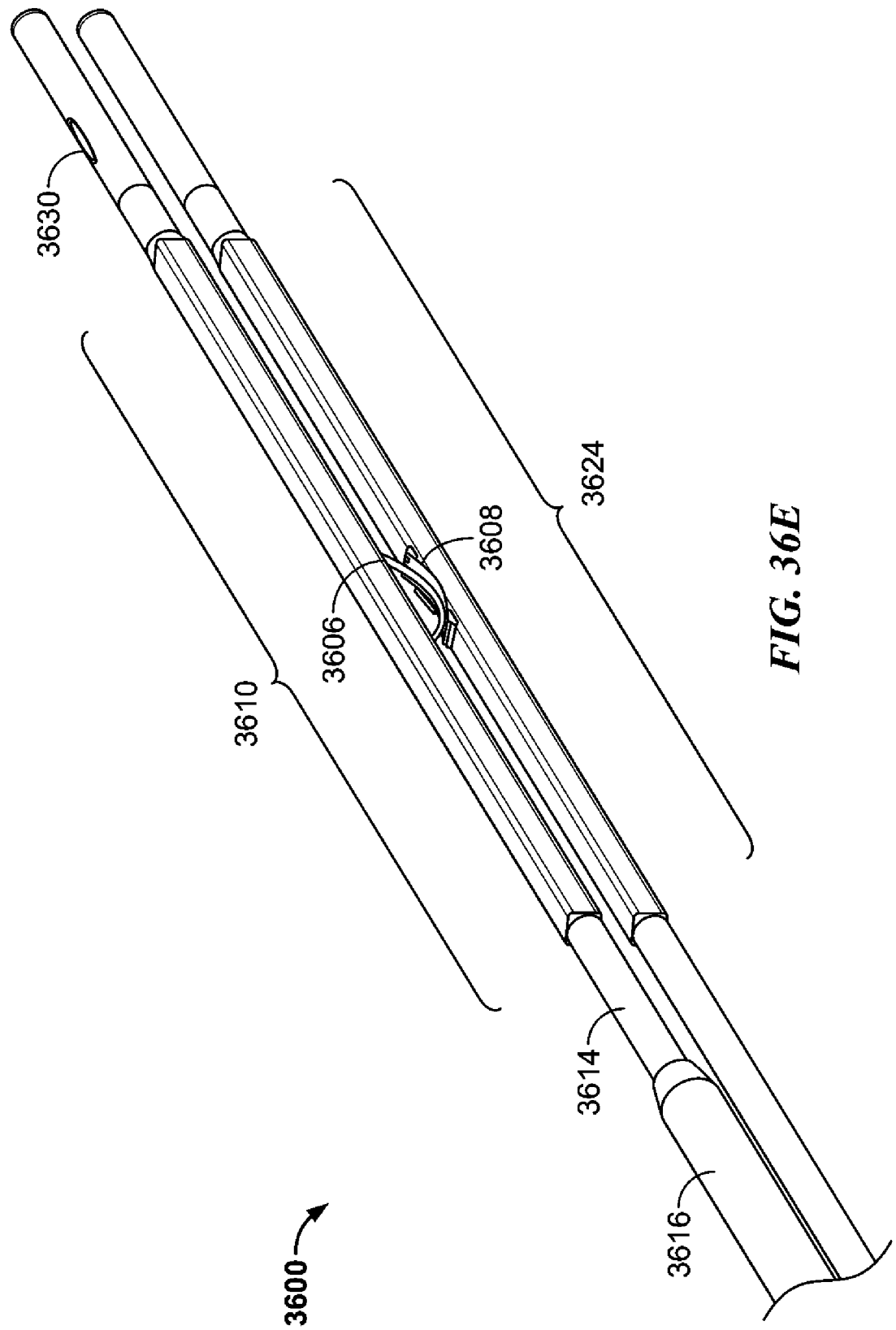

In particular, as best shown in the perspective view of FIG. 36E, the catheters may each have square cross-sections at least within the caption regions (3610, 3624). As such, one side of each coaption region (3610, 3624) may form a flat coaption surface, and the two coaption surfaces may face each other when the catheters are properly aligned, as shown in FIG. 36E. As described herein, this may aid the rotational alignment of the catheters; the opposing flat coaption surfaces may bring the catheters into rotational alignment with each other and closer together with the blood vessels.

Furthermore, the catheters (3602, 3604) may comprise magnet arrays comprising a plurality of square magnets (3626) within the coaption regions (3610, 3624). In the first catheter (3602), the square magnets (3626) may be located proximally and distally to the electrode (3606), as shown in FIG. 36B, while in the second catheter (3604), the square magnets may be located proximally and distally to the backstop (3608). The magnets (3626) proximal to the electrode (3606) in the first catheter (3602) may comprise a lumen for the electrical lead (3622). The electrical lead (3622) may be covered by insulation to shield the magnets (3626) from current carried by the lead (3622). The magnets (3626) of the first catheter (3602) may be attracted to magnets of the second catheter (3604) to bring the catheters in closer approximation and into rotational alignment. This may coapt tissue between the flat coaption surfaces. In some variations, the catheters (3602, 3604) may comprise one or more rotational indicators within the coaption regions (3610, 3626), which may be visualized under fluoroscopy for a user to visualize the catheter system (3600) in the blood vessels and manipulate the catheters (3602, 3604) into a desired position and relative orientation.

Figure 36F:
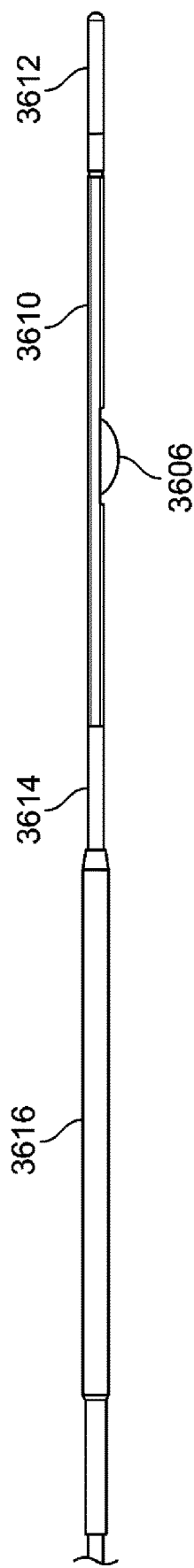

The catheter system (3600) may comprise a sheath (3616) configured to cover a portion of a catheter shaft (3614), as shown in FIG. 36F. The sheath (3616) may be slidable along the length of the first catheter (3602). In some variations, in order to be slidable over portions of the catheter having a circular cross-section and portions of the catheter having a square cross-section, the sheath (3616) may comprise a flexible material allowing it to deform between round and square tubular shapes. In some variations, the sheath (3616) may have a length similar to the length of the coaption region (3610). In a distal position, the sheath (3616) may cover the coaption region (3610), including the electrode (3606) and the areas of the catheter (3602) comprising magnets (3626), and may additionally cover portions of the remainder of the catheter shaft (3614). When the sheath (3616) covers the electrode (3606), the electrode (3606) may be held in a low-profile configuration. In a proximal position, the sheath (3616) may leave the coaption region (3610), including the electrode (3606), exposed, thus allowing the electrode (3606) to return to an extended configuration (assuming no other force constrains the electrode). Prior to delivery of the catheter (3602) into a patient's vasculature, the sheath (3616) may be in the distal position covering the electrode (3606). As discussed herein, when the sheath (3616) disposed over the catheter (3602) is advanced into a vessel through an access site comprising a hemostasis valve, the distal end of the sheath (3616) may, for example, be advanced into the valve, while the catheter (3606) may be advanced through the valve and sheath (3616) and into the vasculature. As the catheter (3602) is advanced, the sheath (3616) may slide proximally along the catheter shaft (3614). In this manner, the electrode (3606) in a low-profile configuration may be covered by the sheath (3616) to protect the electrode (3606) and catheter (3602) from catching and/or damage as they are advanced through the access site.

Figure 36G:
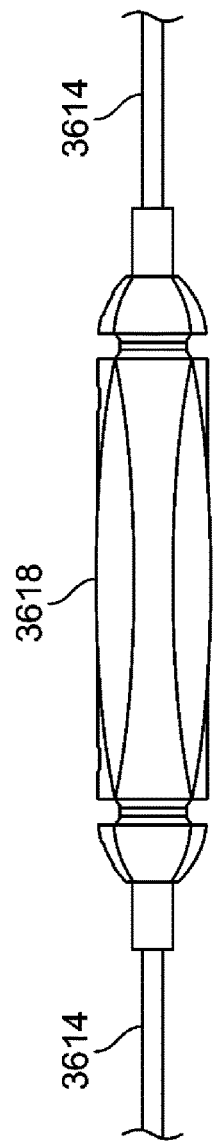

One or both catheters (3602, 3604) may comprise a handle (3618) as shown in FIG. 36G. The handle (3618) may be located proximal to the coaption region (3610) and distal to the electrical plug (3620), and may be coupled to the catheter shaft (3614). The handle (3618) may be used to align at least a proximal end of one catheter relative to at least a proximal end of another catheter. One or more portions of the catheter shaft (3614) may be torsionally stiff such that rotation of the handle (3618) is translated into rotation of the more distal portions of the catheter. At their distal ends, the respective distal ends (3612, 3628) of the catheters (3602, 3604) may each include a rapid exchange atraumatic tip comprising a lumen (3630) configured to pass a guidewire and allow tracking of the catheter over the guidewire.

II. Methods

Also described here are methods for forming a fistula between two blood vessels using the catheters described herein. The two blood vessels may be two closely-associated (e.g., adjacent) blood vessels, such as a vein and an artery, two veins, or two arteries. Generally, the methods described here comprise accessing a first blood vessel with a first catheter, and advancing the first catheter to a target location within a first blood vessel. A second blood vessel may be accessed with a second catheter, and the second catheter may be advanced to a target location within the second vessel. Once the first and/or second catheters have been advanced into the respective blood vessels, the catheters may be adjusted to position the catheters within the blood vessels and/or position the blood vessels relative to each other.

In some variations, the catheters may comprise alignment features as described herein that may be used to bring the two vessels toward each other and/or to align the catheters axially and/or rotationally relative to each other. The methods of aligning a catheter as disclosed herein may improve fistula formation with fewer complications. After the vessels are brought toward each other and the catheters are aligned, a fistula formation site may optionally be analyzed through measurements performed by one or more catheter electrodes. In some variations, the blood vessels may be modified by the electrodes prior to fistula formation to improve fistula and flow characteristics, as described in more detail herein. In some instances, denaturing of tissue may improve patency and blood flow of the fistula.

In some variations, one or more fistula-forming elements may be activated to bore through, perforate, or otherwise create a passageway between the two blood vessels by ablating tissue such that blood may flow directly between the two adjoining blood vessels. When such a fistula is formed, hemostasis may be created without the need for a separate device or structure (e.g., a suture, stent, shunt, or the like) connecting or joining the blood vessels. Throughout the fistula formation process, the condition of the blood vessels may in some variations be monitored, for example to refine the energy applied to ensure desired fistula formation. The catheters may be removed from the blood vessels and body after fistula formation. In some variations, fistula formation may be confirmed by the catheter measurements.

Figure 35:
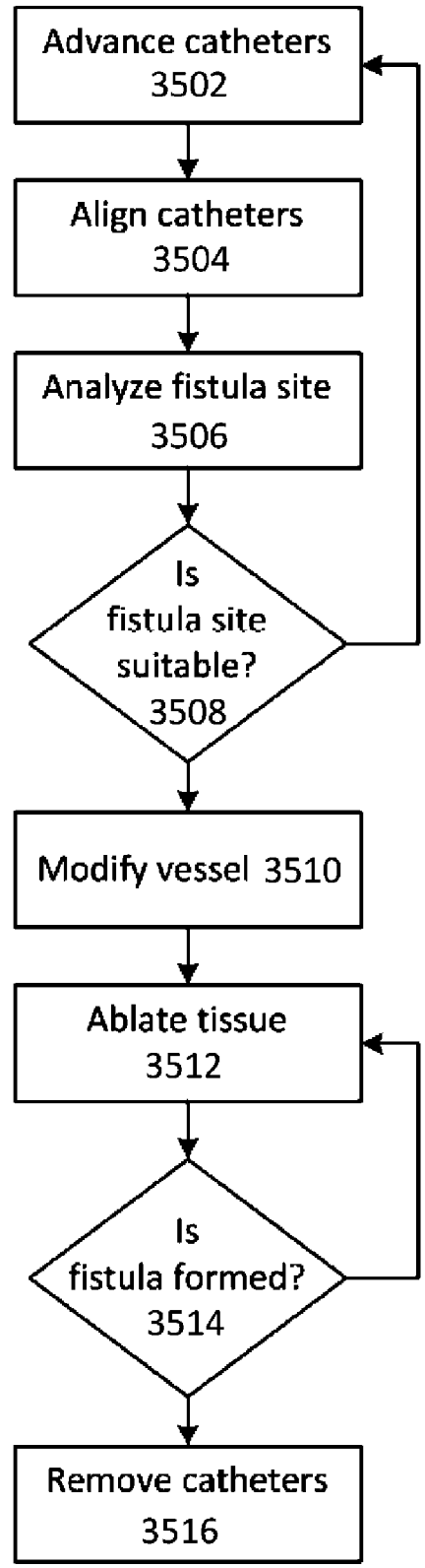
FIG. 35 is a flowchart illustrating a variation of a method for forming a fistula.

FIG. 35 is a flowchart generally describing a fistula-forming process (3500). It should be appreciated that any of the catheters described herein may be used to form a fistula using the methods herein as appropriate. Generally, the process may begin where one or more catheters are advanced to a target location in one or more blood vessels via an access site (3502). The first and second catheters may be advanced in the same manner, or may be advanced in different manners. Once the first and/or second catheters have been advanced into their respective blood vessels, the catheters may be aligned axially and rotationally with respect to each other (3504). For instance, each catheter may comprise one or more alignment features such as magnets, flat coaption surfaces, visual alignment aids, handles, or the like that help to position the catheters into a desired alignment. Additionally or alternatively, indirect visualization such as fluoroscopy may be utilized to align the catheters at a target location. In some variations, impedance measurement may confirm alignment of the catheters to each other.

In some variations, an analysis of the blood vessels may be optionally performed to determine if the site is suitable for fistula formation (3506). For instance, a nerve that is too close to a fistula site may be negatively impacted by the high temperatures experienced during a fistula ablation process. In some variations, the proximity of a nerve to a fistula site may be determined using electrode measurements. Based on the measurements of the fistula site, a determination may be made of whether the fistula site is suitable for fistula formation (3508). If the fistula site is unsuitable, the user may reposition the catheters (3502) to a new fistula site and repeat the alignment (3504), analysis (3506), and determination (3508) steps. In some variations, tissue at a fistula site or adjacent thereto may be optionally modified prior to ablation (3510). For example, the electrodes may be used to non-ablatively denature tissue to increase mechanical strength and/or shrink vessel size. For instance, a current may be applied to a location in the vessel to denature adventitia of the blood vessel.

Tissue may be ablated to form a fistula based on patient characteristics and fistula requirements (3512). Plasma may be generated according to energy ablation parameters to ablate tissue. Ablation may be performed by one or more electrodes in one or more catheters. In some variations, a first and second catheter may form a fistula from opposing sides so as to provide dual ablation of a fistula. In some of these variations, synergistic ablation may be provided where an electrode of a first catheter ablates tissue to activate a conductive portion of a second catheter. In yet other variations, a first catheter may form a fistula using an electrode against a backstop of a second catheter. Fistula formation may optionally be confirmed, for example through impedance measurement (3514). The catheters may be removed from the blood vessels and body (3516). The steps described above are described in further detail below.

A. Advance Catheter

Advancement of one or more catheters through a vessel to a target site is not particularly limited. In some variations, a first catheter may be advanced into an artery, and a second catheter may be advanced into a vein. In other variations, a first catheter may be advanced into a vein, and a second catheter may be advanced into an artery. In other variations, a first catheter may be advanced into a first vein, and a second catheter may be advanced into a second vein. In still other variations, a first catheter may be advanced into a first artery and a second catheter may be advanced into a second artery. The first and/or second catheters may be advanced over a guidewire or in any suitable manner and may or may not occur under indirect visualization (e.g., via fluoroscopy, X-ray, or ultrasound). A direction of catheter advancement with respect to blood flow is also not particularly limited—that is, a catheter may be advanced in an antegrade manner (with blood flow), or in a retrograde manner (against blood flow).

In variations where a catheter is advanced endovascularly into the ulnar artery, access to the ulnar artery may be achieved in any suitable manner. In some variations, the methods described here comprise endovascularly advancing a distal portion of a first catheter into an ulnar artery, endovascularly advancing a distal portion of a second catheter into a first deep ulnar vein, and forming a fistula between the ulnar artery and the first deep ulnar vein. The methods may comprise endovascularly advancing a distal portion of a first catheter into a proximal ulnar artery, endovascularly advancing a distal portion of a second catheter into a first deep ulnar vein, and forming a fistula between the proximal ulnar artery and the first deep ulnar vein.

In some variations, the catheter may be advanced along the brachial artery and into the ulnar artery. In some of these methods, the catheter may be introduced into the vasculature via a brachial access site. In some of these methods, the brachial artery may be cannulated with a cannula directed distally in the brachial artery. In other variations, the catheter may be advanced along the brachial artery from an access site upstream of the brachial artery. For example, the catheter may introduced into the vasculature via a femoral artery access site, and may be advanced to the brachial artery therefrom. In some variations, the ulnar artery may be accessed directly. In some of these variations, an ulnar access site may be formed in the ulnar artery (e.g., at a distal location in the wrist or forearm where the ulnar artery is superficially positioned), and a catheter may be advanced in a retrograde fashion through the ulnar access site. In still other variations, a catheter or other tool may be advanced endovascularly into the ulnar artery through an access site in the radial artery.

In variations where a catheter or other tool is advanced endovascularly into a deep ulnar vein, access to the deep ulnar vein may be achieved in any suitable manner. In some variations, the catheter is introduced into the vascular site via an access site. The venous access site may be in any suitable blood vessel, such as the basilic vein, the cephalic vein, or a brachial vein. In some variations, the catheter may be advanced to a deep ulnar vein endovascularly along the median cubital vein. For example in some variations, the catheter may be advanced along the basilic vein, into the median cubital vein, and into one of the deep ulnar veins via the perforating branch extending between the median cubital vein and the deep ulnar veins. In instances where the perforating branch extends between the deep ulnar veins and the median antebrachial vein, the catheter may be advanced from the median cubital vein into the median vein, then into one of the deep ulnar veins.

In other variations, the catheter may be advanced to a deep ulnar vein endovascularly along the median cephalic vein. For example, in some variations, the catheter may be advanced into the vasculature through an access site in the cephalic vein, and may be endovascularly advanced from the cephalic vein into the median cephalic vein, and into one of the deep ulnar veins via a perforating branch (to access the perforating branch, it may be necessary to advance the catheter into either the median cubital vein or the median antebrachial vein).

In still other variations, the catheter may be advanced to a deep ulnar vein endovascularly along a brachial vein. For example, in some variations, the catheter may be advanced into the vasculature through an access site in a brachial vein, and may be endovascularly advanced from the brachial vein into one of the deep ulnar veins in a retrograde fashion.

Methods for advancing a catheter endovascularly are described in more detail in U.S. patent application Ser. No. 14/052,477, filed on Oct. 11, 2013, and titled "DEVICES AND METHODS FOR FISTULA FORMATION," which is hereby incorporated by reference in its entirety.

In variations where one of the catheters is configured for advancement over a guidewire, the catheter may be advanced along a guidewire. In variations where one of the catheters has a guidewire fixedly attached to its tip, the guidewire may be advanced through the vasculature to a target location. In other variations, one or more external magnets may help advance or position a catheter at a target site. For example, an external magnet may be used to help advance catheter within a blood vessel and interact with any suitable portion of the catheter to create an attractive force between the catheter and the external magnet. This attractive force may be used to pull, push, or otherwise manipulate the catheter during advancement.

In variations where a catheter comprises an electrode having low-profile and extended configurations as described in detail herein, the electrode may be in a low-profile configuration as the catheter is advanced. Trauma due to advancement and navigation of the catheter through a blood vessel may be reduced by recessing the electrode into the housing. For example, in some variations, a distal end of the electrode may be configured to slide freely within a catheter housing in response to an external force, such as force from a vessel wall, as described in more detail herein. As the diameter of a vessel through which the catheter advances increases, the electrode may extend away from the housing by virtue of its spring force. Accordingly, a user need not mechanically recess or extend the electrode during advancement of the catheters through a vessel or during the fistula forming process.

B. Align Catheters

In some variations, each of the first or second catheters may comprise one or more alignment features, such as but not limited to magnets, flat coaption surfaces, visual alignment aids, and/or handles, as described in detail herein. In some variations, alignment of the first and second catheters to each other may comprise axial and/or rotational alignment. For example, the catheters may be oriented such that a fistula-forming element of at least one of the first or second catheters is positioned to form a fistula in a certain location. In variations in which both the first and second catheters comprise fistula-forming elements, the catheters may be oriented to align these fistula-forming elements opposite each other. In variations in which a first catheter comprises an electrode and a second catheter comprises a backstop, the catheters may be oriented to align the electrode and backstop opposite each other.

In some variations of catheters described herein, magnets within the first and second catheters may generate an attractive force between the catheters, which may pull the catheters toward each other. The attractive force may also compress tissue between the first and second catheters. An aligning torque may also mate the catheters together along respective flat coaption surfaces to achieve rotational alignment. In some variations, the catheters may be torsionally stiff such that rotational alignment of the handles by a user at a proximal end of the first and second catheters translates into rotational alignment through a distal end of the catheters.

The catheters may be visualized fluoroscopically as necessary throughout the fistula formation process. In variations of catheters comprising rotational indicators, axial and rotational catheter alignment may be indirectly visualized, such as through fluoroscopy, to assist a user in axially and/or radially aligning the catheters relative to each other. For example, under fluoroscopic imaging, rotational indicators may be rotated until they appear the same under fluoroscopic visualization in order to rotationally align the catheters relative to one another. This ensures that the rotational indicators are aligned relative to one another, and not relative to the X-ray imaging beam. Once aligned, a user may bring the catheters into close approximation such that the catheters' magnets hold the aligned catheters together.

In some variations, confirmation of alignment (e.g., axial and/or rotational) of the first and second catheters may be based on impedance measurements of the tissue interposed between the two electrodes. For instance, the catheters may be rotationally and axially aligned when the electrodes are at a minimum distance from each other, which corresponds to a minimum tissue impedance between the catheters. Confirmation of alignment using impedance measurement may avoid radiation exposure resulting from other methods, such as fluoroscopy.

In one variation, the system may comprise an impedance metering circuit such as a bipolar sensing circuit comprising the tissue ablation electrodes. To measure impedance, low power DC or alternating voltage may be applied to the electrodes. The resulting current and/or phase may be measured to determine impedance. As a user manipulates one or more catheters relative to each other, the measured impedance values may change to allow determination of a minimum impedance. Additionally or alternatively, tetrapolar measurements with filtration/signal conditioning may be utilized to determine impedance.

In some variations, one or more impedance measurements may be outputted to a user as one or more of visual and audio feedback. For example, the system may output an impedance value on a display meter coupled to the catheters. Additionally or alternatively, impedance values may be output as audio tones. For instance, a predetermined tone may indicate a minimum impedance value corresponding to catheter alignment.

C. Analyze Vessel

Once a potential fistula site has been identified and one or more catheters have been advanced to the fistula site, measurement of vessel characteristics may optionally be used to determine the suitability of the site for fistula formation. In some variations, the suitability of a site for fistula formation may be based on the proximity of the site to a nerve. For instance, it may be undesirable to form a fistula close to a nerve, as the thermal energies of fistula formation may impinge on one or more nearby nerves.

In some variations, a system may apply a low power DC or AC current in a monopolar configuration through an active electrode of a first catheter to a ground pad to induce neuromuscular stimulation. Nerve location with respect to the fistula site may be determined based on visualization of the induced neuromuscular stimulation. The stimulation may be visualized externally (e.g., observing an arm twitch) and/or internally through techniques such as ultrasound and/or fluoroscopy. A high level of induced neuromuscular stimulation may indicate that the fistula site is too close to a nerve and may suggest that the fistula site should be relocated by repositioning the catheters. In some variations, a set of stimulating currents may be applied to determine the distance of the nerve from the electrode. For instance, a current of 1 microampere may be applied and then followed by a current of 3 microamperes. The difference in observed neuromuscular stimulation may approximate nerve vicinity.

In some variations, a baseline impedance measurement may be performed prior to fistula formation and utilized to determine ablation parameters. Baseline impedance may also be referenced when performing a second impedance measurement to confirm fistula formation after tissue ablation.

D. Modify Vessel

In some variations of the methods described herein, portions of the vessels adjacent to a fistula site may be modified to change the characteristics of one or more vessels and the resultant fistula. In some variations, one or more catheters may be configured to thermally denature and/or weld tissue structures at or adjacent to a fistula site. For example, heating tissue to 70° C. may result in denaturing. Thermal denaturing and welding may modify the vessel without removing material as occurs when ablating tissue. Furthermore, adhesion of tissue layers may be beneficial towards increasing the mechanical strength between vessels.

In some variations, one or more catheters may be configured to deliver electrical, ultrasonic, or laser energy to at least one of the first and second blood vessels to denature proteins in the vessel walls. For example, a catheter may comprise a fiber optic filament coupled to a laser, such that the catheter may be configured to direct laser energy to heat tissue, denature proteins, and/or weld tissue. As another example, a catheter may comprise a piezoelectric element configured to use ultrasonic vibration to induce heating, denature proteins, and/or weld tissue. In some instances, tissue may be thermally welded by applying a coagulation current through an electrode to denature connective tissue proteins and thereby increase adhesion between tissue planes. A coagulation current may thermally shrink the vessel and increase the vessel's vascular resistance. In some instances, the denatured proteins from each blood vessel may intertwine to fuse together. In one variation, denaturing collagen around a fistula site without removing tissue is performed prior to the ablation cycle to strengthen the fistula formed. However, a denaturing sequence may be performed before, during, or after fistula creation.

Additionally or alternatively, impedance may be measured during a thermal denaturing period by measuring the impedance in a bipolar or monopolar circuit. As described herein, first and second catheters may comprise an impedance metering circuit, such as a bipolar sensing circuit. In this manner, a single heating cycle may be performed without interrupting the energy delivery cycle to measure impedance. Impedances measured (e.g., using a first electrode and a second electrode) before and after a denaturing sequence may determine the level of vessel modification provided.

In some variations, the systems discussed herein may further comprise an electrosurgical controller coupled to one or more electrodes for controlling tissue modification. In some variations, a first impedance may be measured between a first electrode and a second electrode. Tissue modification parameters may be selected based on the first impedance. For instance, the impedance measured may correspond to known tissue characteristics. These tissue characteristics may correspond to predetermined tissue modification parameters. Modification parameters may include an energy waveform, amplitude, duration, and so forth. The controller may control one more electrodes to modify tissue based on the selected modification parameters. After applying one or more pulses of tissue modification energy, a second impedance may be measured, and the process may be repeated until a threshold impedance is reached.

The controller may control the electrodes to measure a second impedance and determine whether modification is complete based on the impedance. In some variations, parameters may be selected to complete modification in a single cycle. In other variations, each cycle may be limited in power and/or duration so as to perform a plurality of cycles to complete modification. For example, the thermal effects of denaturing may be dispersed over a longer period of time so as to limit collateral thermal damage to a vessel.

Devices, systems, and methods for modifying vessels are described in more detail in International Patent Application Serial No. PCT/US17/13611 filed concurrently herewith, titled "SYSTEMS AND METHODS FOR ADHERING VESSELS" and claiming the benefit of U.S. Provisional Application No. 62/279,642, filed Jan. 15, 2016, which is hereby incorporated by reference in its entirety.

E. Ablate Tissue

Once the catheter or catheters are in position, one or more fistula-forming elements may be used to create a fistula between the two blood vessels. For example, in some variations, one of the first and second catheters may comprise a fistula-forming element (e.g., an electrode), while the other catheter does not comprise a fistula-forming element. In other variations, both catheters may comprise a fistula-forming element. In some of these variations, the fistula-forming elements of the first and second catheters act to form different fistulas. In other variations, the fistula-forming elements of the first and second catheters interact to form the same fistula. Any suitable combination of electrodes as described herein may be utilized to form the fistula, and current may be delivered in monopolar or bipolar configurations accordingly. For example, a fistula-forming element of the first catheter may be activated or otherwise used to form a fistula between a first blood vessel and a second adjoining blood vessel. In still other variations, the catheters may be configured to form the fistula through the first and second blood vessels substantially simultaneously.

As discussed in detail herein, in variations where the fistula-forming element of the first catheter is configured to extend or otherwise move through blood vessel tissue during tissue fistula formation, a second catheter may contact or otherwise receive the fistula-forming element of the first catheter as it ablates through tissue. For example, in some variations, the second catheter may comprise one or more backstops, such as those discussed with respect to FIGS. 13A-18B. In some of these variations, the backstop may be configured to receive or otherwise contact an electrode of the first catheter as it passes through vessel tissue. In other variations, current may be passed between an electrode of the first catheter and an electrode of the second catheter during tissue ablation. In some of these variations, the electrode of the first catheter may be positioned such that it comes into contact with one or more electrodes or conductive portions of the second catheter.

For example, in the variations illustrated in FIGS. 20A-20D, advancement of an active electrode (2008) through tissue of one blood vessel may contact and energize the one or more conductive portions (2002) in a second catheter in a second blood vessel. In these variations, a first blood vessel may be a venous blood vessel and a second blood vessel may be an arterial blood vessel, for example. Prior to contact of the electrode (2008) with the conductive portion (2002), only the electrode (2008) is energized to ablate tissue. Upon contact of the electrode (2008) with the conductive portion (2002), the voltage of the conductive portion (2002) rises to become an extension of the electrode (2008), such that the conductive portion (2002) may ablate tissue in contact with the electrode (2008). When contact is broken between the electrode (2008) and the conductive portion (2002), the voltage of the conductive portion (2002) drops and ablation by the conductive portion (2002) ends.

In variations where a fistula is formed between an artery and a vein, it may be desirable in some instances to begin fistula formation in the vein prior to forming an opening in the artery wall. If during fistula formulation, the first catheter malfunctions or the procedure is otherwise stopped, such that a complete fistula is not formed, formation of an opening formed in the artery without a corresponding opening being formed in the vein is prevented. Formation of an opening in a vein without fully forming a fistula may result in some extravascular bleeding, but the venous pressure may be low enough such that significant bleeding does not occur, which may allow the blood vessel to heal itself. In contrast, when an opening is formed in an artery without completely forming a fistula, the arterial pressure may push blood into the extravascular space around the blood vessels, which in some instances may require a surgical procedure to fix. Moreover, ablation of a fistula of a larger size on a venous side of the fistula versus a smaller size on the arterial side may reduce intrafistular pressure so as to reduce the likelihood of extravasation. This is accomplished by inducing a larger pressure drop at the arterial fistula aperture. Additionally, in some variations, fistula formation using the methods described herein may form a larger opening in the first blood vessel than the opening formed in the second blood vessel. This may be useful in instances where the first blood vessel is a vein and the second blood vessel is an artery. Because a larger opening may have less resistance to blood flow than a smaller opening, forming a larger opening in the vein may promote flow from the artery to the vein, which may reduce the likelihood of blood extravasation through a fistula into the extravascular space.

In some variations, radiofrequency energy such as radiofrequency alternating current may be applied to one or more electrodes to generate plasma and ablate tissue as discussed in detail herein. In some variations, the parameters may be selected based on tissue properties. For example, an impedance may be measured between a first electrode and a second electrode. Tissue ablation parameters may be selected based on the impedance. For instance, the measured impedance may correspond to known tissue characteristics. In conjunction with desired fistula characteristics, predetermined tissue ablation parameters may be selected. Tissue ablation parameters may include an energy waveform, amplitude, duration, and so forth. The controller may control the one more electrodes to ablate tissue based on the selected ablation parameters.

In some variations, tissue ablation parameters may be selected to form a fistula in a single ablation cycle. In other variations, each cycle may be limited in power and/or duration so as to perform a plurality of cycles to complete ablation. In these variations, the thermal effects of ablation may be dispersed over a longer period of time so as to limit collateral thermal damage to a vessel.

Upon applying voltage to an electrode, fluid surrounding the active electrode may be heated to generate a vapor layer. The vapor layer generated rapidly expands and encapsulates the electrode such that the vapor increases the impedance experienced at the electrode. Plasma is generated from the vapor layer when the voltage applied to the electrode exceeds an ionization threshold. The plasma generates electrical arcs with high current density that superheats tissue and causes rapid dissociation of molecular bonds in the organic compounds.

In variations of a catheter comprising a reservoir formed behind an electrode, a fixed volume of blood may be held in the reservoir. This isolation creates a fluid bolus separated from the free stream of blood and allows a significant reduction in the time and energy needed to generate plasma for ablation. For example, when the electrode is energized, the fluid volume in the reservoir may rapidly vaporize and ionize, thereby initiating the ablation sequence quickly. In configurations comprising a fluid reservoir, the time to reaching ablation plasma may be significantly reduced from about 500 msec to about 15 msec. Reducing the time until plasma ignition may also reduce the total energy applied to tissue, thereby reducing potential collateral thermal damage to tissue. Without the reservoir, the electrode may have greater difficulty in generating plasma due to convection from the free flowing bloodstream.

The maximum voltage applied may exceed an ionization threshold of a vapor layer. In some variations, an ionization threshold of a vapor layer may be exceeded by applying a peak voltage of about 180 V. In some variations, a constant voltage square wave may be applied via one or more of the electrodes to reduce the overall amount of energy used to generate and maintain plasma. For example, due to the shape and periodic nature of a sinusoidal waveform, a significant portion of a sinusoidal voltage is below an ionization threshold. To compensate, the maximum voltage is increased, thereby increasing energy usage and also potentially causing unintended damage to a vessel. However, a constant voltage square wave may be above the ionization threshold for a higher percentage of each cycle period in comparison to a sinusoidal waveform. Consequently, tissue ablation may be performed with less energy.

In some variations, the systems discussed herein may further comprise an electrosurgical controller coupled to one or more electrodes for controlling tissue ablation. For example, in some variations, the electrosurgical controller may control one or more electrodes in one or more catheters. In other variations, the electrosurgical controller may control a first catheter comprising one or more electrodes paired with a second catheter comprising a backstop.

In some variations, the system may comprise a feedback circuit to maintain the voltage at a constant level. By maintaining a constant voltage square wave, higher current may be delivered during an ionic conduction phase when vapor is not yet formed and impedance is low. As vapor is formed, the impedance rises and the current may be reduced accordingly as a function of the constant voltage control of the feedback circuit. The voltage may be maintained at a predetermined level to provide a desired ionization intensity of the plasma. The feedback circuit may comprise any known control scheme such as P (proportional), PI (proportional-integral), PID (proportional-integral-derivative) control, or the like.

The size of the fistula formed may vary in size as a function of the tissue thickness. For example, if the tissue is thin, limiting the extension of the electrode out of a catheter housing by way of a protruding backstop, for instance, may produce a smaller fistula. For thicker tissue, the electrode may be designed to extend further out of the catheter housing to thereby increase the width of the formed fistula. Thus, a predetermined fistula resistance (e.g., fluid flow rate) may be maintained in the presence of variable tissue thickness.

The impedance between the electrodes may be measured before, during, and/or after an ablation cycle to measure the resistive changes in the tissue as caused by the ablation. As the tissue is removed via ablation and blood communicates through the newly-formed fistula, an impedance between the electrodes may drop significantly and may indicate successful fistula creation. Conversely, if the impedance has not dropped to a predetermined level, a fistula may be determined to have not completely formed. A measured impedance within a predetermined range may correspond to a created fistula. In one variation, a measured impedance of about 150 ohms or less may indicate fistula formation.

For example, a first impedance may be measured between an electrode in the first vessel and an electrode in the second vessel. After tissue ablation, a controller controls the electrodes to measure a second impedance and determine whether a desired fistula has been created using the first impedance as a reference. In one variation, an ablation parameter may comprise a tissue ablation period of 40 msec followed by a 20 msec impedance measurement period without delivery of tissue ablation energy. In another variation, an ablation parameter may comprise a tissue ablation period of about 500 msec followed by an impedance measurement period of about 1 second. In some of these variations, the measured impedance may be averaged over the measurement period. This ablation cycle alternating between measurement and ablation may be repeated until a fistula is created. In some variations, the completion of fistula formation may be indicated to a user via visual and/or audio feedback such as a confirmatory tone and/or display message. Fistula creation and confirmation may thus confirmed without fluoroscopy. However, it should be appreciated that additionally or alternatively, fistula creation may be confirmed using imaging, such as using fluoroscopy and injection of a contrast agent.

Additionally, in some variations, one or more balloons or expandable members, such as those described herein, may be used to help position the first and/or second catheters, or may act to hold the first and/or second catheters in place within the blood vessels. For example, in some variations, expansion of a balloon or expandable member of one of the catheters may engage the interior of a blood vessel, which may hold that catheter in place within the blood vessel. In other methods, the expansion of the balloon or expandable member can bias or otherwise press a fistula-forming element against blood vessel tissue, which may aid fistula formation.

Additionally, one or more balloons may be activated to affect the blood flow relative to the fistula. For example, in variations where an arterio-venous fistula is formed, it may be beneficial to dilate one or more portions of the artery and/or veins. Specifically, the portion of the artery upstream of an arterio-venous fistula may be expanded to increase flow through the fistula. Alternatively or additionally, a portion of a vein downstream from a fistula may be dilated to help increase flow through the fistula. In some variations, one or more portions expandable members may comprise an electrode for inducing necrosis or swelling in a portion of a blood vessel to decrease flow therethrough. For example, in some variations a portion of a vein upstream from a fistula may be at least partially occluded to minimize venous hypertension.

Although the foregoing implementations has, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices described herein may be used in any combination, and the methods described herein may comprise all or a portion of the elements described herein. The description of certain elements or characteristics with respect to a specific figure are not intended to be limiting or nor should they be interpreted to suggest that the element cannot be used in combination with any of the other described elements.

We claim:

1. A system for forming a fistula between two vessels comprising:
    a first catheter comprising a housing and an electrode,
    wherein the electrode comprises a proximal end, a distal end, and an intermediate portion between the proximal end and the distal end;
    wherein the electrode varies in width along a length defined from the proximal end to the intermediate portion, and
    wherein the proximal end of the electrode is fixed relative to the housing and the distal end of the electrode is freely longitudinally slidable within the housing toward a tip of the catheter away from the proximal end.

2. The system of claim 1, wherein the housing comprises a side opening and the intermediate portion of the electrode extends into and out of the side opening radially beyond an outer radius of the housing.

3. The system of claim 1, wherein the electrode comprises a leaf spring.

4. The system of claim 1, wherein the first catheter comprises a fluid seal to prevent fluid ingress into the first catheter at the proximal end of the electrode.

5. The system of claim 1, wherein the electrode varies in height along its length.

6. The system of claim 1, wherein the intermediate portion of the electrode comprises a plurality of bends.

7. The system of claim 1, wherein the intermediate portion comprises a bend of less than about 40 degrees.

8. The system of claim 1, wherein the electrode comprises a low-profile configuration in which the electrode is recessed into the housing.

9. The system of claim 1, wherein the housing comprises a reservoir between the proximal end of the electrode and a distal end of the first catheter, the reservoir configured to hold fluid, and wherein the electrode is configured to generate plasma from the fluid in the reservoir.

10. The system of claim 1, further comprising a second catheter comprising a second housing and a protruding backstop.

11. The system of claim 10, wherein the second catheter comprises a recessed portion opposite the protruding backstop across a longitudinal axis of the second catheter, wherein the recessed portion has a complementary shape to the protruding backstop.

12. The system of claim 1, further comprising a second catheter comprising a recessed backstop, wherein the recessed backstop has a shape that is complementary to a portion of the electrode.

13. The system of claim 12, wherein the recessed backstop has a shape that is complementary to the intermediate portion of the electrode.

14. The system of claim 13, wherein the electrode comprises an extended configuration in which the electrode is extended away from the housing, and wherein the complementary shape corresponds to a shape of the electrode in the extended configuration.

15. The system of claim 12, where the shape comprises a concave portion comprising an opening configured to receive the electrode.

16. The system of claim 1, wherein the first catheter comprises a first coaption region comprising a flat coaption surface.

17. The system of claim 16, wherein the first coaption region has a square or rectangular cross-section.

18. The system of claim 16, further comprising a second catheter comprising a second coaption region comprising a flat coaption surface.

19. The system of claim 18, wherein the second coaption region has a square or rectangular cross-section.

20. The system of claim 18, wherein the first coaption region comprises a first magnet and the second coaption region comprises a second magnet.

21. The system of claim 1, wherein the first catheter comprises a first handle, and the system further comprises a second catheter comprising a second handle, wherein the first handle and the second handle each comprise a flat surface.

22. The system of claim 21, wherein the first handle comprises a first magnet and the second handle comprises a second magnet.

23. The system of claim 1, wherein the first catheter comprises a rotational indicator comprising a radiopaque material.

24. The system of claim 1, wherein a width of the proximal end of the electrode is greater than the width of the intermediate portion of the electrode.

25. The system of claim 1, wherein the width of the electrode tapers from the proximal end to the intermediate portion.

26. The system of claim 1, wherein the electrode is positioned within a lumen of the housing, the lumen comprising a first diameter portion positioned proximal to the opening and a second diameter portion positioned proximal to the opening, wherein the second diameter portion comprises a smaller diameter than the first diameter portion, and the electrode is fixed to the housing at the second diameter portion.

27. The system of claim 1, wherein the tip of the catheter is a rapid exchange tip, and the distal end of the electrode remains spaced from the rapid exchange tip.

* * * * *